US012624381B2

(12) United States Patent
Mueller et al.

(10) Patent No.: US 12,624,381 B2
(45) Date of Patent: May 12, 2026

(54) ACETYL-CoA PRODUCING ENZYMES IN YEAST

(71) Applicant: DANISCO US INC., Palo Alto, CA (US)

(72) Inventors: Ulrike Maria Mueller, Echt (NL); Liang Wu, Echt (NL); Lourina Madeleine Raamsdonk, Echt (NL); Aaron Adriaan Winkler, The Hague (NL)

(73) Assignee: DANISCO US INC., Palo Alto, CA (US)

( * ) Notice: Subject to any disclaimer, the term of this patent is extended or adjusted under 35 U.S.C. 154(b) by 26 days.

(21) Appl. No.: 18/392,655

(22) Filed: Dec. 21, 2023

(65) Prior Publication Data

US 2024/0191277 A1 Jun. 13, 2024

Related U.S. Application Data

(63) Continuation of application No. 17/081,187, filed on Oct. 27, 2020, now abandoned, which is a continuation of application No. 14/045,683, filed on Oct. 3, 2013, now Pat. No. 10,927,399, which is a continuation of application No. 12/670,050, filed as application No. PCT/EP2008/059119 on Jul. 11, 2008, now abandoned.

(60) Provisional application No. 61/064,120, filed on Feb. 19, 2008, provisional application No. 60/935,031, filed on Jul. 23, 2007.

(30) Foreign Application Priority Data

Jul. 23, 2007 (EP) ..................................... 07112956
Dec. 21, 2007 (EP) ..................................... 07123976
Feb. 19, 2008 (EP) ..................................... 08101747

(51) Int. Cl.
| | |
|---|---|
| *C12Q 1/32* | (2006.01) |
| *C07K 14/33* | (2006.01) |
| *C12N 9/02* | (2006.01) |
| *C12P 7/16* | (2006.01) |

(52) U.S. Cl.
CPC ............... *C12Q 1/32* (2013.01); *C07K 14/33* (2013.01); *C12N 9/001* (2013.01); *C12P 7/16* (2013.01); *Y02E 50/10* (2013.01)

(58) Field of Classification Search
CPC .......... C12Q 1/32; C07K 14/33; C12N 9/001; C12P 7/16; Y02E 50/10
See application file for complete search history.

(56) References Cited

U.S. PATENT DOCUMENTS

| | | |
|---|---|---|
| 6,610,836 B1 | 8/2003 | Breton et al. |
| 7,927,861 B2 | 4/2011 | Mills et al. |
| 2003/0104523 A1 | 6/2003 | Bauer et al. |
| 2004/0235060 A1 | 11/2004 | Dhanasekaran et al. |
| 2005/0059136 A1 | 3/2005 | Van Maris et al. |
| 2005/0153411 A1 | 7/2005 | Wahlbom et al. |
| 2006/0078901 A1 | 4/2006 | Buchrieser et al. |
| 2008/0182308 A1 | 7/2008 | Donaldson et al. |
| 2009/0155869 A1 | 6/2009 | Buelter et al. |
| 2010/0159546 A1 | 6/2010 | Aristidou et al. |

FOREIGN PATENT DOCUMENTS

| | | |
|---|---|---|
| WO | 02077183 A2 | 10/2002 |
| WO | 2007041269 A2 | 4/2007 |
| WO | 2008080124 A2 | 7/2008 |
| WO | 2008121701 A1 | 10/2008 |
| WO | 200901360 A2 | 12/2008 |

OTHER PUBLICATIONS

Van den Berg et al. (The two acetyl-CoA synthetases of *Saccharomyces cerevisiae* differ with respect to kinetic properties and transcriptional regulation. JBC (1996), 271(46): 28953-28959) (Year: 1996).*
BioCyc, "Lactococcus lactis lactis 111403 EC 1.2. 1 10—acetaidehyde dehydrogenase (acetylating)" 2013, pp. 1-3.
Blomqvist, K. et al., "Chromosomal Integration and Expression of Two Bacterial a-Acetolactate Decarboxylase Genes in Brewer's Yeast", Applied and Environmental Microbiology, Oct. 1991, pp. 2796-2803.
Boubekeur et al., "A Mitochondrial Pyruvate Dehydrogenase Bypass in the Yeast *Saccharornyces cerevisiae*", J., Biol. Chem., Vo!. 274, No. 30, 1999, pp. 21044-21048.
Boxma et al., "The anaerobic chytridiornycete fungus *Pirornyces* sp. E2 produces ethanol via pyruvate:formate lyase and an alcohol dehydrogenase E", Mot. Microbial., vol. 51, No. 5, 2004, pp. 1389-1399.
Database EPO Proteins [OnLine], Accession No. AX639358, "Sequence 548 from Patent W00101118", Feb. 21, 2003, 1 page.
Database Geneseq [Online], Accession No. ABB47983, "Listeria monocytogenes protein #687", Feb. 5, 2002, 2 pages.

(Continued)

*Primary Examiner* — Iqbal H Chowdhury

(57) ABSTRACT

A method of identifying a heterologous polypeptide having enzymatic activity for converting pyruvate, acetaldehyde or acetate into acetyl-CoA in cytosol of a yeast cell comprising: a) providing a mutated yeast cell comprising a deletion of at least one gene of the by-pass, selected from the genes encoding the enzymes pyruvate decarboxylase, acetaldehyde dehydrogenase, and acetylCoA synthetase; b) transforming said mutated yeast cell with an expression vector comprising a heterologous nucleotide sequence encoding a candidate polypeptide having potential enzymatic activity for converting pyruvate, acetaldehyde or acetate into acetyl-CoA; c) testing said recombinant mutated yeast cell for its ability to grown on minimal medium containing glucose as sole carbon source, and d) identifying said candidate polypeptide as a heterologous polypeptide having enzymatic activity for converting pyruvate, acetaldehyde or acetate into acetyl-CoA in the cytosol of said yeast cell when growth of said cell is observed.

4 Claims, 4 Drawing Sheets

Specification includes a Sequence Listing.

(56)                    References Cited

OTHER PUBLICATIONS

Database Geneseq [Online], Accession No. ABB48178, "Listeria rnonocytogenes protein #882", Feb. 5, 2002, 2 pages.
Database Geneseq [Online], Accession No. ABU16560, "Protein encoded by Prokaryotic essential gene #2087", Jun. 19, 2003, 2 pages.
Database Geneseq [Online], Accession No. ABU25371, "Protein encoded by Prokaryotic essential gene #10898", Jun. 19, 2003, 2 pages.
Database USPTO Proteins [Online], Accession No. AAR49390, "Sequence 9107 form U.S. Pat. No. 6,610,836", Dec. 2003, 1 page.
De Virgilio et al., "Cloning and Disruption of a Gene Required for Growth on Acetate but not on Ethanol: The Acetyl-Coenzyme A Synthetase Gene of *Saccharomyces cerevisiae*", Yeast, Aug. 1992, pp. 1043-1051.
DNA SEQ alignment SCORE result for instant SEQ ID No. 51, 2013, pp. 1-3.
Flikweert, M. et al., "Pyruvate Dacarboxyiase: An Indispensable Enzyme for Growth of *Saccaromyces cerevisiae*, on Glucose", Yeast, vol. 12, 1996, pp. 247-257.
Hwang, Wen-Zhe et al., "Expression of a Bacterial ice Nucleation Gene in a Yeast *Saccaromyces cerevisiae* and Its Possible Application in Food Freezing Processes", J. Agric. Food Chem., vol. 49, 2001, pp. 4662-4666.
Kisselev, "Polypeptide release factors in prokaryotes and eukaryotes: same function, different structure", Structure, vol. 10, 2002, pp. 8-9.
Manjasetty et al., "Crystal structure of a bifunctional aldolase-dehydrogenase: Sequestering a reactive and volatile intermediate," PNAS, vol. 100, No. 12, Jun. 10, 2003, pp. 6992-6997.
NCBI Q99X67, "Alcohol-acetaldehyde detlydrogenase", 2006, pp. 1-2.
Remize et al., "Engineering of the Pyruvate Dehydrogenase Bypass in *Saccharornyces cerevisiae*: Role of the Cytoso!ic Mg21 and Mitochondrial K1 Acetaldehyde Dellydrogenases Ald6p and Ald4p in Acetate Formation during Alcoholic Fermentation", Appl. Environ. Microbial., vol. 66, No. 8, 2000, pp. 3151-3159.
Saint-Prix, F. et al, "Functional analysis of the ALD gene family of *Saccharomyces cerevisiae* during anaerobic growth on glucose: the NADP+-dependent Ald6p and Ald5p isoforms piay a major role in acetate formation", Microbiology, vol. 150, 2004, pp. 2209-2220.
SEQ alignment SCORE result for instant SEQ ID No. 52, 2013, pp. 1-2.
SEQ ID No. 51 Alignment (2015) pp. 1-7.
SEQ ID No. 52 Alignment (2015) pp. 1-3.
Van Den Berg et al., "ACS2, a *Saccharomyces cerevisiae* gene encoding acetyl-coenzyme A synthetase, essential for growth on glucose." Eur. J. Biochem. 231, 1995, 704-713.
Whisstock et al., "Prediction of protein function from protein sequence and structure", Quarterly Reviews of Biophysics, 36(3), 2003, pp. 307-340.
Witkowski et al., :Conversion of a beta-ketoacyl synthase to a malonyl decarboxylase by replacement of the active-site cysteine with glutamine, Biochemistry. 38(36), Sep. 7, 1999, pp. 11643-11650.
International Search Report for PCTIEP2008/059119, mailed Mar. 6, 2009.

* cited by examiner

ACETYL-CoA PRODUCING ENZYMES IN YEAST

CROSS REFERENCE TO RELATED APPLICATIONS

This application is a Continuation of U.S. application Ser. No. 14/045,683, filed Oct. 3, 2013, which is a Continuation of U.S. application Ser. No. 12/670,050, filed May 7, 2010, which is a § 371 National Stage Application of International Application No. PCT/EP2008/059119, filed Jul. 11, 2008, which claims priority to European Application No. 07112956.3, filed Jul. 23, 2007, U.S. Provisional Application No. 60/935,031, filed Jul. 23, 2007, European Application No. 07123976.8, filed Dec. 21, 2007, European Application No. 08101747.7, filed Feb. 19, 2008, and U.S. Provisional Application No. 61/064,120, filed Feb. 19, 2008, the content of all of which are incorporated herein by reference in their entireties.

INCORPORATION BY REFERENCE OF THE SEQUENCE LISTING

The present application is being filed with a Sequence Listing in electronic format. The Sequence Listing is provided as an XML file entitled "IFF26480-US-PCN3_SequenceListing.xml," created on Dec. 20, 2023, which is 43 KB in size. The information in the electronic format of the Sequence Listing is incorporated by reference in its entirety.

BACKGROUND OF THE INVENTION

The present invention is in the field of metabolites production in yeast using heterologous expression systems. In particular, the present invention relates to the metabolic engineering of yeast strains capable of producing metabolites that require cytosolic acetyl-CoA as a precursor, such as butanol-producing yeast strains. The present invention relates to an assay system for identifying heterologous enzymes capable of converting pyruvate, acetaldehyde or acetate into cytosolic acetyl-CoA when expressed in the cytosol in yeast.

Acetyl-coenzyme A (CoA) is an essential intermediate in numerous metabolic pathways, and is a key precursor in the synthesis of many industrial relevant compounds, such as fatty acids, carotenoids, isoprenoids, vitamins, amino acids, lipids, wax esters, (poly)saccharides polyhydroxyalkanoates, statins, polyketides and acetic esters (such as ethyl acetate and isoamyl acetate). In particular, acetyl-CoA is also the precursor of the industrially important bulk chemical 1-butanol.

Compared to bacteria, such as E. coli, yeast cells provide a very suitable alternative to produce the above-mentioned acetyl-CoA derived products, in that yeast is not susceptible to phage or other infection since yeast-based processes may be run at low pH. Therefore, the use of yeast does not require a sterile process, thereby lowering the cost price of the product of interest.

When natural (wild type) yeast is not able to produce the acetyl-CoA-derived product of interest, the use of metabolic engineering can provide for yeast cells expressing heterologous genes that could support such a process. In such cases, the heterologous gene products are usually targeted to the cytosolic compartment of yeast. As the biosynthesis of acetyl-CoA-derived product will take place completely or partially in the cytosol, the supply of sufficient amounts of the precursor acetyl-CoA in the cytosolic compartment is crucial. In Saccharomyces cerevisiae, biosynthesis of acetyl-CoA takes place in two separate compartments. In mitochondria, acetyl-CoA is synthesized by oxidative decarboxylation of pyruvate catalyzed by the pyruvate dehydrogenase complex (PDH), with the following overall reaction stoichiometry:

$$Pyruvat(Pyr)+CoA+NAD+=acetyl\text{-}CoA+CO2+NADH+H+$$

In cytosol, acetyl-CoA is synthesized via the pyruvate dehydrogenase (PDH) by-pass, involving the enzymes pyruvate decarboxylase (PDC), acetaldehyde dehydrogenase (ALD), and acetyl-CoA synthetase (ACS), with the following overall reaction stoichiometry:

$$Pyr+CoA+ATP+NAD(P)+=acetyl\text{-}CoA+CO2+NAD(P)H+AMP+Ppi+H+.$$

Pyruvate-decarboxylase-negative (Pdc–) mutant of the yeast S. cerevisiae does not have a functional PDH by-pass, and cannot grow on minimal medium with glucose as the sole carbon source due to inability to supply (sufficient) cytosolic acetyl-CoA for growth (Flikweert et al., (1996) Yeast 12:247-57). The PDH by-pass is therefore essential in providing acetyl-CoA in the cytosolic compartment. However, the PDH bypass in yeast is not optimal with respect to the energy balance, as can be seen from the overall reaction stoichiometry: 2 moles of ATP are needed per acetyl-CoA synthesized via the PDH-bypass since in the acetyl-CoA synthetase reaction ATP is hydrolyzed to AMP. In contrast, the mitochondrial pathway via the PDH requires no ATP. The additional ATP requirement of the PDH by-pass can present a problem for synthesizing the product of interest from cytosolic acetyl-CoA precursor, as more carbon source needs to be diverted for ATP generation, via e.g. oxidative phosphorylation and/or substrate phosphorylation (e.g. glycolysis), thereby lowering the overall yield of the product on carbon.

When yeast is metabolically engineered to produce 1-butanol, heterologous biosynthetic genes of 1-butanol can be expressed in the cytosol in yeast cells (WO 2007/041269). In general 1 mole of glucose give rise to 2 moles of acetyl-CoA via glycolysis, which is the precursor of 1 mole of butanol; hence a maximum of 1 mole of butanol can be synthesized per mole of glucose if cell growth and maintenance is not considered. However, when the PDH by-pass is used in combination with butanol biosynthesis, this maximal theoretical yield cannot be achieved due to energy imbalance: whereas 2 moles of ATP are generated per mole of glucose converted in glycolysis, a total of 4 moles (2 times 2 mole) of ATP are needed in the PDH by-pass to form 2 moles of acetyl-CoA, which are converted to 1 mole of butanol. Thus, there is a net shortage of ATP if the PDH by-pass were used to synthesize 1 mole of 1-butanol from 1 mole of glucose.

Thus, there is a need for the identification of possible alternative metabolic routes for producing cytosolic acetyl-CoA in yeast, for the production of acetyl-CoA-derived products, in particular butanol, wherein the PDH by-pass is not required.

Butanol is an important industrial chemical and is suitable as an alternative engine fuel having improved properties over ethanol. Butanol also finds use as a solvent for a wide variety of chemical and textile processes, in the organic synthesis of plastics, as a chemical intermediate and as a solvent in the coating and food and flavor industry. Butanol can be produced from biomass (biobutanol) as well as fossil fuels (petrobutanol).

The chemical synthesis of butanol in one of its isomers can be accomplished by a variety of available methods known in the art (see e.g. Ullmann's Encyclopedia of Industrial Chemistry, 6th edition, 2003, Wiley-VCH Verlag GmbH and Co., Weinheim, Germany, Vol. 5. pp. 716-719). These processes have the disadvantage that they are based on the use of petrochemical derivates, are generally expensive, and are not environmentally friendly.

Biological synthesis of butanol can be achieved by fermentation using the acetone-butanol-ethanol (ABE) process carried out by the bacteria *Clostridium acetobutylicum* or other *Clostridium* species. An important disadvantage of the ABE process, however, is that it results in a mixture of acetone, 1-butanol and ethanol. Moreover, the use of bacteria requires sterile process conditions and generally renders the process susceptible to bacteriophage infection. Yeast cells thus provide a very suitable alternative as described above.

SUMMARY OF THE INVENTION

The present inventors have now identified alternative metabolic routes for increasing the production of cytosolic acetyl-CoA in yeast which can overcome the problems of the PDH by-pass.

One possible route includes the direct conversion of acetaldehyde to acetyl-CoA without ATP consumption, by use of an acetylating acetaldehyde dehydrogenase (E.C. 1.2.1.10) (see FIG. 2, reaction A, ACDH). Another route includes the direct conversion of pyruvate to acetyl-CoA by an enzyme or a multi-enzyme-complex without ATP consumption, for instance, by use of a pyruvate:NADP oxidoreductase (E.C. 1.2.1.51) see FIG. 2, reaction C, PNO). In these two possible routes, the formation of 1 mole of butanol per mole of glucose would result in the formation of 2 moles of ATP. Yet another route includes the conversion of acetate to acetyl-CoA with 1 ATP consumed per acetyl-CoA formed by an alternative enzyme or a combination of enzymes, for instance, by use of acetate:CoA ligase (ADP-forming, E.C. 6.2.1.13), or by use of ATP:acetate phosphotransferase (E.C. 2.7.2.1) in combination with acetyl-CoA:Pi acetyltransferase (E.C. 2.3.1.8). In this route, the formation of 1 mole of butanol per mole of glucose is ATP-balanced, i.e. no ATP will be formed. The present inventors have now found that such an alternative to the PDH by-pass can result in acetyl-CoA synthesis in the cytosol of the yeast, and that such acetyl-CoA can be used biosynthetically to produce higher amounts of desirable fermentation products, such as butanol.

In a first aspect, the present invention provides a method of identifying a heterologous polypeptide having enzymatic activity for converting pyruvate, acetaldehyde or acetate into acetyl-CoA in (the cytosol of) a yeast cell comprising:

providing a mutated yeast cell, wherein said mutation comprises an inactivation of at least one gene of the (PDH) by-pass, selected from the genes encoding the enzymes pyruvate decarboxylase (PDC), acetaldehyde dehydrogenase (ALD), and acetyl-CoA synthetase (ACS);

transforming said mutated yeast cell with an expression vector comprising at least one heterologous nucleotide sequence operably linked to a promoter functional in yeast and said at least one heterologous nucleotide sequence encoding at least one candidate polypeptide having potential enzymatic activity for converting pyruvate, acetaldehyde or acetate into acetyl-CoA;

testing said recombinant mutated yeast cell for its ability to grow on minimal medium containing glucose as sole carbon source, and identifying said candidate polypeptide as a heterologous polypeptide having enzymatic activity for converting pyruvate, acetaldehyde or acetate into acetyl-CoA in (the cytosol of) said yeast cell when growth of said cell is observed.

In a preferred embodiment of said method the yeast cell is a cell of *Saccharomyces cerevisiae* and the heterologous nucleotide sequence is codon (pair) optimized for expression in *Saccharomyces cerevisiae*.

In another preferred embodiment, said mutation comprises an inactivation of the gene for acetyl-CoA synthetase isoform 2 (acs2).

In another preferred embodiment, said at least one candidate polypeptide having enzymatic activity for converting acetaldehyde into acetyl-CoA is a (putative) acetylating acetaldehyde dehydrogenases.

Alternatively, said at least one heterologous polypeptide having enzymatic activity for converting pyruvate, acetaldehyde or acetate into acetyl-CoA in (the cytosol of) a yeast cell may consist of two or more enzymes working together to achieve the desired conversion from pyruvate, acetaldehyde or acetate into acetyl-CoA.

In another aspect, the present invention provides an integration vector for the integration in a yeast genome of a heterologous nucleotide sequence encoding a polypeptide having enzymatic activity for converting pyruvate, acetaldehyde or acetate into acetyl-CoA, and the subsequent expression of the heterologous polypeptide therefrom.

In another aspect, the present invention provides an expression vector expressing heterologous polypeptides in yeast, said expression vector comprising a heterologous nucleotide sequence operably linked to a promoter functional in yeast and said heterologous nucleotide sequence encoding a polypeptide having enzymatic activity for converting pyruvate, acetaldehyde or acetate into acetyl-CoA in (the cytosol of) said yeast cell.

In a preferred embodiment of said vector the polypeptide having enzymatic activity for converting pyruvate, acetaldehyde or acetate into acetyl-CoA is identified by a method according to the present invention as described above.

In another preferred embodiment, said polypeptide is selected from SEQ ID NO: 19, 22, 25, 28 and 52 and functional homologues thereof.

In another preferred embodiment, said expression vector is for expression in *Saccharomyces cerevisiae*, wherein said heterologous nucleotide sequence is codon (pair) optimized for expression in *Saccharomyces cerevisiae*.

In another preferred embodiment, said heterologous nucleotide sequence is selected from SEQ ID NO: 20, 23, 26 and 29.

In another aspect, the present invention provides a recombinant yeast cell comprising the expression vector of the present invention as described above.

In a preferred embodiment, the recombinant yeast cell further comprises an inactivation of at least one gene of the (PDH) by-pass, selected from the genes encoding the enzymes pyruvate decarboxylase (PDC), acetaldehyde dehydrogenase (ALD), and acetyl-CoA synthetase (ACS).

Preferably, a yeast cell according to be present invention comprises an inactivation of a gene encoding an acetyl-CoA synthase.

In another preferred embodiment, the recombinant yeast cell further comprises an inactivation of a gene (nucleotide sequence) encoding an enzyme capable of catalysing the conversion of acetaldehyde to ethanol, preferably a gene encoding an alcohol dehydrogenase.

As used herein, inactivation of a gene (nucleotide sequence) encoding an enzyme may be achieved by mutation, deletion or disruption of (part of) a gene or nucleotide sequence encoding an enzyme.

Preferably a yeast cell according to the present invention shows growth on minimal medium containing glucose as sole carbon source.

In another preferred embodiment of a yeast cell of the invention, said yeast cell further comprises one or more introduced genes encoding a recombinant pathway for the formation of 1-butanol from cytosolic acetyl-CoA. Suitable recombinant pathways from acetyl-CoA to 1-butanol are known in the art. Such pathways are for instance known from WO 2007/041269. Preferably said one or more introduced genes encode enzymes that produce acetoacetyl-CoA, 3-hydroxybutyryl-CoA, crotonyl-CoA, butyryl-CoA, butyl-aldehyde and/or 1-butanol. Said enzymes can be:

acetyl-CoA acetyltransferase (E.C. 2.3.1.9 [Enzyme Nomenclature 1992, Academic Press, San Diego]; although, enzyme's with a broader substrate range (E.C. 2.3.1.16) will be functional as well), which converts 2 moles of acetyl-CoA to acetoacetyl-CoA;

NADH-dependent or NADPH-dependent 3-hydroxybutyryl-CoA dehydrogenase E.C. 1.1.1.35 or E.C. 1.1.1.30, resp. E.C. 1.1.1.157 or E.C. 1.1.1.36), which converts acetoacetyl-CoA to 3-hydroxybutyryl-CoA;

3-hydroxybutyryl-CoA dehydratase (also named crotonase; E.C. 4.2.1.17 or E.C. 4.2.1.55), which converts 3-hydroxybutyryl-CoA to crotonyl-CoA;

NADH-dependent or NADPH-dependent butyryl-CoA dehydrogenase (E.C. 1.3.1.44 resp. E.C. 1.3.1.38 or E.C.1.3.99.2), which converts crotonyl-CoA to butyryl-CoA;

monofunctional NADH-dependent or NADPH-dependent aldehyde dehydrogenase (E.C. 1.2.1.10, or 1.2.1.57), which converts butyryl-CoA to butyraldehyde, and NADH-dependent or NADPH-dependent butanol dehydrogenase (E.C. 1.1.1.-), which converts butylaldehyde to 1-butanol, or bifunctional NADH-dependent or NADPH-dependent aldehyde/alcohol dehydrogenase (E.C. 1.1.1.1.11.2.1.10), which converts butyryl-CoA to 1-butanol via butyraldehyde In another preferred embodiment of the invention a yeast cell is a *Saccharomyces cerevisiae*.

In another aspect, the present invention provides a method of producing butanol, comprising the steps of fermenting a suitable carbon substrate with a yeast cell according to the present invention and recovering the butanol produced during said fermentation.

DETAILED DESCRIPTION OF THE INVENTION

Definitions

Figure 1:
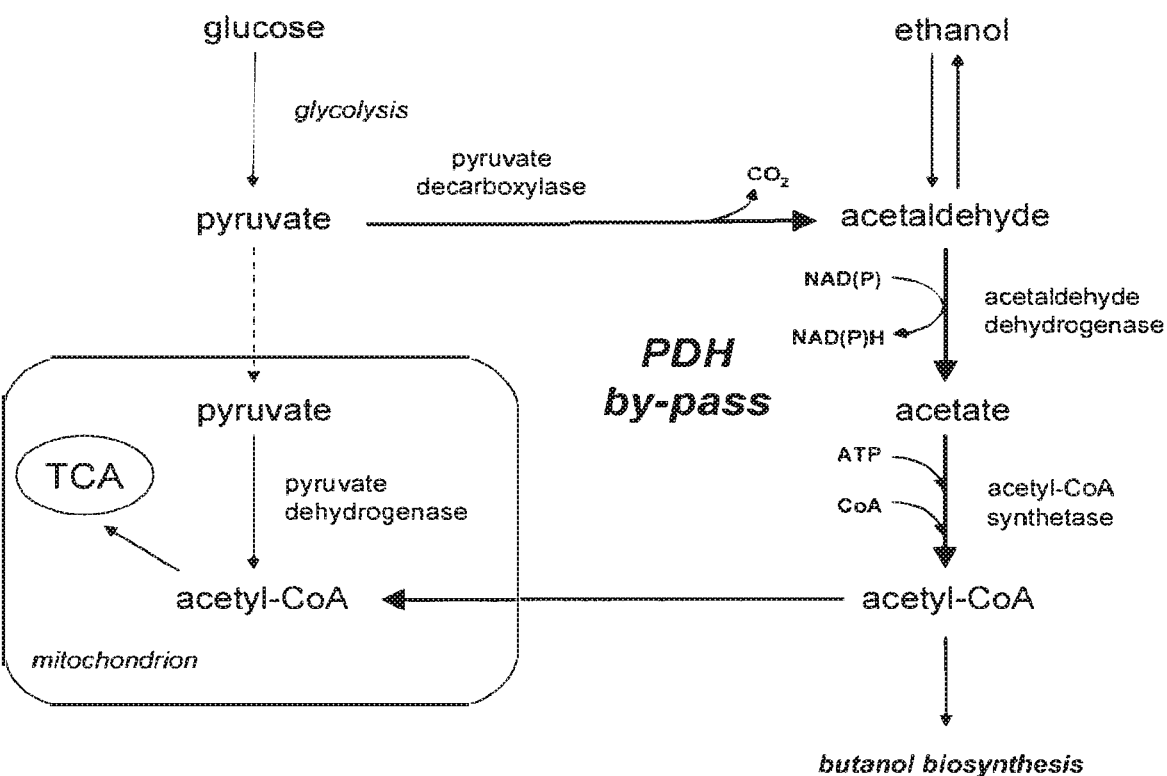
FIG. 1 is a schematic presentation of the PDH by-pass showing the enzymes pyruvate decarboxylase (PDC: E.C. 4.1.1.1), acetaldehyde dehydrogenase (ALD; E.C. 1.2.1.3, E.C. 1.2.1.4 and E.C. 1.2.1.5), and acetyl-CoA synthetase (ACS; E.C. 6.2.1.1).

The term "butanol" refers to n-butanol, or 1-butanol.

The term "yeast" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well known species.

The term "recombinant yeast" as used herein, is defined as a cell which contains a nucleotide sequence and/or protein, or is transformed or genetically modified with a nucleotide sequence that does not naturally occur in the yeast, or it contains additional copy or copies of an endogenous nucleic acid sequence (or protein), or it contains a mutation, deletion or disruption of an endogenous nucleic acid sequence.

The term "mutated" as used herein regarding proteins or polypeptides means that at least one amino acid in the wild-type or naturally occurring protein or polypeptide sequence has been replaced with a different amino acid, or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning—A Laboratory Manual. 2nd ed., Vol. 1-3 (1989). The term "mutated" as used herein regarding genes means that at least one nucleotide in the nucleotide sequence of that gene or a regulatory sequence thereof, has been replaced with a different nucleotide, or has been deleted from the sequence via mutagenesis, resulting so in the transcription of a non-functional protein sequence or the knock-out of that gene.

The term "gene", as used herein, refers to a nucleic acid sequence containing a template for a nucleic acid polymerase, in eukaryotes, RNA polymerase II. Genes are transcribed into mRNAs that are then translated into protein.

The term pyruvate dehydrogenase (PDH) by-pass refers to the enzymatic cascade form pyruvate to acetyl-CoA in the cytosol of yeast, and which consists of the following enzymes: pyruvate decarboxylase (PDC; E.C. 4.1.1.1) converting pyruvate into acetaldehyde; acetaldehyde dehydrogenase (ALD; E.C. 1.2.1.3, E.C. 1.2.1.4 and E.C. 1.2.1.5), converting acetaldehyde into acetate; and acetyl-CoA synthetase (ACS; E.C. 6.2.1.1), converting acetate into acetyl-CoA.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

Sequence identity is herein defined as a relationship between two or more amino acid (polypeptide or protein) sequences or two or more nucleic acid (polynucleotide) sequences, as determined by comparing the sequences. Usually, sequence identities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity are codified in publicly available computer programs. Preferred computer program methods to determine identity and similarity between two sequences include BLASTP, BLASTN (Altschul, S. F. et al., J. Mol. Biol. 215:403-410 (1990), publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. If a promoter is an inducible promoter, then the rate of transcription increases in response to an inducing agent.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e., operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleotide sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e., operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

As used herein, the term "operably linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

By "host cell" is meant a cell which contains a vector and supports the replication and/or expression of the vector. Host cells may be prokaryotic cells such as E. coli, or eukaryotic cells such as yeast, insect, amphibian, or mammalian cells. Preferably, host cells are cells of the order of Actinomycetales, most preferably yeast cells, most preferably cells of Saccharomyces cerevisiae.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

The term "oligonucleotide" refers to a short sequence of nucleotide monomers (usually 6 to 100 nucleotides) joined by phosphorous linkages (e.g., phosphodiester, alkyl and aryl-phosphate, phosphorothioate, phosphotriester), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "polynucleotide" as used herein refers to a polymeric form of nucleotides of any length, either ribo-nucleotides or deoxyribonucleotides. Thus, this term includes double- and single-stranded DNA and RNA.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; or (3) does not occur in nature.

The term "minimal medium" as used herein refers to a chemically defined medium, which includes only the nutrients that are required by the cells to survive and proliferate in culture. Typically, minimal medium is free of biological extracts, e. g., growth factors, serum, pituitary extract, or other substances, which are not necessary to support the survival and proliferation of a cell population in culture. For example, minimal medium generally includes as essential substances: at least one carbon source, such as glucose; at least one nitrogen source, such as ammonium, ammonium sulfate, ammonium chloride, ammonium nitrate or urea; inorganic salts, such as dipotassium hydrogenphosphate, potassium dihydrogen-phosphate and magnesium sulfate; and other nutrients, such as biotin and vitamins.

Description of the Preferred Embodiments

A method of the present invention provides a method for identifying heterologous enzymes capable of producing acetyl-CoA in the cytosol of a yeast cell.

The heterologous enzyme may produce the acetyl-CoA using pyruvate, acetaldehyde or acetate as a substrate, preferably in a single conversion step. Preferably, the heterologous enzyme produces the acetyl-CoA from acetaldehyde. An enzyme capable of catalyzing said reaction is acetylating acetaldehyde dehydrogenase (acdh; E.C. 1.2.1.10) also referred to as acetadehyde:NAD+ oxidoreductase (CoA-acetylating). The conversion of acetaldehyde into acetyl-CoA by acetylating acetaldehyde dehydrogenase is reversible and runs in the direction of acetyl-CoA when acetaldehyde accumulates in the cytosol. Such an accumulation may for instance be achieved by deletion of alcohol dehydrogenase (adh: E.C. 1.1.1.1).

The heterologous enzyme may also produce the acetyl-CoA from pyruvate. An enzyme capable of catalyzing said reaction is a pyruvate:NADP oxidoreductase (pno; E.C. 1.2.1.51). The reaction is stoichiometrically identical to the mitochondrial pyruvate dehydrogenase except that pno uses NADPH as a cofactor as compared to PDH that uses NADH. Compared to acdh, an important disadvantage of the pno enzyme system is that pno is oxygen sensitive, and that it is a large multimeric enzyme, and hence, its successful genetic incorporation (a 5-6 kb gene) is much more difficult than that of acdh. For this reason, the use of acdh is preferred in embodiments of the present invention.

An important feature of a test cell capable of revealing the desired enzymatic activity of a test polypeptide is that the cell is prototrophic as a result of the introduced polypeptide. With this, it is meant that the cell's nutritional requirements do not exceed those of the corresponding wild-type strain and that it will proliferate on minimal medium (in contrast to the auxotroph). In fact, the production of acetyl-CoA as supported by the test polypeptide will cancel the effect of the deletion of said at least one gene of the PDH by-pass, caused by the deletion of the gene for pyruvate decarboxylase (pdc; E.C. 4.1.1.1), acetaldehyde dehydrogenase (aid; E.C. 1.2.1.3. E.C. 1.2.1.4 or E.C. 1.2.1.5), or acetyl-CoA synthetase (acs; E.C. 6.2.1.1). Such complementation assays are well known in the art. In aspects of the present invention the assay is used to identify suitable sources of heterologous enzymes capable of sustaining cytosolic acetyl-CoA production in yeast cells.

The complementation assay is based on the provision of alternative routes to overcome the deleted enzyme activity of the PDH by-pass. Methods for effecting deletion of genes in yeast are well known in the art, and can for instance be achieved by oligonucleotide-mediated mutagenesis. Good results may be obtained with the plasmid pUG6 carrying the loxP-kanMX-loxP gene disruption cassette (Giildener et al. [1996] Nucleic Acids Res. 24(13):2519-24; GenPept accession no. P30114). Thus, the skilled person will be able to provide a yeast strain having a deleted acetaldehyde dehydrogenase and/or acetyl-CoA synthetase gene for blocking the PDH by-pass therein.

Saccharomyces cerevisiae comprises two acetyl-CoA synthetase isoforms, Acs1p and Acs2p. Both are the nuclear source of acetyl-CoA for histone acetylation. The production of cytosolic acetyl-CoA is also required for lipid production. Acs activity is essential, since an acs1 acs2 double null mutant is non-viable. An acs1 null mutant can grow with ethanol as the sole carbon source. The mutated yeast cell used in aspects of the present invention preferably has an inactivation of the acs2 gene.

Saccharomyces cerevisiae mutants carrying an inactivation of the acs2 gene are not able to grow on glucose as sole carbon source, because ACS1 is repressed and the protein is actively degraded. Complementation of such a delta acs2 mutant with a plasmid based acs gene will restore the cell's ability to grow on glucose as single carbon source. In addition, growth of such a mutant is complemented by the expression of genes supporting alternative routes for the production of sufficient cytosolic acetyl-CoA. Thus, transformation of the delta acs2 mutant with a plasmid from which a functional (heterologous) acdh or pno can be expressed will restore the mutant's ability to grow on glucose as sole carbon source. It should be understood that in addition to the removal of the ACS2 locus, one may also remove the ACS1 locus. Although it is believed that this may in some instances prevent the occurrence of revertants (mutations in the ACS1 locus leading to reversion of the delta acs2 phenotype), this was however not found to be essential. Double mutants (acs1/acs2Δ strains) would be wholly dependent on the introduced acdh or pno gene for the production of cytosolic acetyl-CoA.

An important advantage of a complementation assay of the present invention is that it can be performed as a plate screening assay wherein successful complementation is observed as colony growth. This is much faster than experiments that require the analysis for the production of a desired metabolic product.

For complementation of the mutation, the yeast cell having the inactivated aid and/or acs gene is then transformed with a suitable expression vector comprising a nucleotide sequence of a heterologous test polypeptide.

Yeast expression vectors are widely available from a variety of commercial suppliers. To date, functional complementation of yeast mutations by foreign homologues has become a standard practice in engineering of Saccharomyces cerevisiae. Suitable expression vectors for heterologous gene expression may be based on artificial, inducible promoters such as the GAL promoter, but is preferably based on constitutive promotors such as the TDH3 promoter. Suitable systems are exemplified in the examples below. In certain production systems, the use of an inducible promotor may be preferred, as it would allow for temporal separation of stages for biomass production (promotor not induced) and fermentation product production (promoter induced). In another highly preferred embodiment in certain production systems, the vector is in integration vector for stable integrating the heterologous genes in the genome of the yeast production strain.

In order to achieve optimal expression in yeast, the codon (pair) usage of the heterologous gene may be optimized by using any one of a variety of synthetic gene design software packages, for instance GeneOptimizer® from Geneart AG (Regensburg, Germany) for codon usage optimization or codon pair usage optimization as described in WO2008/000632. Such adaptation of codon usage ensures that the heterologous genes, which are for instance of bacterial origin, are effectively processed by the yeast transcription and translation machinery. Optimization of codon pair usage will result in enhanced protein expression in the yeast cell.

The optimized sequences may for instance be cloned into a high copy yeast expression plasmid, operably linked to a (preferably constitutive) promoter functional in yeast. Good results have been obtained with the plasmid YEplac112 (2μ TRP1) (Gietz & Sugino [1988] Gene 74(2):527-34).

Heterologous genes that encode a candidate polypeptide having potential enzymatic activity for converting pyruvate, acetaldehyde or acetate into acetyl-CoA may be identified in silico. Suitable enzymes described as possessing the capacity to convert acetaldehyde into acetyl-CoA are acetylating acetaldehyde dehydrogenases (E.C. 1.2.1.10). The nucleotide and amino acid sequences of over 200 of these enzymes from a variety of microbial origins are described in various databases (e.g. the KEGG (Kyoto Encyclopedia of Genes and Genomes) database).

The present inventors have selected several acetylating acetaldehyde dehydrogenases and tested these in the delta acs2 mutant-based assay system of the present invention. Many of these, though not all, were functional in S. cerevisiae when codon pair usage was optimized.

Functional homologues to these proteins can also be used in aspects of the present invention. The term "functional homologues" as used herein refers to a protein comprising the amino acid sequence of SEQ ID NO:19, 22, 25 or the acetaldehyde dehydrogenase part of SEQ ID NOs: 28 and 52 in which one or more amino adds are substituted, deleted, added, and/or inserted, and which protein has the same enzymatic functionality for substrate conversion, for instance an acetylating acetaldehyde dehydrogenase homologue is capable of converting acetaldehyde into acetyl-CoA. This functionality may be tested by use of an assay system comprising a recombinant yeast cell comprising an expression vector for the expression of the homologue in yeast, said expression vector comprising a heterologous nucleotide sequence operably linked to a promoter functional in yeast and said heterologous nucleotide sequence encoding the homologous polypeptide of which enzymatic activity for converting pyruvate, acetaldehyde or acetate into acetyl CoA in (the cytosol of) said yeast cell is to be tested, and performing a method for identifying a heterologous polypeptide having enzymatic activity for converting pyruvate, acetaldehyde or acetate into acetyl-CoA in (the cytosol of) a yeast cell as described herein using said assay system. Candidate homologues may be identified by using in silico similarity analyses. A detailed example of such an analysis is described in Example 2 below. The skilled person will be able to derive therefrom how suitable candidate homologues may be found and, optionally upon codon(pair) optimization, will be able to test the required functionality of such candidate homologues using the assay system of the present invention as described above. A suitable homologue represents a polypeptide having an amino acid sequence identity to an acetylating acetaldehyde dehydrogenase of more than 50%, preferably more than 60%, more preferably more than 70%, 80%, 90% or more, for instance having such an amino acid sequence identity to SEQ ID NOs: 19, 22, 25, or the acetaldehyde dehydrogenase part of SEQ ID NOs:28 and 52 and having the required enzymatic functionality for converting acetaldehyde into acetyl-CoA. Similarly, enzymes described for the direct conversion of pyruvate into acetyl-CoA and the functional homologues thereof, as well as enzymes described for the conversion of acetate to acetyl-CoA and the functional homologues thereof, can also be used, similar as described for acetylating acetaldehyde dehydrogenase above.

A method of the present invention further comprises the step of testing the ability of the mutated and test-protein transformed yeast cell to grow on minimal medium containing glucose as sole carbon source. As stated earlier, this may suitably occur on solid (agar) media in Petri dishes (plates) where growth can be observed as growth of a colony, however, liquid media are equally suitable and growth may be detected by turbidity. Other methods for determining growth of the mutated and test-protein transformed yeast cell on minimal medium containing glucose as sole carbon source may also be used.

When the mutated and test-protein-transformed yeast cell is capable of growth on minimal medium with glucose, the candidate polypeptide is successfully identified as a heterologous polypeptide having enzymatic activity for converting pyruvate, acetaldehyde or acetate into acetyl-CoA in (the cytosol of) said yeast cell. Growth may suitably be observed as colony formation on solid growth media, in particular minimal medium containing glucose.

An expression vector for the expression of heterologous polypeptides in yeast, according to the present invention may be any expression vector suitable for transforming yeast. Innumerable examples are available in the art that can suitably be used to express heterologous nucleotide sequences in yeast. A very suitable vector in aspects of the invention is a plasmid. A highly preferred plasmid is YEplac112PtdhTadh (SEQ ID NO:40).

Generally, the heterologous nucleotide sequence encoding the polypeptide having enzymatic activity for converting pyruvate, acetaldehyde or acetate into acetyl CoA in (the cytosol of) said yeast cell, will be placed under control of a promoter functional in yeast. Preferably the promoter is a constitutive promoter. The promoter on plasmid YEplac112PtdhTadh is the TDH3 promoter.

The heterologous nucleotide sequences incorporated in the expression vector of the present invention may be any pno, acdh or other enzyme capable of converting pyruvate, acetaldehyde or acetate (respectively) into acetyl-CoA in the cytosol of the yeast. Preferred nucleotide sequences are those as identified herein, namely the nucleotide sequences encoding:

the ethanolamine utilization protein EutE from *E. coli* HS (nucleotide sequences with SEQ ID NO:18);

the hypothetical protein Lin1129 from *Listeria innocua* similar to ethanolamine utilization protein EutE. (nucleotide sequences with SEQ ID NO:21)

the acetaldehyde dehydrogenase EDK33116 from *Clostridium kluyver* DSM 555 (nucleotide sequences with SEQ ID NO:24); and the adhE homologue of *S. aureus* (nucleotide sequences with SEQ ID NO:27) encoding a bifunctional acetaldehyde/alcohol dehydrogenase in *Staphylococcus*

*aureus* subsp. *aureus* N315, or the acetaldehyde dehydrogenase functional part thereof.

the adhE homologue of *Piromyces* sp. E2 (nucleotide sequence SEQ ID NO: 51) encoding a bifunctional acetaldehyde/alcohol dehydrogenase, or the acetaldehyde dehydrogenase part thereof.

Also suitable are functional homologues of these nucleotide sequences, or of the polypeptides that they encode. With this term is meant that a nucleic acid sequence having more than 80%, 90% or 95% sequence identity with the nucleotide sequences encoding the above acdh enzymes, or having more than 50%, preferably more than 60%, 70%, 80%, 90%, or 95% sequence identity with the amino acid sequence of the above acdh enzymes, with the proviso that the polypeptides encoded by the homologous sequences exhibit functional enzymatic acdh activity.

As stated above, these nucleotide sequences can be optimized for expression in *Saccharomyces cerevisiae* by optimization of codon pair usage well known in the art. Codon pair optimized sequences for the SEQ ID NO:18, 21, 24, and 27 are provided in SEQ ID N020, 23, 26, and 29, respectively.

The expression vector of the invention may be used to transform a yeast cell. Methods of transformation include electroporation, glass bead and biolistic a transformation, all of which are well known in the art and for instance described in Sambrook et al., Molecular Cloning-A Laboratory Manual, 2nd ed., Vol. 1-3 (1989).

A yeast cell according to the present invention comprises a heterologous nucleotide sequence encoding a polypeptide having enzymatic activity for converting pyruvate, acetaldehyde or acetate into acetyl-CoA in (the cytosol of) said yeast cell. Preferably, a yeast cell of the invention comprises a heterologous acdh or pno. The advantage of such a yeast cell is that it can produce acetyl-CoA by a metabolic route wherein the PDH by-pass is not required. This is energetically more favourable under anaerobic conditions, and may form the basis of any biological synthesis process using yeast cells under anaerobic conditions where acetyl-CoA is an intermediate. In addition to comprising the heterologous acdh or pno, the yeast cell of the invention may comprise various gene deletions or gene supplementations, depending on the intended use of the yeast.

Preferably a yeast cell according to the present invention comprises an inactivation of a nucleotide sequence (gene) encoding an enzyme capable of catalysing the conversion of acetaldehyde to ethanol, preferably an alcohol dehydrogenase, for instance to optimize acetaldehyde accumulation in the yeast cell.

If used in a method of screening for heterologous enzymes according to a method of the invention, the yeast cell comprises a deletion of at least one gene of the (PDH) by-pass, selected from the genes encoding the enzymes pyruvate decarboxylase (PDC), acetaldehyde dehydrogenase (ALD), and acetyl-CoA synthetase (ACS), preferably acetyl-CoA synthetase, most preferably acs2.

Figure 2:
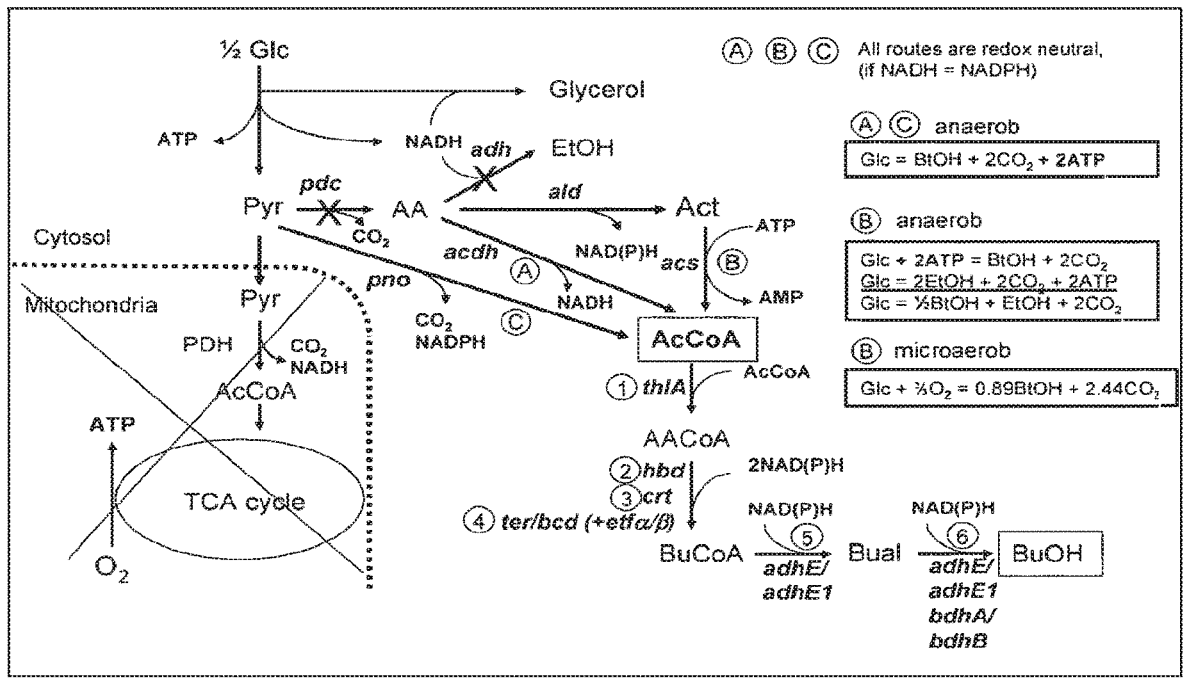
FIG. 2 shows a schematic metabolic route for butanol production in *Saccharomyces cerevisiae*. Reactions 1-6 are the butanol biosynthesis steps from *Clostridium acetobutylicum* introduced in yeast. A, B, and C indicate alternative reactions for acetyl-CoA biosynthesis in the cytosol. B indicates part of the pyruvate dehydrogenase by-pass (pdc, aid and acs), the natural source of cytosolic acetyl-CoA in yeast. Glc, glucose; EtOH, ethanol; Pyr, Pyruvate; AA, acetaldehyde; ACT, acetate; AcCoA, acetyl-CoA; AACoA, acetoacetyl-CoA; BuCoA, butyryl-CoA; Bual, butylaldehyde; BuOH, butanol; NAD(P)(H), nicotinamide adenine dinucleotide (phosphate) (in reduced form); ATP, adenosine triphosphate; AMP, adenosine monophosphate; TCA cycle, tricarboxylic acid cycle; PDH, pyruvate dehydrogenase; pdc, pyruvate decarboxylase; adh, alcohol dehydrogenase; acdh, acetylating acetaldehyde dehydrogenase; aid, acetaldehyde dehydrogenase; acs, acetyl-CoA synthetase; pno, pyruvate:NADP oxidoreductase. Enzymatic conversions indicated by reaction 1-6 indicate a heterologous butanol pathway from *Clostridium acetobutylicum*: thlB (or ThL) encoding acetyl-CoA acetyltransferase or thiolase [E.C. 2.3.1.9](SEQ ID NO:30); hbd, 3-hydroxybutyryl-CoA dehydrogenase [E.C.1.1.1.157](SEQ ID NO:31); crt, 3-hydroxy-butyryl-CoA dehydratase [E.C.4.2.1.55](SEQ ID NO:32); ter, trans-enoyl CoA reductase; bcd, butyryl-CoA dehydrogenase [E.C.1.3.99.2](SEQ ID NO:33); etf ap, heterodimeric electron transfer flavoprotein (elf a and etf 3, SEQ ID NO:38 and SEQ ID NO:39, respectively); adhE/adhE1, aldehyde/alcohol dehydrogenase E and E1 [E.C. 1.1.1.1/ 1.2.1.10](SEQ ID NO:34 and 35, respectively): bdhA/bdhB, NAD(P)H-dependent butanol dehydrogenase A and B [E.C.: 1.1.1.-](SEQ ID NO:36 and 37, respectively).
Figure 3:
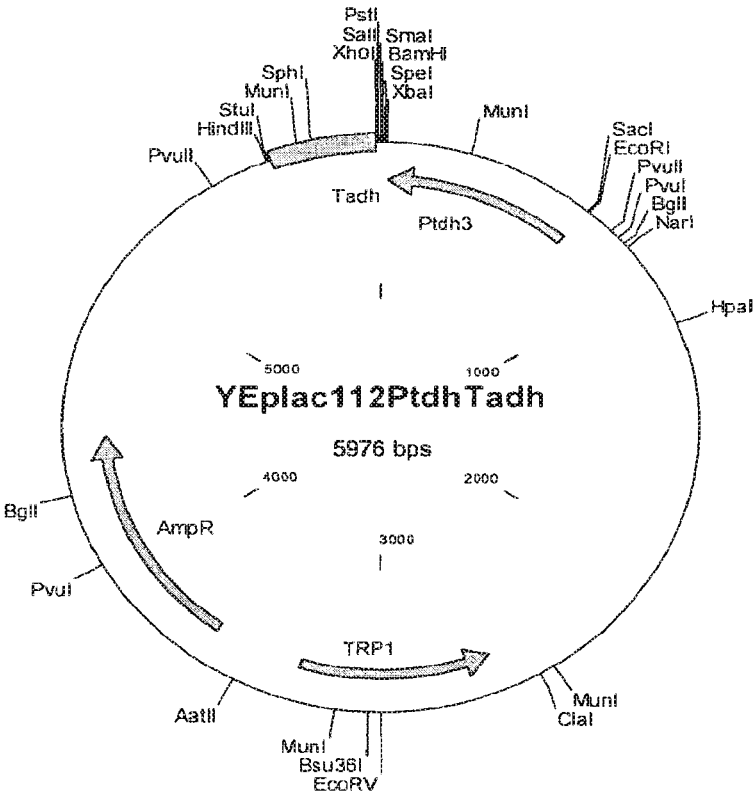
FIG. 3 shows the map of plasmid YEplac112PtdhTadh. The sequence of this plasmid is provided in SEQ ID NO:40.

If used in a method of producing a fermentation product, the yeast cell may optionally comprise a number of (heterologous) gene supplementations supporting the metabolic pathway from acetyl-CoA to said butanol. Such a pathway may consist only of heterologous gene products, or may make use of a mixture of heterologous and endogenous gene products. In the event the fermentation product is butanol, use can be made of a yeast comprising genes encoding enzymes for the butanol pathway of e.g. *Clostridium acetobutylicum* as described herein and in FIG. 2. In the event the yeast cell according to the present invention comprises genes encoding enzymes for butanol production, the yeast preferably comprises a nucleotide sequence encoding a butyryl-CoA dehydrogenase and at least one nucleotide sequence encoding a heterologous electron transfer flavo-protein (ETF). It was found that a yeast cell comprising an ETF in addition to genes of the butanol pathway produces an increased amount of butanol.

A heterologous electron transfer flavoprotein in the eukaryotic cell according to the present invention may be a single protein or the ETF may comprise two or more subunits, for instance an alpha and a beta subunit. Preferably the ETF comprises an ETF alpha (SEQ ID NO: 38) and an ETF beta (SEQ ID NO: 39). The electron transfer flavopro-tein may be derived from any suitable origin. Preferably, the ETF is derived from the same origin as the butyryl-CoA dehydrogenase. Preferably, the ETF is derived from pro-karyotic origin preferably from a *Clostridium* sp., preferably a *Clostridium acetobutylicum* or a *Clostridium beijerinckii*.

A method for producing a fermentation product according to the present invention, preferably comprises growing a yeast under anaerobic conditions on a suitable carbon and energy source. Suitable sources of carbon and energy are C5 and C6 sugars (monosaccharides) such as glucose and polysaccharides such as starch. Other raw materials such as sugarcane, maize, wheat, barley, sugarbeets, rapeseed, and sunflower are also suitable. In some instances the raw material may be pre-digested by enzymatic treatment. Most preferably the carbon source is lignocellulose, which is composed of mainly cellulose, hemicellulose, pectin, and lignin. Lignocellulose is found, for example, in the stems, leaves, hulls, husks, and cobs of plants. Hydrolysis of these polymers by specific enzymatic treatment releases a mixture of neutral sugars including glucose, xylose, mannose, galac-tose, and arabinose. Lignocellulosic materials, such as wood, herbaceous material, agricultural residues, corn fiber, waste paper, pulp and paper mill residues can be used to produce butanol. Hydrolysing enzymes are for instance beta-linked glucans for the hydrolysis of cellulose (these enzymes include endoglucanases, cellobiohydrolases, glu-cohydrolases and beta-glucosidases); beta-glucosidases hydrolyze cellobiose; endo-acting and exo-acting hemicel-lulases and cellobiases for hydrolysis of hemicellulose, and acetylesterases and esterases that hydrolyze lignin glycoside bonds. These and other methods for hydrolysis of lignocel-lulose are well known in the art.

Variations and modifications of the embodiments dis-closed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention will now be illustrated by way of the following non-limiting examples.

EXAMPLES

The following examples illustrate the provision of a strain of *Saccharomyces cerevisiae* useful in assays and methods of the present invention, for instance in methods for iden-tifying heterologous enzymes capable of forming cytosolic acetyl-CoA in *S. cerevisiae*. Such methods are useful in the identification of routes/enzymes which allow the cytosolic supply of acetyl-CoA in *S. cerevisiae* under anaerobic con-ditions.

In order to enhance cytosolic acetyl-CoA formation in our butanol production strain, a selection method was set up to identify heterologous enzymes forming cytosolic acetyl-CoA in *S. cerevisiae*. The test system is based on a delta acs2 yeast mutant deficient in cytosolic acetyl-CoA biosynthesis on glucose, such a strain is unable to grow on glucose as sole carbon source unless cytosolic acetyl-CoA formation is complemented. Complementation studies in such a strain can reveal which heterologous enzymes are suitable for use in butanol producing strains of *Saccharomyces cerevisiae*.

Acetylating acetaldehyde dehydrogenase was identified to be a good candidate for cytosolic acetyl-CoA supply over the homologous PDH by-pass because no ATP is dissipated. Twelve putative acetylating acetaldehyde dehydrogenases, identified based on sequence homology, were synthesized and checked for complementation of the delta acs2 yeast.

The codon pair optimized genes of the eutE homologues of *E. coli*, *L. innocua* and *C. kluyveri* and the adhE homo-logue of *S. aureus* were able to complement the acs2 yeast mutants (4 out of 7), resulting in growth of the acs2Δ *S. cerevisiae* host. The aim is to improve butanol biosynthesis in yeast by expression of one or more genes so identified.

In order to test if these heterologous routes for cytosolic acetyl-CoA supply work in *S. cerevisiae*, a screening system was developed based on *Saccharomyces cerevisiae* mutants carrying a deletion of the acs2 gene. These cells are not able to grow on glucose as sole carbon source unless the delta acs2 mutant is complemented with a plasmid based acs gene or complemented with the expression of any other gene generating sufficient cytosolic acetyl-CoA. So if it were to be transformed with a plasmid leading to active expression of acdh or pno, such a mutant should be able to grow again with glucose as single carbon source. The complementation studies were performed on plates. The following experi-ments were performed to set up and evaluate the test system.

Example 1

Construction of Delta Acs2 Strain

The *S. cerevisae* acs2 deleted strain (acs2Δ strain) was produced by first performing a PCR on plasmid pUG6 (Güldener et al., 1996. supra) with the following oligonucle-otides:

```
5'acs2::Kanlox
                                    (SEQ ID NO: 1)
5'-tacacaaacagaatacaggaaagtaaatcaatacaataataaaac
agctgaagcttcgtacgc-3'

3'acs2::Kanlox
                                    (SEQ ID NO: 2)
5'-tctcattacgaaatttttctcatttaagttatttctttttttgag
gcataggccactagtggatctg-3'.
```

The resulting 1.4 kb fragment, containing the KanMX marker which confers resistance to G418, was used to transform *S. cerevisiae* CEN.PK113-3C (MATA trp1-289). After transformation the strain was plated on YPD (10 g l$^{-1}$ yeast extract (BD Difco), 20 g l$^{-1}$ peptone (BD Difco)), 10 g l$^{-1}$ glucose) with 200 mg/ml Geneticin (G418). In resistant transformants, correct integration was verified by PCR using oligonucleotides:

```
5'ACS2:
                                    (SEQ ID NO: 3)
5'-gatattcggtagccqattcc-3'

3'ACS2:
                                    (SEQ ID NO: 4)
5'-ccgtaaccttctcgtaatgc-3'

ACS2internal:
                                    (SEQ ID NO: 5)
5'-cggattcgtcatcagcttca-3'

KanA:
                                    (SEQ ID NO: 6)
5'-cgcacgtcaagactgtcaag-3'

KanB:
                                    (SEQ ID NO: 7)
5'-tcgtatgtgaatgctggtcg-3'
```

The phenotype was verified by testing for growth on YP with 1% glucose (YPD) or 1% ethanol+1% glycerol (YPEG) as the carbon source.

One transformant that had the correct PCR bands and did not grow on YP with glucose, but did grow on with YP with ethanol and glycerol as the carbon sources, was picked and named RWB060 (MATA trp1-289 acs2::Kanlox).

Example 2

In Silico Identification of Putative Acetylating Acetaldehyde Dehydrogenases for Direct Conversion of Acetaldehyde to Acetyl-CoA Enzymes described for the conversion of acetaldehyde to acetyl-CoA are the so-called acetylating acetaldehyde dehydrogenases (ACDH) (E.C. 1.2.1.10) catalysing the following reaction:

$$\text{Acetaldehyde (AA)}+\text{NAD}^+ + \text{CoA} \Leftrightarrow \text{Acetyl-CoA} + \text{NADH} + \text{H}^+$$

From literature four types of proteins have been described that have this activity:

1) Bifunctional proteins that catalyze the reversible conversion of acetyl-CoA to acetaldehyde, and the subsequent reversible conversion of acetaldehyde to ethanol. An example of this type of proteins is the AdhE protein in *E. coli* (GenBank No: NP_415757). AdhE appears to be the evolutionary product of a gene fusion. The NH$_2$-terminal region of the AdhE protein is highly homologous to aldehyde:NAD$^+$ oxidoreductases, whereas the COOH-terminal region is homologous to a family of Fe$^{2+}$-dependent ethanol:NAD$^+$ oxidoreductases (Membrillo-Hernández et al., (2000) J. Biol. Chem. 275: 33869-33875). The *E. coli* AdhE is subject to metal-catalyzed oxidation and therefore oxygen-sensitive (Tamarit et al. (1998) J. Biol. Chem. 273:3027-32).

2) Proteins that catalyze the reversible conversion of acetyl-CoA to acetaldehyde in strictly or facultative anaerobic micro-organisms but do not possess alcohol dehydrogenase activity. An example of this type of proteins has been reported in *Clostridium kluyveri* (Smith et al. (1980) Arch. Biochem. Biophys. 203: 663-675). An acetylating acetaldehyde dehydrogenase has been annotated in the genome of *Clostridium kluyveri* DSM 555 (GenBank No: EDK33116). A homologous protein AcdH is identified in the genome of *Lactobacillus plantarum* (GenBank No: NP_784141). Another example of this type of proteins is the aid gene product in *Clostridium beijerinckii*

NRRL B593 (Toth et al. (1999) Appl. Environ. Microbiol. 65: 4973-4980. GenBank No: AAD31841).

3) Proteins that are involved in ethanolamine catabolism. Ethanolamine can be utilized both as carbon and nitrogen source by many enterobacteria (Stojilkovic et al. (1995) J. Bacteriol. 177: 1357-1366). Ethanolamine is first converted by ethanolamine ammonia lyase to ammonia and acetaldehyde, subsequently, acetaldehyde is converted by acetylating acetaldehyde dehydrogenase to acetyl-CoA. An example of this type of acetylating acetaldehyde dehydrogenase is the EutE protein in *Salmonella typhimurium* (Stojilkovic et al. (1995) J. Bacteriol. 177: 1357-1366, GenBank No: AAL21357). *E. coli* is also able to utilize ethanolamine (Scarlett et al. (1976) J. Gen. Microbiol. 95:173-176) and has an EutE protein (GenBank No: AAG57564) which is homologous to the EutE protein in *S. typhimurium*.

4) Proteins that are part of a bifunctional aldolase-dehydrogenase complex a involved in 4-hydroxy-2-ketovalerate catabolism. Such bifunctional enzymes catalyze the final two steps of the meta-cleavage pathway for catechol, an intermediate in many bacterial species in the degradation of phenols, toluates, naphthalene, biphenyls and other aromatic compounds (Powlowski and Shingler (1994) Biodegradation 5, 219-236). 4-Hydroxy-2-ketovalerate is first converted by 4-hydroxy-2-ketovalerate aldolase to pyruvate and acetaldehyde, subsequently acetaldehyde is converted by acetylating acetaldehyde dehydrogenase to acetyl-CoA. An example of this type of acetylating acetaldehyde dehydrogenase is the DmpF protein in *Pseudomonas* sp CF600 (GenBank No: CAA43226) (Shingler et al. (1992) J. Bacteriol. 174:711-24). *E. coli* has a homologous MphF protein (FerrAndez et al. (1997) J. Bacteriol. 179: 2573-2581, GenBank No: NP_414885) to the DmpF protein in *Pseudomonas* sp. CF600.

Figure 4:
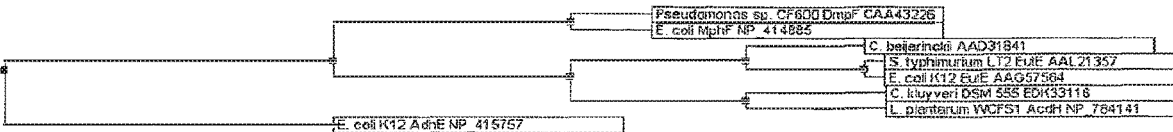
FIG. 4 shows an example of a similarity tree based on amino acid sequences of proteins of the types 1 to 4 as described in Example 2 and indicates the branches.

To identify the protein family members of acetylating acetaldehyde dehydrogenase, the amino acid sequences of the *E. coli* bifunctional AdhE protein (GenBank No: NP_415757), *L. plantarum* AcdH protein (acetylating) (GenBank No: NP_784141), the *E. coli* EutE protein (GenBank No: AAG57564) and the *E. coli* MhpF protein (GenBank No: NP_414885) were each run as a query sequence in a BLASTp search against the GenBank non-redundant protein database using default parameters. Amino acid sequences with an E-value smaller or equal to 1e-20 were extracted. Redundant sequences were removed and the remaining sequences were aligned and a similarity tree was built using Genedata Physolopher protein analyzer software, version 6.5.2. A similarity tree provides information on organism sequence similarity. The tree is created independently of the ClustalW algorithm by pairwise comparison of the amino acid sequences per residue position. At each position, the similarity is rated and summed up to an overall score for each sequence pair. Based on these pairwise scores a hierarchical clustering is performed, which arranges the sequences in a tree. Note that the aid gene product of *C. beijerinckii* (GenBank no: AAD31841) clustered together with the EutE proteins from *E. coli* and *S. typhimurium*. From this similarity tree four major branches could be defined, each branch contains one amino acid sequence that was used as a query for the BLASTp search. FIG. 4 shows an example of such a similarity tree, containing all sequences that are mentioned in this example.

At least one amino acid sequence was selected from each branch for complementation tests in *S. cerevisiae* delta acs2.

Preferably, the selected amino acid 3 sequences have experimental evidence of its biochemical function as acetylating acetaldehyde dehydrogenase. Such evidences can be found in public databases, such as in the BRENDA, UniProt and NCBI Entrez databases.

Example 3

Construction of Expression Plasmids and Complementation Test

To test whether acetylating acetaldehyde dehydrogenases (ACDH) could complement the deletion of ACS2 in *S. cerevisiae*, several genes coding for a (putative) ACDH were chosen from a variety of databases as described above.

To achieve optimal expression in yeast, the codon usage of all genes was adapted by codon pair optimization. These sequences were synthesized at Geneart AG (Regensburg, Germany).

The optimized sequences were cloned into the high copy yeast expression plasmid YEplac112PtdhTadh (SEQ ID NO:40; based on YEplac112 (2p TRP1) (Gietz & Sugino [1988] Gene 74(2):527-34), allowing constitutive expression from the TDH3 promoter.

YEplac112PtdhTadh was made by cloning a KpnI-SacI fragment from p426GPD (Mumberg et al. [1995] Gene, 156(1):119-22), containing the TDH3 promoter and CYC1 terminator, into YEplac112 cut with KpnI-SacI. The resulting plasmid was cut with KpnI and SphI and the ends were made blunt then ligated to give YEplac112TDH. To obtain YEplac112PtdhTadh, YEplac112TDH was cut with PstI-HindIII and ligated to a 345 bp PstI-HindIII PCR fragment containing the ADH1 terminator (Tadh), thus replacing the CYC1 terminator and changing the polylinker between the promoter and terminator. The Tadh PCR fragment was generated using the following oligonucleotides:

```
MCS-5'Tadh:
                                    (SEQ ID NO: 8)
5'-aaggtacctctagactagtcccgggctgcagtcgactcgagcga
atttcttatgatttatgatt-3'

Tadh1-Hind:
                                    (SEQ ID NO: 9)
5'-aggaagcttaggcctgtgtggaagaacgattacaacagg-3'
```

PCR was done with Vent$^R$ DNA polymerase, according to the manufacturer's specifications.

The synthetic constructs containing the ACDH genes were cut with SpeI-PstI and ligated into YEplac112PtdhTadh digested with the same enzymes, resulting in pBOL58 through to pBOL68 and pBOL082. The names of the final plasmids and the genes they contain are given in Table 1.

TABLE 1

Overview on putative acetylating acetaldehyde dehydrogenases tested for complementation of delta acs2 *S. cerevisiae* strain. Genes which resulted in complementation are given in bold. SEQ ID NOs are provided for the DNA sequence of the wild type gene, the protein expressed therefrom, and the codon pair optimized DNA sequence.

| Organisms | Name | Group* | Size (kb) | SEQ ID NO. DNA/ PRT/OPT |
|---|---|---|---|---|
| *Escherichia coli* | adhE | 1 | 2.6 | |
| *Entamoeba histolytica* | adh2 | 1 | 2.6 | 48/50/49 |
| *Staphylococcus aureus* | adhE | 1 | 2.6 | 27/28/29 |
| *Piromyces sp.E2* | adhE | 1 | 2.6 | 51/52 |

TABLE 1-continued

Overview on putative acetylating acetaldehyde dehydrogenases tested for complementation of delta acs2 *S. cerevisiae* strain. Genes which resulted in complementation are given in bold. SEQ ID NOs are provided for the DNA sequence of the wild type gene, the protein expressed therefrom, and the codon pair optimized DNA sequence.

| Organisms | Name | Group* | Size (kb) | SEQ ID NO. DNA/ PRT/OPT |
|---|---|---|---|---|
| *Clostridium kluyveri* | EDK33116 | 2 | 1.5 | 24/25/26 |
| *Lactobacillus plantarum* | acdH | 2 | 1.4 | |
| *Escherichia coli* | EutE | 3 | 1.4 | 18/19/20 |
| *Listeria innocus* | Lin1129 | 3 | 1.4 | 21/22/23 |
| *Pseudomonas putida* | YP 001268189 | 4 | 1.0 | |

*Group refers to the group of proteins having ACDH activity as defined in Example 2. Group 1: similar to bifunctional *E. coli* AdhE (AdhE-type of proteins); group 2; proteins having similarity to *Lactobacillus plantarum* AcdH (AcdH-type of proteins); group 3: similar to *E. coli* EutE (EutE-type of proteins); group 4: similar to *E. coli* MhpF (MhpF-type of proteins).

All plasmids were used to transform the delta acs2 yeast strain RWB060. As negative control, the empty vector YEplac112 was used. Transformants were plated on mineral medium (Verduyn et al. [1992] Yeast 8 (1992), pp. 501-517) containing either 1% glucose (MYD) or 1% ethanol+1% glycerol (MYEG) as single carbon source.

While for all constructs several transformants could be selected on minimal medium with ethanol/glycerol, this was not the case on the glucose containing plates.

TABLE 2

Result of a complementation experiment for putative acetylating acetaldehyde dehydrogenases in delta acs2 *S. cerevisiae* strain RWB060. Genes resulting in complementation are given in bold. MYEG and MYD columns indicate number of transformants on plates MYEG (ethanol/glycerol) and MYG (glucose).

| Organisms | Gene (GenPept accession) | plasmid | MYEG | MYD |
|---|---|---|---|---|
| | none | YEplac112 | 75 | 0 |
| *Escherichia coli* | adhE | pBOL059 | 6 | 0 |
| *Entamoeba histolytica* | adh2 | pBOL061 | 54 | 0 |
| *Staphylococcus aureus* | adhE (BAB41363) | pBOL064 | 36 | 39 |
| *Piromyces sp.E2* | adhE | pBOL139 | 32 | 3 |
| *Clostridium kluyveri* | EDK33116 (EDK33116) | pBOL065 | 21 | 8 |
| *Lactobacillus plantarum* | acdH | pBOL058 | 6 | 0 |
| *Escherichia coli* | EutE(ABV06849) | pBOL066 | 24 | 18 |
| *Listeria innocus* | Lin1129 (CAC96360) | pBOL067 | 28 | 8 |
| *Pseudomonas putida* | YP 001268189 | pBOL068 | 32 | 0 |

On the glucose containing plates, transformants could only be selected for plasmids pBOL64, pBOL065, pBOL66, and pBOL67, not the empty vector. There was also a clear difference in colony size, depending on the plasmid used. While construct pBOL66 (*E. coli* eutE) resulted in biggest colonies, colonies of pBOL67 (*L. innocua* lin1129) appeared a bit smaller and pBOL065 (*C. kluyveri* edk3116) showed smallest colonies. Plasmid pBOL064 (*S. aureus* adhE) and plasmid pBOL139 (*Piromyces* sp. E2, adhE) were done at a later date, so could not be compared directly, Colonies containing pBOL64 seemed to be similar to colonies comprising pBOL066 and colonies comprising pBOL139 seemed to be similar to colonies comprising pBOL065.

To ensure that these results did not arise from spontaneous revertants, transformation experiments were repeated for some of the plasmids, giving the same results. In addition, for almost all plasmids four transformants were selected at random from the MYEG plates and restreaked onto MYD and MYEG plates.

In all experiments no growth was ever seen on glucose with the empty vector (YEplac112), while only pBOL065, pBOL066 and pBOL067 repeatedly gave good growth on glucose. Plasmid pBOL064 was not re-tested this way after the initial very positive result.

From these results, it was concluded that the codon pair optimized genes of the eutE homologues of:

E. coli (SEQ ID NO:20) encoding the ethanolamine utilization protein EutE from E. coli HS;

L. innocua (SEQ ID NO:23) encoding a hypothetical protein from L. innocua similar to ethanolamine utilization protein EutE, and C. kluyveri (SEQ ID NO:26) encoding acetylating acetaldehyde dehydrogenase in Clostridium kluyveri DSM 555;

and the codon pair optimized gene of the adhE homologue of

S. aureus (SEQ ID NO-29) encoding a bifunctional acetaldehyde/alcohol dehydrogenase in Staphylococcus aureus subsp. aureus N315;

and the non codon pair optimized gene of the adhE homologue

Piromyces sp. E2 (SEQ ID NO:51) encoding a bifunctional acetaldehyde/alcohol dehydrogenase are able to complement the acs2 yeast mutants. These genes encode an enzymatic activity allowing the formation of cytosolic acetyl-CoA from acetaldehyde in yeast.

Conclusions

The supply of cytosolic acetyl-CoA is believed to be a bottleneck in the butanol production in yeast. In order to identify heterologous genes encoding for enzymes forming cytosolic acetyl-CoA in S. cerevisiae a test system based on a delta acs2 yeast mutant was established.

Due to its deficiency in cytosolic acetyl-CoA biosynthesis on glucose, the acs2Δ strain is unable to grow with glucose as sole carbon source.

9 putative acetylating acetaldehyde dehydrogenases identified as candidates for cytosolic acetyl-CoA supply from acetaldehyde were expressed in the acs2Δ yeast. In total, 5 of these 9 genes complemented growth of the acs2Δ strain with glucose as single carbon source. Therewith, the use of the delta acs2 strain as pre-selection tool for feasible routes for cytosolic supply of acetyl-CoA was shown.

4 of 5 acetylating acetaldehyde dehydrogenases identified thus far, eutE homologues of E. coli, L. innocua and C. kluyver and the adhE homologue of S. aureus, and Piromyces sp. E2, were successfully integrated in butanol producing strains of S. cerevisiae. The effect on butanol production was investigated as described in Examples below.

This test system may also be used, to analyse whether pyruvate:NADP oxidoreductase can successfully be overexpressed in yeast. Due to the oxygen sensitivity, this test has to be performed anaerobically.

Examples 4-6 below describe the testing 4 of the 5 selected ACDH genes from Example 3 for improvement of butanol production.

Example 4

Construction of a Butanol Producing Yeast Strain and Knocking Out the ADH1 and ADH2 Genes The six Clostridium acetobutylicum genes involved in butanol biosynthesis from Acetyl-CoA are listed in Table 3. The genes were codon pair optimized for S. cerevisiae as described in WO2008/000632 and expressed from yeast promoters and terminators as listed in Table 3.

Two yeast integration vectors (pBOL34 [SEQ ID NO:41] and pBOL36 [SEQ ID NO:42]), each containing 3 of the six codon pair optimised genes from Clostridium acetobutylicum involved in butanol biosynthesis, were designed and synthesized at Geneart.

The genes ThiL, Hbd and Crt are expressed from pBOL34 containing a AmdS selection marker. The final three genes, Bcd, BdhB and AdhE were expressed from a integration vector with an AmdS selection marker named pBOL36.

TABLE 3

| Genes used for butanol production in S. cerevisiae including the promoter (1000 bp) and terminator (500 bp) | | | |
|---|---|---|---|
| Gene | activity | Promotor | Terminator |
| ThiL | acetyl CoA c-acetyltransferase [E.C. 2.3.1.9 | ADH1 | TDH1 |
| Hbd | 3-hydroxybutyryl-CoA dehydrogenase [E.C.1.1.1.157] | ENO1 | PMA1 |
| Crt | 3-hydroxybutyryl-CoA dehydrogenase [E.C.4.2.1.55] | TDH1 | ADH1 |
| Bcd | butyryl-CoA dehydrogenase [E.C.1.3.99.2]. | PDC1 | TDH1 |
| BdhB | NADH-dependent butanol dehydrogenase [E.C.1.1.1.−]. | ENO1 | PMA1 |
| adhE | alcohol/acetaldehyde CoA dehydrogenase [E.C.: 1.1.1.1/ 1.2.1.10] | TDH1 | ADH2 |

For integration in the ADH2 locus. pBOL36 was linearized by a BsaBI digestion. S. cerevisiae CEN.PK113-5D (MATa MAL2-8c SUC2 ura3-52) was transformed with the linear fragment and grown on plates with YCB (Difco) and 5 mM acetamide as nitrogen source.

The AmdS marker was removed by recombination by growing the transformants for 6 hours in YEPD in 2 ml tubes at 30° C. Cells were subsequently plated on 1.8% agar medium containing YCB (Difco) and 40 mM fluoroacetamide and 30 mM phosphate buffer pH 6.8 supporting growth only from cells that have lost the AmdS marker, Correct integration and recombination were confirmed by PCR. The correct integration of the fragment upstream was confirmed with the following primers:

```
P1:
                            (SEQ ID NO: 10)
5'-GAATTGAAGGATATCTACATCAAG-3'
and P2:
                            (SEQ ID NO: 11)
5'-CCCATCTACGGAACCCTGATCAAGC-3'.
```

The correct integration of the fragment downstream was confirmed with the following primers:

```
P3:
                            (SEQ ID NO: 12)
5'-GATGGTGTCACCATTACCAGGTCTAG-3'
and P4:
                            (SEQ ID NO: 13)
5'-GTTCTCTGGTCAAGTTGAAGTCCATTTTGATTGATTTGACTGTGTT
ATTTTGCGTG-3'.
```

The resulting strain was named BLT021.

pBOL34 was linearized by a PsiI digestion and integrated in the ADH1 locus of BLT021. The transformants were grown on plates containing YCB (Difco) and 5 mM acet-amide. For removal of the AmdS selection marker, colonies were inoculated in YEPD and grown for 6 hours in 2 ml tubes at 30° C. The cells were plated on YCB (Difco) and 40 mM fluoroacetamide and 0.1% ammonium sulphate.

Correct integration and recombination were confirmed by PCR. The correct integration of the fragment upstream was confirmed with the following primer set:

```
P5:
                                    (SEQ ID NO: 14)
    5'-GAACAATAGAGCGACCATGACCTTG-3'
```

The correct integration of the fragment downstream was confirmed with the following primer set:

```
P7:
                                    (SEQ ID NO: 16)
    5'-GATTGAAGGTTTCAAGAACAGGTGATG-3'
and P8:
                                    (SEQ ID NO: 17)
    5'-GGCGATCAGAGTTGAAAAAAAAATG-3'
```

The resulting strain was named BLT057.

Example 5

Introducing ETFα and ETFβ in BLT057

The ETF genes and the Acdh genes as listed in Table 4 were codon pair optimized for *S. cerevisiae* as described in WO2008/000632 and expressed from yeast promoters and terminators as listed in Table 4.

TABLE 4

Promoters and terminators used for expression of codon pair optimized ETF-genes and Acdh genes in *S. cerevisiae*

| | Promotor | Terminator |
|---|---|---|
| Etfα(CpO) | tef1 | tdh2 |
| Etfβ(CpO) | tdh2 | tef1 |
| Acdh64 (AdhE *S. aureus*) | tdh3 | adh |
| Acdh65 (*Clostridium*) | tdh3 | adh |
| Acdh66 (EutE *E. coli*) | tdh3 | adh |
| Acdh67 (lin1129 Ec) | tdh3 | Adh |

The integration vectors expressing ETFα and ETFβ only (pBOL113, [SEQ ID NO:43]) or ETFα and ETFβ combined with Acdh64 (pBOL115, [SEQ ID NO:44]). Acdh65

(pBOL116, [SEQ ID NO:45]), Acdh66 (pBOL118, [SEQ ID NO:46]) or Acdh67 (pBOL120, [SEQ ID NO:47]) were synthesized by Geneart AG.

The vectors, pBOL113, pBOL115, pBOL116, pBOL118 and pBOL120, were linearized with StuI and integrated in the ura3-52 locus of strain BLT057.

The transformants were grown in YNB (Difco) w/o amino acids+2% galactose to select for uracil prototrophic strains. The strains derived from strain BLT057 with pBOL113/115/116/118/120 integrated in the genome were designated strains: BLT071, BLT072. BLT073. BLT074 and BLT075, respectively.

Example 6

Improved Butanol Production by Expressing Positive Acdh Genes

Strains BLT071 through BLT075 as prepared in Example 5 were grown in Verduyn medium (Verduyn et al. (1992) Yeast 8: 501-517) in which the ammonium sulphate is replaced by 2 g/l ureum and which further contains 4 wt. % galactose. Cells were grown in 100 ml shake flasks containing 50 ml of medium for 72 hours at 30° C. at 180 rpm in a rotary shaker.

The butanol concentration was determined in the super-natant of the culture. Samples were analysed on a HS-GC equipped with a flame ionisation detector and an automatic injection system. Column J & W DB-1 length 30 m, id 0.53 mm, df 5 μm. The following conditions were used: helium as carrier gas with a flow rate of 5 ml/min. Column temperature was set at 110° C. The injector was set at 140° C. and the detector performed at 300° C. The data was obtained using Chromeleon software. Samples were heated at 60° C. for 20 min in the headspace sampler. One (1) ml of the headspace volatiles were automatically injected on the column.

1-Butanol production of the various strains was as follows:
BLT057: 120 mg/l
BLT071: 450 mg/l
BLT072: 500 mg/l
BLT073: 600 mg/l
BLT074: 670 mg/l
BLT075: 700 mg/l The results show that introduction of electron transfer flavoproteins (ETF alpha and ETF beta) and/or introduction of acetylating acetaldehyde dehydrogenases as identified by a complementation assay of Example 3, increase the butanol production level.

The invention claimed is:

1. A method of identifying a heterologous polypeptide having enzymatic activity for converting pyruvate, acetaldehyde or acetate into acetyl-CoA in a cytosol of a yeast cell comprising:

providing a mutated yeast cell, wherein said mutation comprises an inactivation of at least one gene of a pyruvate dehydrogenase (PDH) by-pass, selected from the genes encoding the enzymes pyruvate decarboxylase (PDC), acetaldehyde dehydrogenase (ALD), and acetyl-CoA synthetase (ACS);

transforming said mutated yeast cell with an expression vector to produce a recombinant mutated yeast cell, wherein the expression vector comprises comprising at least one heterologous nucleotide sequence operably linked to a promoter functional in yeast and said heterologous nucleotide sequence encodes encoding a candidate polypeptide having potential enzymatic activity for converting pyruvate, acetaldehyde or acetate into acetyl-CoA acetyl CoA;

testing said recombinant mutated yeast cell for its ability to grow on minimal medium containing glucose as sole carbon source and wherein the minimal medium does not contain xylose as a carbon source, and identifying said candidate polypeptide as a heterologous polypeptide having enzymatic activity for converting pyruvate, acetaldehyde or acetate into acetyl-CoA acetyl CoA in the cytosol of said yeast cell when growth of said cell is observed.

2. The method according to claim 1, wherein said yeast cell is a cell of *Saccharomyces cerevisiae* and wherein said heterologous nucleotide sequence is codon pair optimized for expression in *Saccharomyces cerevisiae*.

3. The method according to claim 2, wherein said mutation comprises an inactivation of the gene for acetyl-CoA synthetase isoform 2 (acs2).

4. The method-according to claim 1, wherein said candidate polypeptide having enzymatic activity for converting acetaldehyde into acetyl-CoA is an (putative) acetylating acetaldehyde dehydrogenase (acdh).

* * * * *

SEQUENCE LISTING

```
Sequence total quantity: 52
SEQ ID NO: 1           moltype = DNA  length = 64
FEATURE                Location/Qualifiers
misc_feature           1..64
                       note = primer 5'acs2
source                 1..64
                       mol_type = other DNA
                       organism = synthetic construct
SEQUENCE: 1
atacacaaac agaatacagg aaagtaaatc aatacaataa taaaacagct gaagcttcgt   60
acgc                                                               64

SEQ ID NO: 2           moltype = DNA  length = 67
FEATURE                Location/Qualifiers
misc_feature           1..67
                       note = primer 3'acs2
```

-continued

```
source                    1..67
                          mol_type = other DNA
                          organism = synthetic construct
SEQUENCE: 2
tctcattacg aaatttttct catttaagtt atttcttttt ttgaggcata ggccactagt   60
ggatctg                                                             67

SEQ ID NO: 3              moltype = DNA   length = 20
FEATURE                   Location/Qualifiers
misc_feature              1..20
                          note = probe 5'acs2
source                    1..20
                          mol_type = other DNA
                          organism = synthetic construct
SEQUENCE: 3
gatattcggt agccgattcc                                               20

SEQ ID NO: 4              moltype = DNA   length = 20
FEATURE                   Location/Qualifiers
misc_feature              1..20
                          note = probe 3'acs2
source                    1..20
                          mol_type = other DNA
                          organism = synthetic construct
SEQUENCE: 4
ccgtaacctt ctcgtaatgc                                               20

SEQ ID NO: 5              moltype = DNA   length = 20
FEATURE                   Location/Qualifiers
misc_feature              1..20
                          note = probe ACS2internal
source                    1..20
                          mol_type = other DNA
                          organism = synthetic construct
SEQUENCE: 5
cggattcgtc atcagcttca                                               20

SEQ ID NO: 6              moltype = DNA   length = 20
FEATURE                   Location/Qualifiers
misc_feature              1..20
                          note = probe KanA
source                    1..20
                          mol_type = other DNA
                          organism = synthetic construct
SEQUENCE: 6
cgcacgtcaa gactgtcaag                                               20

SEQ ID NO: 7              moltype = DNA   length = 20
FEATURE                   Location/Qualifiers
misc_feature              1..20
                          note = probe KanB
source                    1..20
                          mol_type = other DNA
                          organism = synthetic construct
SEQUENCE: 7
tcgtatgtga atgctggtcg                                               20

SEQ ID NO: 8              moltype = DNA   length = 64
FEATURE                   Location/Qualifiers
misc_feature              1..64
                          note = primer MCS-5'Tadh
source                    1..64
                          mol_type = other DNA
                          organism = synthetic construct
SEQUENCE: 8
aaggtacctc tagactagtc ccgggctgca gtcgactcga gcgaatttct tatgatttat   60
gatt                                                                64

SEQ ID NO: 9              moltype = DNA   length = 39
FEATURE                   Location/Qualifiers
misc_feature              1..39
                          note = primer Tadh1-Hind
source                    1..39
                          mol_type = other DNA
                          organism = synthetic construct
SEQUENCE: 9
aggaagctta ggcctgtgtg gaagaacgat tacaacagg                          39

SEQ ID NO: 10             moltype = DNA   length = 24
```

```
FEATURE              Location/Qualifiers
misc_feature         1..24
                     note = primer P1
source               1..24
                     mol_type = other DNA
                     organism = synthetic construct
SEQUENCE: 10
gaattgaagg atatctacat caag                                        24

SEQ ID NO: 11        moltype = DNA   length = 25
FEATURE              Location/Qualifiers
misc_feature         1..25
                     note = primer P2
source               1..25
                     mol_type = other DNA
                     organism = synthetic construct
SEQUENCE: 11
cccatctacg gaaccctgat caagc                                       25

SEQ ID NO: 12        moltype = DNA   length = 26
FEATURE              Location/Qualifiers
misc_feature         1..26
                     note = primer P3
source               1..26
                     mol_type = other DNA
                     organism = synthetic construct
SEQUENCE: 12
gatggtgtca ccattaccag gtctag                                      26

SEQ ID NO: 13        moltype = DNA   length = 56
FEATURE              Location/Qualifiers
misc_feature         1..56
                     note = Primer P4
source               1..56
                     mol_type = other DNA
                     organism = synthetic construct
SEQUENCE: 13
gttctctggt caagttgaag tccattttga ttgatttgac tgtgttattt tgcgtg     56

SEQ ID NO: 14        moltype = DNA   length = 25
FEATURE              Location/Qualifiers
misc_feature         1..25
                     note = Primer P5
source               1..25
                     mol_type = other DNA
                     organism = synthetic construct
SEQUENCE: 14
gaacaataga gcgaccatga ccttg                                       25

SEQ ID NO: 15        moltype = DNA   length = 25
FEATURE              Location/Qualifiers
misc_feature         1..25
                     note = Primer P6
source               1..25
                     mol_type = other DNA
                     organism = synthetic construct
SEQUENCE: 15
gacatcagcg tcaccagcct tgatg                                       25

SEQ ID NO: 16        moltype = DNA   length = 27
FEATURE              Location/Qualifiers
misc_feature         1..27
                     note = Primer P7
source               1..27
                     mol_type = other DNA
                     organism = synthetic construct
SEQUENCE: 16
gattgaaggt ttcaagaaca ggtgatg                                     27

SEQ ID NO: 17        moltype = DNA   length = 25
FEATURE              Location/Qualifiers
misc_feature         1..25
                     note = Primer P8
source               1..25
                     mol_type = other DNA
                     organism = synthetic construct
SEQUENCE: 17
ggcgatcaga gttgaaaaaa aaatg                                       25
```

```
SEQ ID NO: 18            moltype = DNA   length = 1404
FEATURE                  Location/Qualifiers
source                   1..1404
                         mol_type = other DNA
                         organism = Escherichia coli
CDS                      1..1404
SEQUENCE: 18
atgaatcaac aggatattga acaggtggtg aaagcggtac tgctgaaaat gcaaagcagt   60
gacacgccgt ccgccgccgt tcatgagatg ggcgttttcg cgtccctgga tgacgccgtt  120
gcggcagcca aagtcgccca gcaaggggtta aaaagcgtgg caatgcgcca gttagccatt  180
gctgccattc gtgaagcagg cgaaaaacac gccagagatt tagcgggaact tgccgtcagt  240
gaaaccggca tggggcgcgt tgaagataaa tttgcaaaaa acgtcgctca ggcgcgcggc  300
acaccaggcg ttgagtgcct ctctccgcaa gtgctgactg gcgacaacgg cctgacccta  360
attgaaaacg caccctgggg cgtggtggct tcggtgacgc cttccactaa cccggcggca  420
accgtaatta acaacgccat cagcctgatt gccgcgggca acagcgtcat ttttgccccg  480
catccggcgg cgaaaaaagt ctcccagcgg gcgattacgc tgctcaacca ggcgattgtt  540
gccgcaggtg ggccggaaaa cttactggtt actgtggcaa atccggatat cgaaaccgcg  600
caacgcttgt tcaagtttcc gggtatcggc ctgctggtgg taaccggcgg cgaagcggta  660
gtagaagcgg cgcgtaaaca caccaataaa cgtctgattg ccgcaggcgc tggcaacccg  720
ccggtagtgg tggatgaaac cgccgacctc gccgtgccg ctcagtccat cgtcaaaggc  780
gcttctttcg ataacaacat catttgtgcc gacgaaaagg tactgattgt tgttgatagc  840
gtagccgatg aactgatgcg tctgatggaa ggccagcacg cggtgaaact gaccgcagaa  900
caggcgcagc agctgcaacc ggtgttgctg aaaaatatcg acgagcgcgg aaaaggcacc  960
gtcagccgtg actgggttgg tcgcgacgca ggcaaaatcg cggcggcaat cggccttaaa 1020
gttccgcaag aaacgcgcct gctgtttgtg aaaccaccg cagaacatcc gtttgccgtg 1080
actgaactga tgatgccggt gttgcccgtc gtgcgcgtca gccaacgtgg cgatgccatt 1140
gcgctagcgg tgaaactgga aggcggttgc caccacacgg cggcaatgca ctcgcgcaac 1200
atcgaaaaca tgaaccagat ggcgaatgct attgatacca gcattttcgt taagaacgga 1260
ccgtgcattg ccgggctggg gctgggcggg gaaggctgga ccaccatgac catcaccacg 1320
ccaaccggtg aaggggtaac cagcgcgcgt acgtttgtcc gtctgcgtcg ctgtgtatta 1380
gtcgatgcgt ttcgcattgt ttaa                                        1404

SEQ ID NO: 19            moltype = AA   length = 467
FEATURE                  Location/Qualifiers
source                   1..467
                         mol_type = protein
                         organism = Escherichia coli
SEQUENCE: 19
MNQQDIEQVV KAVLLKMQSS DTPSAAVHEM GVFASLDDAV AAAKVAQQGL KSVAMRQLAI   60
AAIREAGEKH ARDLAELAVS ETGMGRVEDK FAKNVAQARG TPGVECLSPQ VLTGDNGLTL  120
IENAPWGVVA SVTPSTNPAA TVINNAISLI AAGNSVIFAP HPAAKKVSQR AITLLNQAIV  180
AAGGPENLLV TVANPDIETA QRLFKFPGIG LLVVTGGEAV VEAARKHTNK RLIAAGAGNP  240
PVVVDETADL ARAAQSIVKG ASFDNNIICA DEKVLIVVDS VADELMRLME GQHAVKLTAE  300
QAQQLQPVLL KNIDERGKGT VSRDWVGRDA GKIAAAIGLK VPQETRLLFV ETTAEHPFAV  360
TELMMPVLPV VRVANVADAI ALAVKLEGGC HHTAAMHSRN IENMNQMANA IDTSIFVKNG  420
PCIAGLGLGG EGWTTMTITT PTGEGVTSAR TFVRLRRCVL VDAFRIV                467

SEQ ID NO: 20            moltype = DNA   length = 1401
FEATURE                  Location/Qualifiers
misc_feature            1..1401
                         note = optimised sequence
source                   1..1401
                         mol_type = other DNA
                         organism = synthetic construct
SEQUENCE: 20
atgaaccaac aagatatcga acaagttgtc aaggctgtct tgttgaaaat gcaatcttct   60
gacactccat ctgctgctgt ccacgaaatg ggtgtttttcg cttcttttgga cgacgctgtt  120
gctgctgcca aggttgctca acaaggtttg aaatctgttg ccatgagaca attggccatt  180
gctgccatca gagaagctgg tgaaaagcat gccagagact tggctgaatt ggctgtctcc  240
gaaaccggta tgggtagagt tgaagacaaa ttcgctaaga acgttgctca agctagaggt  300
actccaggtg tcgaatgttt gtctccacaa gtcttgaccg gtgataatgg tttgactttg  360
attgaaaatg ctccatgggg tgttgttgct tccgtcaccc catctaccaa cccagctgct  420
actgtcatca acaacgccat ctctttgatt gctgctggta actccgttat cttcgctcca  480
cacccagctg ccaagaaggt ttctcaaaga gccatcactt tattgaacca ggcattgtt  540
gctgctggtg gtccagaaaa cttgttggtc actgttgcca acccagatat cgaaactgct  600
caaagattat tcaagttccc aggtatcggt ctattagtcg tcactggtgg tgaagctgtt  660
gttgaagctg ccagaaagca caccaacaag agattgattg ctgctggtgc tggtaaccct  720
cctgttgttg tcgatgaaac cgctgatttg gccagagctg ctcaatccat tgtcaagggt  780
gcttctttcg acaacaacat catctgtgct gacgaaaagg ttttgattgt tgttgactcc  840
gttgctgacg aattgatgag attgatggaa ggtcaacatg ccgtcaagtt gactgctgaa  900
caagctcaac aattgcaacc agttttgttg aagaacatcg atgaaagagg taagggtacc  960
gtctccagag actgggttgg tagagatgct ggtaagattc tgctgccat cggtttgaag 1020
gttccacaag aaaccagatt attattcgtc gaaaccaccg ctgaacaccc atttgctgtc 1080
actgaattga tgatgccagt cttaccagtt gtccgtgttg ctaacgttgc tgacgctatt 1140
gctttggctc tcaaattgga aggtggttgc caccacactg ctgccatgca ctccagaaac 1200
atcgaaaaca tgaaccaaat ggctaacgcc attgacactt ccatctttgt caagaacggt 1260
ccatgtatcg ctggtttggg tttgggtggt gaaggttgga ccaccatgac catcaccacc 1320
ccaactggtg aaggtgtcac ttctgccaga actttcgtca gattacgtcg ttgtgttttg 1380
gtcgatgctt tcagaattgt t                                            1401
```

-continued

```
SEQ ID NO: 21          moltype = DNA  length = 1410
FEATURE                Location/Qualifiers
source                 1..1410
                       mol_type = other DNA
                       organism = Listeria innocua
CDS                    1..1410
SEQUENCE: 21
atggaatcat tagaactcga acaactggta aaaaaagttc tcttagaaaa attagcagaa   60
caaaaagaag taccaacaaa aacaactaca caaggcgcga aaagtggcgt ttttgataca   120
gttgacgagg ctgttcaagc agcagttata gcgcagaatt gctataaaga aaaatcactt   180
gaagaacgcc gcaatgttgt aaaagcaatt cgtgaagcac tttatccaga aattgaaaca   240
attgcgacaa gagcagttgc agagactggt atgggaaatg tgacagataa aattttgaaa   300
aacacgttag caatcgaaaa aacgccaggg gtagaagatt tatatacaga agtagctaca   360
ggtgataacg gtatgacact atatgaactc tctccgtatg gcgtaattgg tgcagtagcg   420
ccgagcacaa acccaacgga aacattgatt tgtaattcaa tcggtatgct cgcagctgga   480
aatgccgttt tttatagccc tcatccaggg gcaaaaaaca tttcactgtg gttgattgaa   540
aaactaaaca caattgttcg cgatagttgt ggtatagata atctaattgt caccgtggct   600
aaaccatcca tccaagcagc tcaagaaatg atgaaccatc caaaagtacc gctacttgtt   660
attacaggtg gtccgggcgt tgttctccaa gcgatgcaat caggtaaaaa agtgattgga   720
gcaggagcag ggaacccgcc ttctattgtt gacgaaacag ctaatatcga aaaagcggct   780
gctgacatcg tagacggagc atcttttgac cataatattt tatgtattgc tgaaaaaagt   840
gtggtagctg ttgatagcat tgctgatttc ttgttattcc aaatggaaaa aaatggtgcc   900
cttcatgtta ctaatccaag tgatattcaa aaattagaaa aagtagccgt taccgataaa   960
ggtgtaacta ataaaaaatt agtcggaaaa agtgcaactg aaatcttaaa agaagcagga   1020
atagcttgtg attttacacc acgtttaatc attgtgtaaa cggagaaatc tcatccattt   1080
gcaacagtag agctattaat gccaatcgtt ccagttgtaa gggtgcctga tttttgacgaa   1140
gcccttgaag tggctattga actcgaacaa ggcttacatc atacagcaac aatgcattca   1200
caaaatatct cgagattaaa caaagctgca agagatatgc aaacttccat ctttgtcaaa   1260
aatggtccgt cctttgcggg attaggcttt agaggagaag gtagtactac tttcactatt   1320
gcaacgccta ctggagaagg aacaactaca gcacgtcatt ttgctagacg ccgccgctgt   1380
gttttaacag atggtttttc gattcgttaa                                    1410

SEQ ID NO: 22          moltype = AA  length = 469
FEATURE                Location/Qualifiers
source                 1..469
                       mol_type = protein
                       organism = Listeria innocua
SEQUENCE: 22
MESLELEQLV KKVLLEKLAE QKEVPTKTTT QGAKSGVFDT VDEAVQAAVI AQNCYKEKSL   60
EERRNVVKAI REALYPEIET IATRAVAETG MGNVTDKILK NTLAIEKTPG VEDLYTEVAT   120
GDNGMTLYEL SPYGVIGAVA PSTNPTETLI CNSIGMLAAG NAVFYSPHPG AKNISLWLIE   180
KLNTIVRDSC GIDNLIVTVA KPSIQAAQEM MNHPKVPLLV ITGGPGVVLQ AMQSGKKVIG   240
AGAGNPPSIV DETANIEKAA ADIVDGASFD HNILCIAEKS VVAVDSIADF LLFQMEKNGA   300
LHVTNPSDIQ KLEKVAVTDK GVTNKKLVGK SATEILKEAG IACDFTPRLI IVETEKSHPF   360
ATVELLMPIV PVVRVPDFDE ALEVAIELEQ GLHHTATMHS QNISRLNKAA RDMQTSIFVK   420
NGPSFAGLGF RGEGSTTFTI ATPTGEGTTT ARHFARRRRC VLTDGFSIR             469

SEQ ID NO: 23          moltype = DNA  length = 1407
FEATURE                Location/Qualifiers
misc_feature           1..1407
                       note = optimised sequence
source                 1..1407
                       mol_type = other DNA
                       organism = synthetic construct
SEQUENCE: 23
atggaatctt tggaattgga acaattagtc aagaaggttt tgttggaaaa attggctgaa   60
caaaaggaag ttccaaccaa gaccaccacc caaggtgcca gtccggtgt tttcgatacc   120
gtcgatgaag ctgtccaagc tgccgtcatt gctcaaaact gttacaagga aaaatctttg   180
gaagaaagaa gaaacgttgt caaggccatc agagaagctc tatacccaga aatcgaaacc   240
attgctacca gagctgttgc tgaaaccggt atgggtaatg tcaccgataa aatcttgaag   300
aacactttag ctatcgaaaa gactccaggt gttgaagact gtacactga gttgctacc   360
ggtgacaacg gtatgacttt atacgaatta tctccatacg gtgtcatcgg tgctgttgct   420
ccatctacca acccaactga aactttgatc tgtaactcca tcggtatgtt ggctgctggt   480
aacgccgttt tctactctcc tcacccaggt gccaagaaca tctctttatg gttgattgaa   540
aagttgaaca ctatcgtcag agattcttgt ggtattgaca cttgattgt caccgttgcc   600
aagccatcta tccaagctgc tcaagaaatg atgaaccacc caaaggttcc attgttggtc   660
atcactggtg gtccaggtgt tgtcttgcaa gctatgcaat ctggtaagaa ggttatcggt   720
gctggtgctg gtaaccctcc atccatcgtt gacgaaaccg ctaacattga aaaggctgct   780
gctgacattg tcgacggtgc ttccttgac cataatatct tgtgtatcgc tgaaaagtct   840
gttgttgccg ttgactccat tgctgacttc ttgttgttcc aaatggaaaa gaacggtgct   900
ttgcacgtca ctaacccatc tgatatccaa aaattggaaa aggttgccgt cactgacaag   960
ggtgtcacca acaagaaatt ggttggtaag tctgccactg aaatcttgaa agaagctggt   1020
attgcttgtg atttcacccc aagattgatt attgtcgaaa ctgaaaagtc cacccattc   1080
gctactgttg aattgttgat gccaattgtt ccagttgtca gagttccaga cttcgatgaa   1140
gctttggaag ttgccattga attggaacaa ggtctacatc acactgctac catgcactct   1200
caaaacatct ccagattgaa caaggctgcc cgtgacatgc aaacctccat ctttgtcaag   1260
aacggtccat ctttcgctgg tttaggtttc agaggtgaag gttccaccac tttcaccatt   1320
gctactccaa ctggtgaagg tactaccact gcccgtcact cgctagaag aagaagatgt   1380
```

```
gtcttgactg atggtttctc cattaga                                        1407

SEQ ID NO: 24            moltype = DNA   length = 1476
FEATURE                  Location/Qualifiers
source                   1..1476
                         mol_type = other DNA
                         organism = Clostridium kluyveri
CDS                      1..1476
SEQUENCE: 24
atggagataa tggataagga cttacagtca atacaggaag taagaactct tatagcaaaa   60
gcaaagaaag ctcaagcaga atttaaaaat ttttctcaag aagctgtaaa caaggtaata   120
gaaaaaaatag ctaaggctac agaagttgaa gctgtaaaac ttgcaaaatt ggcatatgaa   180
gatacaggat atggaaaatg ggaagataaa gtaataaaga ataagttttc aagtatagta   240
gtttataact atattaaaga tttgaaaacg gttggaattt taaaagaaga caaggaaaag   300
aaattaatag atatagctgt tccacttgga gttatagcag gacttatacc ttcaactaac   360
ccaacttcaa cagcaatatt caaggtatta atagcattaa aggcaggaaa tgcaatagta   420
ttctcaccac atccaacagc agtaagaagt attacagaaa ctgtaaagat aatgcagaaa   480
gctgcagtag aagcaggagc accagatgga ttaatccaat gtatgtcaat attgacagta   540
gaaggtactg ctgaattgat gaagaataag gatacagcac ttatccttgc aacaggtgga   600
gaaggaatgg taagagcagc ttacagttca ggaacaccag ctataggagt tggacctgga   660
aacggcccat gctttattga agaacagca gatattccta cagcagtaag aaaagtaata   720
ggcagtgata cttttgataa tggagtaata tgtgcttcag aacaatcaat aatagcaggg   780
acagtaaaga aagcagagat aattgaagaa ttcaagagac aaaaaggata tttcttaaat   840
gcagaagaat cagaaaaagt aggcaagatt ttattaagag ctaatggaac accaaaccca   900
gcaatagtag aaaagatgt tcaagcatta gcaaaattag caggaataag cataccaagc   960
gatgcggtaa tattacttttc agagcagaca gatgtgagtc caaagaaccc ttatgcaaag   1020
gaaaaattag ctccagtact tgcattctat acagtagaag actggcatga agcatgtgaa   1080
aaatccttag cacttcttca taaccaagga agtggacata cattaataat tcactcacag   1140
aatgaagaaa tcataagaga attcgcattg aagaaaccag tatcaagaat acttgtaaat   1200
tcacctggat cacttggagg aataggtgga gctacaaatc ttgtaccatc acttacatta   1260
ggctgtggag cagtaggtgg aagtgcaact tcagataacg taggaccaga aaacttattc   1320
aacataagaa aagtagctta tggaactacg acagtagaag aaataagaga agcttttggt   1380
gtaggagcag cttcatcaag tgcaccagca gaaccagaag ataatgaaga tgtacaggct   1440
atagtaaaag ctataatggc taaattaaat cttaa                              1476

SEQ ID NO: 25            moltype = AA   length = 491
FEATURE                  Location/Qualifiers
source                   1..491
                         mol_type = protein
                         organism = Clostridium kluyveri
SEQUENCE: 25
MEIMDKDLQS IQEVRTLIAK AKKAQAEFKN FSQEAVNKVI EKIAKATEVE AVKLAKLAYE   60
DTGYGKWEDK VIKNKFSSIV VYNYIKDLKT VGILKEDKEK KLIDIAVPLG VIAGLIPSTN   120
PTSTAIFKVL IALKAGNAIV FSPHPTAVRS ITETVKIMQK AAVEAGAPDG LIQCMSILTV   180
EGTAELMKNK DTALILATGG EGMVRAAYSS GTPAIGVGPG NGPCFIERTA DIPTAVRKVI   240
GSDTFDNGVI CASEQSIIAE TVKKAEIIEE FKRQKGYFLN AEESEKVGKI LLRANGTPNP   300
AIVGKDVQAL AKLAGISIPS DAVILLSEQT DVSPKNPYAK EKLAPVLAFY TVEDWHEACE   360
KSLALLHNQG SGHTLIIHSQ NEEIIREFAL KKPVSRILVN SPGSLGGIGG ATNLVPSLTL   420
GCGAVGGSAT SDNVGPENLF NIRKVAYGTT TVEEIREAFG VGAASSSAPA EPEDNEDVQA   480
IVKAIMAKLN L                                                        491

SEQ ID NO: 26            moltype = DNA   length = 1473
FEATURE                  Location/Qualifiers
misc_feature             1..1473
                         note = optimised sequence
source                   1..1473
                         mol_type = other DNA
                         organism = synthetic construct
SEQUENCE: 26
atggaaatca tggacaagga tttgcaatcc atccaagaag ttagaacttt gattgccaag   60
gccaagaagg ctcaagctga attcaagaac ttttcccaag aagctgttaa caaggtcatc   120
gaaaagatcg ccaaggctac tgaagttgaa gctgtcaaat ggccaaatt ggcttacgaa   180
gacaccggtt acggtaaatg ggaagacaag gtcatcaaga caaattctc tccattgtt   240
gtctacaact acatccaagg atttgaagacc gttggtatct tgaaggaaga caaggaaaag   300
aaattgattg acattgctgt cccattaggt gtcattgctg gtttgattcc atctaccaac   360
ccaacttcca ctgccatttt caaggtcttg attgctttga aggctggtaa cgccattgtc   420
ttctctccac acccaactgc tgtccgttcc atcactgaaa ccgttaagat catgcaaaag   480
gctgctgttg aagctggtgc tccagatggt ttgatccaat gtatgtccat tttgaccgtt   540
gaaggtactg ctgaattgat gaagaacaag gacaccgctt tgatcttggc taccggtggt   600
gaaggtatgg ttagagctgc ttactcctct ggtactccag ccatcggtgt cggtccaggt   660
aacggtccat gtttcatcga aagaactgct gacattccaa ctgctgttag aaaggttatc   720
ggttctgaca ctttcgacaa cggtgtcatc tgtgcttctg aacaatccat cattgctgaa   780
accgtcaaga aggctgaaat catcgaagaa ttcaagagac aaaaagggtta cttcttgaat   840
gctgaagaat ctgaaaagt aggtaagatt ctattacgtg ccaacggtac tccaaaccca   900
gccatcgttg gtaaggatgt ccaagctttg gccaaattgg ctggtatttc cattccatct   960
gatgctgtta tctactatc cgaacaaacc gatgtttctc ctaaaaatcc atacgctaag   1020
gaaaaattgg ctccagtctt ggctttctac accgtcgaag actggcatga agcttgtgaa   1080
aagtctttgg ctttattgca caaccaaggt tctggtcaca ctttgatcat ccactctcaa   1140
aacgaagaaa tcattagaga atttgctttg aagaagcctg tttccagaat tttggttaac   1200
```

```
tctccaggtt ctttgggtgg tatcggtggt gctaccaact tagtcccatc tttgacttta   1260
ggttgtggtg ctgttggtgg ttctgccacc tctgacaacg ttggtccaga aaacttgttc   1320
aacatcagaa aggttgctta cggtaccacc accgtcgaag aaatcagaga agctttcggt   1380
gtcggtgctg cttcttcttc tgctccagct gaaccagaag acaacgaaga tgttcaagcc   1440
attgttaagg ccatcatggc caaattgaac ttg                                 1473
```

```
SEQ ID NO: 27              moltype = DNA   length = 2610
FEATURE                    Location/Qualifiers
source                     1..2610
                           mol_type = other DNA
                           organism = Staphylococcus aureus
CDS                        1..2610
SEQUENCE: 27
atgttaacta tacctgaaaa agaaaatcgt ggatcgaaag aacaagaagt ggcaattatg   60
attgatgctc tagctgacaa agggaaaaaa gcattagaag cattatctaa aaagtcacaa   120
gaagaaattg atcatattgt tcatcaaatg agcttagcag ctgttgatca acatatggtg   180
ctagcaaaat tagcacatga agaaactgga agaggtatat acgaagataa agcgattaaa   240
aatttatacg cttctgaata tatatggaat tcaataaaag acaataagac agtaggggt    300
attggtgaag ataaagaaaa aggattaacg tatgtagcgg aaccaattgg tgttatttgt   360
ggtgttacgc caacaacaaa tcctacgtcg acaactattt ttaaagcgat gattgcaatt   420
aagacaggaa atccaatcat ttttgcattc catccaagtg cacaagaatc gtcgaagcgt   480
gcagcagaag ttgtattaga agcggcaatg aaggcaggtg cacctaaaga tattattcag   540
tggattgaag tgccttctat cgaagcaaca aaacaattaa tgaatcacaa aggtattgca   600
ttagttctag caacaggtgg ttcgggcatg gttaagtctg catattcaac tggcaaaccg   660
gcattaggtg tgggaccagg taacgtgccg tcttacattg aaaaaacagc acacattaaa   720
cgtgcagtaa atgatatcat tggttcaaaa acatttgata atggtatgat ttgtgcttct   780
gaacaagttg tagtcattga taaagaaatt tataaagatg ttactaatga atttaaagca   840
catcaagcat actttgttaa aaaagatgaa ttacaacgct tagaaaatgc aattatgaat   900
gaacaaaaaa caggtattaa gcctgatatt gtcggtaaat ctgcagttga aatagctgaa   960
ttagcaggta tacctgtccc cgaaaataca aaacttatca tagccgaaat tagcggtgta   1020
ggttcagact atccgttatc tcgtgaaaaa ttatctccag tattagcctt agtaaaagcc   1080
caatctacaa aacaagcatt tcaaatttgt gaagacacac tacattttgg tggattagga   1140
cacacagccg ttatccatac agaagatgaa acattacaaa aagattttgg actaagaatg   1200
aaagcttgtc gtgtacttgt aaatacacca tcagcggttg gaggtattgg tgatatgtat   1260
aacgaattga ttccgtcttt aacattaggt tgtggttcgt acggtagaaa ctcaatttca   1320
cataatgtta gtgcgacaga tttattaaac attaaaacga ttgctaaacg acgtaataat   1380
actcaaattt tcaaggtgcc tgctcaaatt tattttgaag aaaatgcaat catgagtcta   1440
acaacaatgg acaagattga aaaagtgatg attgtctgtg accctggtat ggtagaattc   1500
ggttatacaa aaacagttga gaatgtatta agacaaagac cggaacagcc tcaaattaaa   1560
atatttagcg aagtcgaacc gaacccatca actaatacag tatataaagg tctgaaaatg   1620
atggttgatt tccaaccaga tacaatcatt gcacttggtg gtggttcagc gatgggatgct   1680
gcaaaagcaa tgtggatgtt ctttgaacac cctgagacat cattcttcgg tgctaaacaa   1740
aagttcctag acatcggtaa acgtacttat aaaataggca ttggctgaaaa tgcgacgttc   1800
atttgtatcc ctacgacatc aggtacaggt tcagaagtaa caccatttgc agttatcaca   1860
gatagtgaaa caaatgtaaa atatccgttg gctgattttg cttttaacacc tgacgttgca   1920
attattgacc ctcaatttgt gatgagtgtg ccaaaaagcg ttacagcaga tacaggaatg   1980
gatgtactaa cgcatgcaat ggaatcatat gtatctgtaa tggcttcaga ctatacaaga   2040
ggtttgagtc tacaagcgat taaattgacg ttcgaatatt taaaatcatc tgttgaaaag   2100
ggtgataaag tttcaagaga gaaaatgcat aacgcatcaa ctttggctgg tatggcattt   2160
gcaaatgcat tcttaggcat tgcacactca attgcacata aaattggtgg cgaatatggt   2220
attccgcatg gtagagcgaa tgcgatatta ctaccgcata ttatccgtta taatgccaaa   2280
gacccgcaaa aacatgcatt attccctaaa tatgagttct tcagagcaga tacagattat   2340
gcagatattg ccaaattctt aggattaaaa gggaatacga cagaagcact cgtagaatca   2400
ttagctaaag ctgtctacga attaggtcaa tcagtcggaa ttgaaatgaa tttgaaatca   2460
caaggtgtgt ctgaagaaga attaaatgaa tcaattgata gaatggcaga gctcgcattt   2520
gaagatcaat gtacaactgc taatcctaaa gaagcactaa tcagtgaaat caaagatatc   2580
attcaaacat catatgatta taagcaataa                                     2610
```

```
SEQ ID NO: 28              moltype = AA   length = 869
FEATURE                    Location/Qualifiers
source                     1..869
                           mol_type = protein
                           organism = Staphylococcus aureus
SEQUENCE: 28
MLTIPEKENR GSKEQEVAIM IDALADKGKK ALEALSKKSQ EEIDHIVHQM SLAAVDQHMV   60
LAKLAHEETG RGIYEDKAIK NLYASEYIWN SIKDNKTVGI IGEDKEKGLT YVAEPIGVIC   120
GVTPTTNPTS TTIFKAMIAI KTGNPIIFAF HPSAQESSKR AAEVVLEAAM KAGAPKDIIQ   180
WIEVPSIEAT KQLMNHKGIA LVLATGGSGM VKSAYSTAGP ALGVGPGNVP SYIEKTAHIK   240
RAVNDIIGSK TFDNGMICAS EQVVVIDKEI YKDVTNEFKA HQAYFVKKDE LQRLENAIMN   300
EQKTGIKPDI VGKSAVEIAE LAGIPVPENT KLIIAEISGV GSDYPLSREK LSPVLALVKA   360
QSTKQAFQIC EDTLHFGGLG HTAVIHTEDE TLQKDFGLRM KACRVLVNTP SAVGGIGDMY   420
NELIPSLTLG CGSYGRNSIS HNVSATDLLN IKTIAKRRNN TQIFKVPAQI YFEENAIMSL   480
TTMDKIEKVM IVCDPGMVEF GYTKTVENVL RQRTEQPQIK IFSEVEPNPS TNTVYKGLEM   540
MVDFQPDTII ALGGGSAMDA AKAMWMFFEH PETSFFGAKQ KFLDIGKRTY KIGMPENATF   600
ICIPTTSGTG SEVTPFAVIT DSETNVKYPL ADFALTPDVA IIDPQFVMSV PKSVTADTGM   660
DVLTHAMESY VSVMASDYTR GLSLQAIKLT FEYLKSSVEK GDKVSREKMH NASTLAGMAF   720
ANAFLGIAHS IAHKIGGEYG IPHGRANAIL LPHIIRYNAK DPQKHALFPK YEFFRADTDY   780
ADIAKFLGLK GNTTEALVES LAKAVYELGQ SVGIEMNLKS QGVSEEELNE SIDRMAELAF   840
EDQCTTANPK EALISEIKDI IQTSYDYKQ                                       869
```

-continued

```
SEQ ID NO: 29          moltype = DNA  length = 2607
FEATURE                Location/Qualifiers
misc_feature           1..2607
                       note = optimised sequence
source                 1..2607
                       mol_type = other DNA
                       organism = synthetic construct
SEQUENCE: 29
atgttgacca ttccagaaaa ggaaaacaga ggttccaagg aacaagaagt tgccatcatg     60
attgatgctt tagctgacaa aggtaagaag gctttggaag ctttgtccaa gaagtctcaa    120
gaagaaattg accacattgt ccaccaaatg tccttggctg ctgttgacca acacatggtt    180
ttggccaagt tggctcatga agaaaccggt agaggtatct acgaagacaa ggctatcaag    240
aacttatacg cctctgaata catctggaac tccatcaagg acaacaagac tgttggtatc    300
attggtgaag acaaagaaaa gggtttgacc tacgttgctg aaccaattgg tgtcatctgt    360
ggtgtcactc caaccaccaa cccaacttct accaccatct tcaaggctat gattgccatc    420
aagactggta acccaattat tttcgctttc cacccatctg ctcaagaatc ttccaagaga    480
gctgctgaag ttgttttgga agctgccatg aaggctggtg ctccaaagga tatcatccaa    540
tggattgaag ttccatccat tgaagctacc aagcaattga tgaaccacaa gggtattgct    600
ttagtcttgg ctaccggtgg ttctggtatg gttaagtctg cttactccac tggtaaacca    660
gctttgggtg ttggtccagg taacgttcca tcttacatcg aaaagactgc tcatatcaag    720
cgtgctgtca acgatatcat cggttccaag actttcgata atggtatgat ctgtgcttct    780
gaacaagttg ttgtcattga caaggaaatc tacaaggatg tcaccaatga attcaaggct    840
caccaagctt acttcgtcaa gaaggacgaa ttacaaagat tagaaaacgc catcatgaac    900
gaacaaaaga ctggtatcaa gccagatatc gttggtaagt ctgctgttga aattgctgaa    960
ttggccggta tcccagttcc agaaaacacc aaattgatca ttgctgaaat ctccggtatg   1020
ggttctgact acccattgtc cagagaaaag ttgtctccag ttttggcttt agtcaaggct   1080
caatctacca agcaagcttt ccaaatctgt gaagacactt tgcacttcgg tggtttaggt   1140
cacactgctg ttatccacac tgaagacgaa actttgcaaa aggatttcgg tctaagaatg   1200
aaggcttgtc gtgttttggt caacactcca tctgctgttg gtggtatcgg tgacatgtac   1260
aacgaattga ttccatcctt gactttgggt tgtggttctt acggtagaaa ctccatctcc   1320
cacaacgtct ctgctaccga tttgttgaac atcaagacca ttgccaagag aagaaacaac   1380
actcaaatct tcaaggttcc agctcaaatc tatttcgaag aaaacgctat catgtccttg   1440
accaccatgg acaagattga aaaggtcatg atcgtttgtg acccaggtat ggttgaattt   1500
ggttacacca aaaccgtcga aaacgtctta cgtcaaagaa ctgaacaacc tcaaatcaag   1560
atcttctctg aagttgaacc aaatccatcc accaacactg tctacaaggg tttggaaatg   1620
atggtcgatt tccaaccaga caccatcatt gctttgggtg gtggttctgc catggatgct   1680
gccaaggcta tgtggatgtt cttcgaacat ccagaaactt cttcttcgg tgccaagcaa    1740
aaattcttgg acattggtaa gagaacctac aagattggta tgccagaaaa cgccactttc   1800
atctgtattc caaccacttc tggtactggt tctgaagtca ctccatttgc tgttatcact   1860
gactctgaaa ccaacgtcaa atacccattg gctgatttcg cttttgactcc agatgtcgcc  1920
atcattgacc ctcaatttgt catgtccgtc ccaaaatctg tcactgctga taccggtatg   1980
gacgttttga ttcacgctat ggaatcttac gtttctgtca tggcctccga ttacaccaga   2040
ggtttgtccc tacaagctat caaattgacc tttgaatact tgaaatcttc cgttgaaaaa   2100
ggtgacaagg tttccagaga aaagatgcac aacgcttcta ctttggccgg tatggccttt   2160
gctaacgctt tcttgggtat tgctcactcc attgctcaca aaattggtgg tgaatacggt   2220
attccacatg gtagagctaa cgccatcttg ttgcctcaca tcatcatgat caacgccaag   2280
gaccctcaaa agcacgcttt gttcccaaag tacgaatttc tcagagctga caccgattac   2340
gctgatatcg ccaagttctt aggtttgaaa ggtaacacca ctgaagcttt ggttgaatct   2400
ttggccaagg ctgtctacga attaggtcaa tctgttggta ttgaaatgaa cttgaaatct   2460
caaggtgtct ctgaagaaga attgaacgaa tccattgaca gaatggctga attggctttc   2520
gaagaccaat gtaccactgc caacccaaag gaagctttga tttctgaaat caaggatatc   2580
atccaaactt cttacgacta caagcag                                        2607

SEQ ID NO: 30          moltype = AA  length = 392
FEATURE                Location/Qualifiers
source                 1..392
                       mol_type = protein
                       organism = Clostridium acetobutylicum
SEQUENCE: 30
MKEVVIASAV RTAIGSYGKS LKDVPAVDLG ATAIKEAVKK AGIKPEDVNE VILGNVLQAG     60
LGQNPARQAS FKAGLPVEIP AMTINKVCGS GLRTVSLAAQ IIKAGDADVI IAGGMENMSR    120
APYLANNARW GYRMGNAKFV DEMITDGLWD AFNDYHMGIT AENIAERWNI SREEQDEFAL    180
ASQKKAEEAI KSGQFKDEIV PVVIKGRKGE TVVDTDEHPR FGSTIEGLAK LKPAFKKDGT    240
VTAGNASGLN DCAAVLVIMS AEKAKELGVK PLAKIVSYGS AGVDPAIMGY GPFYATKAAI    300
EKAGWTVDEL DLIESNEAFA AQSLAVAKDL KFDMNKVNVN GGAIALGHPI GASGARILVT    360
LVHAMQKRDA KKGLATLCIG GGQGTAILLE KC                                   392

SEQ ID NO: 31          moltype = AA  length = 282
FEATURE                Location/Qualifiers
source                 1..282
                       mol_type = protein
                       organism = Clostridium acetobutylicum
SEQUENCE: 31
MKKVCVIGAG TMGSGIAQAF AAKGFEVVLR DIKDEFVDRG LDFINKNLSK LVKKGKIEEA     60
TKVEILTRIS GTVDLNMAAD CDLVIEAAVE RMDIKKQIFA DLDNICKPET ILASNTSSLS    120
ITEVASATKR PDKVIGMHFF NPAPVMKLVE VIRGIATSQE TFDAVKETSI AIGKDPVEVA    180
EAPGFVVNRI LIPMINEAVG ILAEGIASVE DIDKAMKLGA NHPMGPLELG DFIGLDICLA    240
IMDVLYSETG DSKYRPHTLL KKYVRAGWLG RKSGKGFYDY SK                        282
```

```
SEQ ID NO: 32              moltype = AA  length = 261
FEATURE                    Location/Qualifiers
source                     1..261
                           mol_type = protein
                           organism = Clostridium acetobutylicum
SEQUENCE: 32
MELNNVILEK EGKVAVVTIN RPKALNALNS DTLKEMDYVI GEIENDSEVL AVILTGAGEK   60
SFVAGADISE MKEMNTIEGR KFGILGNKVF RRLELLEKPV IAAVNGFALG GGCEIAMSCD  120
IRIASSNARF GQPEVGLGIT PGFGGTQRLS RLVGMGMAKQ LIFTAQNIKA DEALRIGLVN  180
KVVEPSELMN TAKEIANKIV SNAPVAVKLS KQAINRGMQC DIDTALAFES EAFGECFSTE  240
DQKDAMTAFI EKRKIEGFKN R                                            261

SEQ ID NO: 33              moltype = AA  length = 379
FEATURE                    Location/Qualifiers
source                     1..379
                           mol_type = protein
                           organism = Clostridium acetobutylicum
SEQUENCE: 33
MDFNLTREQE LVRQMVREFA ENEVKPIAAE IDETERFPME NVKKMGQYGM MGIPFSKEYG   60
GAGGDVLSYI IAVEELSKVC GTTGVILSAH TSLCASLINE HGTEEQKQKY LVPLAKGEKI  120
GAYGLTEPNA GTDSGAQQTV AVLEGDHYVI NGSKIFITNG GVADTFVIFA MTDRTKGTKG  180
ISAFIIEKGF KGFSIGKVEQ KLGIRASSTT ELVFEDMIVP VENMIGKEGK GFPIAMKTLD  240
GGRIGIAAQA LGIAEGAFNE ARAYMKERKQ FGRSLDKFQG LAWMMADMDV AIESARYLVY  300
KAAYLKQAGL PYTVDAARAK LHAANVAMDV TTKAVQLFGG YGYTKDYPVE RMMRDAKITE  360
IYEGTSEVQK LVISGKIFR                                               379

SEQ ID NO: 34              moltype = AA  length = 858
FEATURE                    Location/Qualifiers
source                     1..858
                           mol_type = protein
                           organism = Clostridium acetobutylicum
SEQUENCE: 34
MKVTNQKELK QKLNELREAQ KKFATYTQEQ VDKIFKQCAI AAAKERINLA KLAVEETGIG   60
LVEDKIIKNH FAAEYIYNKY KNEKTCGIID HDDSLGITKV AEPIGIVAAI VPTTNPTSTA  120
IFKSLISLKT RNAIFFSPHP RAKKSTIAAA KLILDAAVKA GAPKNIIGWI DEPSIELSQD  180
LMSEADIILA TGGPSMVKAA YSSGKPAIGV GAGNTPAIID ESADIDMAVS SIILSKTYDN  240
GVICASEQSI LVMNSIYEKV KEEFVKRGSY ILNQNEIAKI KETMFKNGAI NADIVGKSAY  300
IIAKMAGIEV PQTTKILIGE VQSVEKSELF SHEKLSPVLA MYKVKDFDEA LKKAQRLIEL  360
GGSGHTSSLY IDSQNNKDKV KEFGLAMKTS RTFINMPSSQ GASGDLYNFA IAPSFTLGCG  420
TWGGNSVSQN VEPKHLLNIK SVAERRENML WFKVPQKIYF KYGCLRFALK ELKDMNKKRA  480
FIVTDKDLFK LGYVNKITKV LDEIDIKYSI FTDIKSDPTI DSVKKGAKEM LNFEPDTIIS  540
IGGGSPMDAA KVMHLLYEYP EAEIENLAIN FMDIRKRICN FPKLGTKAIS VAIPTTAGTG  600
SEATPFAVIT NDETGMKYPL TSYELTPNMA IIDTELMLNM PRKLTAATGI DALVHAIEAY  660
VSVMATDYTD ELALRAIKMI FKYLPRAYKN GTNDIEAREK MAHASNIAGM AFANAFLGVC  720
HSMAHKLGAM HHVPHGIACA VLIEEVIKYN ATDCPTKQTA FPQYKSPNAK RKYAEIAEYL  780
NLKGTSDTEK VTALIEAISK LKIDLSIPQN ISAAGINKKD FYNTLDKMSE LAFDDQCTTA  840
NPRYPLISEL KDIYIKSF                                                858

SEQ ID NO: 35              moltype = AA  length = 862
FEATURE                    Location/Qualifiers
source                     1..862
                           mol_type = protein
                           organism = Clostridium acetobutylicum
SEQUENCE: 35
MKVTTVKELD EKLKVIKEAQ KKFSCYSQEM VDEIFRNAAM AAIDARIELA KAAVLETGMG   60
LVEDKVIKNH FAGEYIYNKY KDEKTCGIIE RNEPYGITKI AEPIGVVAAI IPVTNPTSTT  120
IFKSLISLKT RNGIFFSPHP RAKKSTILAA KTILDAAVKS GAPENIIGWI DEPSIELTQY  180
LMQKADITLA TGGPSLVKSA YSSGKPAIGV GPGNTPVIID ESAHIKMAVS SIILSKTYDN  240
GVICASEQSV IVLKSIYNKV KDEFQERGAY IIKKNELDKV REVIFKDGSV NPKIVGQSAY  300
TIAAMAGIKV PKTTRILIGE VTSLGEEEPF AHEKLSPVLA MYEADNFDDA LKKAVTLINL  360
GGLGHTSGIY ADEIKARDKI DRFSSAMKTV RTFVNIPTSQ GASGDLYNFR IPPSFTLGCG  420
FWGGNSVSEN VGPKHLLNIK TVAERRENML WFRVPHKVYF KFGCLQFALK DLKDLKKKRA  480
FIVTDSDPYN LNYVDSIIKI LEHLDIDFKV FNKVGREADL KTIKKATEEM SSFMPDTIIA  540
LGGTPEMSSA KLMWVLYEHP EVKFEDLAIK FMDIRKRIYT FPKLGKKAML VAITTSAGSG  600
SEVTPFALVT DNNTGNKYML ADYEMTPNMA IVDAELMMKM PKGLTAYSGI DALVNSIEAY  660
TSVYASEYTN GLALEAIRLI FKYLPEAYKN GRTNEKAREK MAHASTMAGM ASANAFLGLC  720
HSMAIKLSSE HNIPSGIANA LLIEEVIKFN AVDNPVKQAP CPQYKYPNTI FRYARIADYI  780
KLGGNTDEEK VDLLINKIHE LKKALNIPTS IKDAGVLEEN FYSSLDRISE LALDDQCTGA  840
NPRFPLTSEI KEMYINCFKK QP                                           862

SEQ ID NO: 36              moltype = AA  length = 389
FEATURE                    Location/Qualifiers
source                     1..389
                           mol_type = protein
                           organism = Clostridium acetobutylicum
SEQUENCE: 36
MLSFDYSIPT KVFFGKGKID VIGEEIKKYG SRVLIVYGGG SIKRNGIYDR ATAILKENNI   60
AFYELSGVEP NPRITTVKKG IEICRENNVD LVLAIGGGSA IDCSKVIAAG VYYDGDTWDM  120
```

```
VKDPSKITKV LPIASILTLS ATGSEMDQIA VISNMETNEK LGVGHDDMRP KFSVLDPTYT   180
FTVPKNQTAA GTADIMSHTF ESYFSGVEGA YVQDGIAEAI LRTCIKYGKI AMEKTDDYEA   240
RANLMWASSL AINGLLSLGK DRKWSCHPME HELSAYYDIT HGVGLAILTP NWMEYILNDD   300
TLHKFVSYGI NVWGIDKNKD NYEIAREAIK NTREYFNSLG IPSKLREVGI GKDKLELMAK   360
QAVRNSGGTI GSLRPINAED VLEIFKKSY                                     389

SEQ ID NO: 37              moltype = AA   length = 390
FEATURE                    Location/Qualifiers
source                     1..390
                           mol_type = protein
                           organism = Clostridium acetobutylicum
SEQUENCE: 37
MVDFEYSIPT RIFFGKDKIN VLGRELKKYG SKVLIVYGGG SIKRNGIYDK AVSILEKNSI   60
KFYELAGVEP NPRVTTVEKG VKICRENGVE VVLAIGGGSA IDCAKVIAAA CEYDGNPWDI   120
VLDGSKIKRV LPIASILTIA ATGSEMDTWA VINNMDTNEK LIAAHPDMAP KFSILDPTYT   180
YTVPTNQTAA GTADIMSHIF EVYFSNTKTA YLQDRMAEAL LRTCIKYGGI ALEKPDDYEA   240
RANLMWASSL AINGLLTYGK DTNWSVHLME HELSAYYDIT HGVGLAILTP NWMEYILNND   300
TVYKFVEYGV NVWGIDKEKN HYDIAHQAIQ KTRDYFVNVL GLPSRLRDVG IEEEKLDIMA   360
KESVKLTGGT IGNLRPVNAS EVLQIFKKSV                                    390

SEQ ID NO: 38              moltype = AA   length = 336
FEATURE                    Location/Qualifiers
source                     1..336
                           mol_type = protein
                           organism = Clostridium acetobutylicum
SEQUENCE: 38
MNKADYKGVW VFAEQRDGEL QKVSLELLGK GKEMAEKLGV ELTAVLLGHN TEKMSKDLLS   60
HGADKVLAAD NELLAHFSTD GYAKVICDLV NERKPEILFI GATFIGRDLG PRIAARLSTG   120
LTADCTSLDI DVENRDLLAT RPAFGGNLIA TIVCSDHRPQ MATVRPGVFE KLPVNDANVS   180
DDKIEKVAIK LTASDIRTKV SKVVKLAKDI ADIGEAKVLV AGGRGVGSKE NFEKLEELAS   240
LLGGTIAASR AAIEKEWVDK DLQVGQTGKT VRPTLYIACG ISGAIQHLAG MQDSDYIIAI   300
NKDVEAPIMK VADLAIVGDV NKVVPELIAQ VKAANN                             336

SEQ ID NO: 39              moltype = AA   length = 259
FEATURE                    Location/Qualifiers
source                     1..259
                           mol_type = protein
                           organism = Clostridium acetobutylicum
SEQUENCE: 39
MNIVVCLKQV PDTAEVRIDP VKGTLIREGV PSIINPDDKN ALEEALVLKD NYGAHVTVIS   60
MGPPQAKNAL VEALAMGADE AVLLTDRAFG GADTLATSHT IAAGIKKLKY DIVFAGRQAI   120
DGDTAQVGPE IAEHLGIPQV TYVEKVEVDG DTLKIRKAWE DGYEVVEVKT PVLLTAIKEL   180
NVPRYMSVEK IFGAFDKEVK MWTADDIDVD KANLGLKGSP TKVKKSSTKE VKGQGEVIDK   240
PVKEAAAYVV SKLKEEHYI                                                259

SEQ ID NO: 40              moltype = DNA   length = 5976
FEATURE                    Location/Qualifiers
misc_feature               1..5976
                           note = plasmid YEplac112PtdhTadh
source                     1..5976
                           mol_type = other DNA
                           organism = synthetic construct
SEQUENCE: 40
gcccggggga tccactagtt ctagaatccg tcgaaactaa gttctggtgt tttaaaacta   60
aaaaaagac taactataaa agtagaattt aagaagttta agaaatagat ttacagaatt    120
acaatcaata cctaccgtct ttatatactt attagtcaag taggggaata atttcaggga   180
actggtttca acctttttt tcagctttt ccaaatcaga gagagcagaa ggtaatagaa    240
ggtgtaagaa aatgagatag atacatgcgt gggtcaattg ccttgtgtca tcatttactc   300
caggcaggtt gcatcactcc attgaggttg tgcccgtttt ttgcctgttt gtgccctgt    360
tctctgtagt tgcgctaaga gaatggacct atgaactgat ggttggtgaa gaaaacaata   420
ttttggtgct gggattcttt tttttctgg atgccagctt aaaaagcggg ctccattata   480
tttagtggat gccaggaata aactgttcac ccagacacct acgatgttat atattctgtg   540
taacccgccc cctatttggg gcatgtacgg gttacagcag aattaaaagg ctaatttttt   600
gactaaataa agttaggaaa atcactacta ttaattaatt acgtattctt tgaaatggcg   660
agtattgata atgataaact gagctcgaat tcactggccg tcgttttaca acgtcgtgac   720
tgggaaaacc ctggcgttac ccaacttaat cgccttgcag cacatccccc tttcgccagc   780
tggcgtaata gcgaagaggc ccgcaccgat cgcccttccc aacagttgcg cagcctgaat   840
ggcgaatggc gcctgatgcg gtattttctc cttacgcatc tgtgcggtat ttcacaccgc   900
atatatcgta tcgtacttgt tacccatcat tgaattttga acatccgaac ctgggagttt   960
tccctgaaac agatagtata tttgaacctg tataataata tatagtctag cgctttacgg   1020
aagacaatgt atgtatttcg gttcctggag aaactattgc atctattgca taggtaatct   1080
tgcacgtcgc atccccggtt cattttctgc gtttccatct tgcacttcaa tagcatatct   1140
ttgttaacga agcatctgtg cttcattttg tagaacaaaa atgcaacgcg agagcgctaa   1200
tttttcaaac aaagaatctg agctgcattt ttacagaaca gaaataaagc aaaggaacga    1260
tattttacca acgaagaatc tgtgcttcat ttttgtaaaa caaaaatgca acgcgagagc   1320
gctaattttt caaacaaaga atctgagctg catttttaca aacagaaat gcaacgcgag   1380
agcgctattt taccaacaaa gaatctatac ttcttttttg ttctacaaaa atgcatcccg   1440
agagcgctat ttttctaaca aagcatctta gattactttt tttctccttt gtgcgctcta   1500
taatgcagtc tcttgataac ttttttgcact gtaggtccgt taaggttaga agaaggctac   1560
```

```
tttggtgtct attttctctt ccataaaaaa agcctgactc cacttcccgc gtttactgat    1620
tactagcgaa gctgcgggtg cattttttca agataaaggc atccccgatt atattctata    1680
ccgatgtgga ttgcgcatac tttgtgaaca gaaagtgata gcgttgatga ttcttcattg    1740
gtcagaaaat tatgaacggt ttcttctatt ttgtctctat atactacgta taggaaatgt    1800
ttacattttc gtattgtttt cgattcactc tatgaatagt tcttactaca atttttttgt    1860
ctaaagagta atactagaga taaacataaa aaatgtagag gtcgagttta gatgcaagtt    1920
caaggagcga aaggtggatg ggtaggttat atagggatat agcacagaga tatatagcaa    1980
agagatactt ttgagcaatg tttgtggaag cggtattcgc aatattttag tagctcgtta    2040
cagtccggtg cgttttttggt tttttgaaag tgcgtcttca gagcgctttt ggtttttcaaa    2100
agcgctctga agttcctata ctttctagct agagaatagg aacttcggaa taggaacttc    2160
aaagcgtttc cgaaaacgag cgcttccgaa aatgcaacgc gagctgcgca catacagctc    2220
actgttcacg tcgcacctat atctgcgtgt tgcctgtata tatatataca tgagaagaac    2280
ggcatagtgc gtgtttatgc ttaaatgcgt acttatatgc gtctatttat gtaggatgaa    2340
aggtagtcta gtacctcctg tgatattatc ccattccatg cggggtatcg tatgcttcct    2400
tcagcactac cctttagctg ttctatatgc tgccactcct caattggatt agtctcatcc    2460
ttcaatgcta tcatttcctt tgatattgga tcgatccgat gataagctgt caaacatgag    2520
aattgatctt ttatgcttgc ttttcaaaag gcttgcaggc aagtgcacaa acaatactta    2580
aataaatact actcagtaat aacctatttc ttagcatttt tgacgaaatt tgctattttg    2640
ttagagtctt ttacaccatt tgtctccaca cctccgctta catcaacacc aataacgcca    2700
tttaatctaa gcgcatcacc aacattttct ggcgtcagtc caccagctaa cataaaatgt    2760
aagctctcgg ggctctcttg ccttccaacc cagtcagaaa tcgagttcca atccaaaagt    2820
tcacctgtcc cacctgcttc tgaatcaaac aagggaataa acgaatgagg tttctgtgaa    2880
gctgcactga gtagtatgtt gcagtctttt ggaaatacga gtcttttaat aactggcaaa    2940
ccgaggaact cttggtattc ttgccacgac tcatctccat gcagttggac gatatcaatg    3000
ccgtaatcat tgaccagagc caaaacatcc tccttaggtt gattacgaaa cacgccaacc    3060
aagtatttcg gagtgcctga actattttta tatgctttta caagacttga aattttcctt    3120
gcaataaccg ggtcaattgt tctctttcta ttgggcacac atataatacc cagcaagtca    3180
gcatcggaat ctagtgcaca ttctgcggcc tctgtgctct gcaagccgca aactttcacc    3240
aatgaccag aactacctgt gaaattaata acagacatac tccaagctgc ctttgtgtgc    3300
ttaatcacgt atactcacgt gctcaatagt caccaatgcc ctccctcttg gccctctcct    3360
tttctttttt cgaccgaatt aattcttgaa gacgaaaggg cctcgtgata cgcctatttt    3420
tataggttaa tgtcatgata ataatggttt cttagacgtc aggtggcact tttcggggaa    3480
atgtgcgcgg aaccccatt tgtttatttt tctaaataca ttcaaatatg tatccgctca    3540
tgagacaata accctgataa atgcttcaat aatattgaaa aaggaagagt atgagtattc    3600
aacatttccg tgtcgccctt attcccttttt ttgcggcatt ttgccttcct gtttttgctc    3660
acccagaaac gctggtgaaa gtaaaagatg ctgaagatca gttgggtgca cgagtgggtt    3720
acatcgaact ggatctcaac agcggtaaga tccttgagag ttttcgcccc gaagaacgtt    3780
ttccaatgat gagcactttt aaagttctgc tatgtggcgc ggtattatcc cgtattgacg    3840
ccgggcaaga gcaactcggt cgccgcatac actattctca gaatgacttg gttgagtact    3900
caccagtcac agaaaagcat cttacggatg gcatgacagt aagagaatta tgcagtgctg    3960
ccataaccat gagtgataac actgcggcca acttacttct gacaacgatc ggaggaccga    4020
aggagctaac cgcttttttg cacaacatgg gggatcatgt aactcgcctt gatcgttggg    4080
aaccggagct gaatgaagcc ataccaaacg acgagcgtga caccacgatg cctgtagcaa    4140
tggcaacaac gttgcgcaaa ctattaactg gcgaactact tactctagct tcccggcaac    4200
aattaataga ctggatggag gcggataaag ttgcaggacc acttctgcgc tcggcccttc    4260
cggctggctg gtttattgct gataaatctg gagccggtga gcgtgggtct cgcggtatca    4320
ttgcagcact ggggccagat ggtaagccct cccgtatcgt agttatctac acgacgggga    4380
gtcaggcaac tatggatgaa cgaaatagac agatcgctga gataggtgcc tcactgatta    4440
agcattggta actgtcagac caagtttact catatatact ttagattgat ttaaaacttc    4500
atttttaatt taaaaggatc taggtgaaga tcctttttga taatctcatg accaaaatcc    4560
cttaacgtga gttttcgttc cactgagcgt cagaccccgt agaaaagatc aaaggatctt    4620
cttgagatcc tttttttctg cgcgtaatct gctgcttgca acaaaaaaa ccaccgctac    4680
cagcggtggt ttgtttgccg gatcaagagc taccaactct ttttccgaag gtaactggct    4740
tcagcagagc gcagatacca aatactgtcc ttctagtgta gccgtagtta ggccaccact    4800
tcaagaactc tgtagcaccg cctacatacc tcgctctgct aatcctgtta ccagtggctg    4860
ctgccagtgg cgataagtcg tgtcttaccg ggttggactc aagacgatag ttaccggata    4920
aggcgcagcg tcgggctgaa acggggggtt cgtgcacaca gcccagcttg gagcgaacga    4980
cctacaccga actgagatac ctacagcgtg agctatgaga aagcgccacg cttcccgaag    5040
ggagaaaggc ggacaggtat ccggtaagcg gcagggtcgg aacaggagag cgcacgaggg    5100
agcttccagg gggaaacgcc tggtatcttt atagtcctgt cgggtttcgc cacctctgac    5160
ttgagcgtcg atttttgtga tgctcgtcag ggggcggag cctatggaaa aacgccagca    5220
acgcggcctt tttacggttc ctggcctttt gctggccttt tgctcacatg ttctttcctg    5280
cgttatcccc tgattctgtg gataaccgta ttaccgcctt tgagtgagct gataccgctc    5340
gccgcagccg aacgaccgag cgcagcgagt cagtgagcga ggaagcggaa gagcgcccaa    5400
tacgcaaacc gcctctcccc gcgcgttggc cgattcatta atgcagctgg cacgacaggt    5460
ttcccgactg gaaagcgggc agtgagcgca acgcaattaa tgtgagttag ctcactcatt    5520
aggcaccca ggctttacac tttatgcttc cggctcgtat gttgtgtgga attgtgagcg    5580
gataacaatt tcacacagga aacagctatg accatgatta cgccaagctt aggcctgtgt    5640
ggaagaacga ttacaacagg tgttgtcctc tgaggacata aaatacacac cgagattcat    5700
caactcattg ctggagttag catatctaca attgggtgaa atggggagcg atttgcaggc    5760
atttgctcgg catgccggta gaggtgtggt caataagagc gacctcatgc tatacctgag    5820
aaagcaacct gacctacagg aaagagttac tcaagaataa gaattttcgt tttaaaacct    5880
aagagtcact ttaaaatttg tatacactta tttttttat aacttattta ataataaaaa    5940
tcataaatca taagaaattc gctcgagtcg actgca                             5976
```

SEQ ID NO: 41          moltype = DNA   length = 13286
FEATURE                Location/Qualifiers
misc_feature           1..13286
                       note = pBOL34

```
source                  1..13286
                        mol_type = other DNA
                        organism = synthetic construct
SEQUENCE: 41
aagcttgcat gcctgcaggt cgacggcgcg ccgggcccgt ttaaacggcc ggccaaggtg   60
agacgcgcat aaccgctaga gtactttgaa gaggaaacag caataggggt gctaccagta   120
taaatagaca ggtacataca acactggaaa tggttgtctg tttgagtacg ctttcaattc   180
atttgggtgt gcactttatt atgttacaat atggaaggga actttacact tctcctatgc   240
acatatatta attaaagtcc aatgctagta gagaaggggg gtaacacccc tccgcgctct   300
tttccgattt ttttctaaac cgtggaatat ttcggatatc cttttgttgt ttccgggtgt   360
acaatatgga cttcctcttt tctgcaacc aaacccatac atcgggattc ctataatacc   420
ttcgttggtc tccctaacat gtaggtggcg gagggagat atacaataga acagatacca   480
gacaagacat aatgggctaa acaagactac accaattaca ctgcctcatt gatggtggta   540
cataacgaac taatactgta gccctagact tgatagccat catcatatcg aagtttcact   600
acccttttc catttgccat ctattgaagt aataataggc gcatgcaact tcttttcttt   660
ttttttcttt tctctctccc ccgttgttgt ctcaccatat ccgcaatgac aaaaaaatga   720
tggaagacac taaaggaaaa aattaacgac aaagacagca ccaacagatg tcgttgttcc   780
agagctgatg aggggtatct cgaagcacac gaaacttttt ccttccttca ttcacgcaca   840
ctactctcta atgagcaacg gtatacggcc ttccttccag ttacttgaat ttgaaataaa   900
aaaaagtttg ctgtcttgct atcaagtata aatagacctg caattattaa tcttttgttt   960
cctcgtcatt gttctcgttc cctttcttcc ttgtttcttt ttctgcacaa tatttcaagc   1020
tataccaagc atacaatcaa tcatctcata tacaatgaag gaagttgtta ttgcttctgc   1080
tgtcagaact gccattggtt cttacggtaa gtctttgaag gacgtccag ctgtcgactt   1140
gggtgctacc gccatcaagg aagctgtcaa gaaggctggt atcaagccag aagatgttaa   1200
cgaagttatc ttaggtaacg ttttgcaagc tggtttaggt caaaacccag ctcgtcaagc   1260
ttctttcaag gctggtttgc cagttgaaat tccagccatg accatcaaca aggtttgtgg   1320
ttctggtttg agaactgttt ctttggctgc tcaaatcatc aaggctggtg acgctgatgt   1380
catcattgct ggtggtatgg aaaacatgtc cagagctcca tacttggcta caatgctag   1440
atggggttac agaatgggta acgccaagtt cgtcgatgaa atgatcactg acggtttatg   1500
ggacgctttc aacgactacc acatgggtat cactgctgca aacattgctg aaagatggaa   1560
catctccaga gaagaacaag atgaatttgc tttggcttct caaaagaagg ctgaagaagc   1620
catcaaatct ggtcaattca aggacgaaat tgtcccagtt gtcatcaagg gtagaaaggg   1680
tgaaaccgtt gtcgacaccg atgaacaccc aagattcggt tccaccattg aaggtttggc   1740
caagttgaaa ccagctttca agaaggatgg taccgtcact gctggtaacg cttccggttt   1800
gaacgactgt gctgctgttt tggttatcat gtctgctgaa aaggccaagg aattgggtgt   1860
caagccattg gccaagattg tctcctacgg ttctgctggt gttgacccag ccatcatggg   1920
ttacggtcct ttctacgcta ccaaggctgc tatcgaaaag gctggttgga ccgttgacga   1980
attggatttg attgaatcca acgaagcttt cgctgctcaa tctttggctg ttgccaagga   2040
cttgaaattc gacatgaaca aggtcaacgt taacggtggt gccatcgctt ggggtcaccc   2100
aattggtgct tccggtgcca gaatcttggt tactttagtc cacgctatgc aaaagcgtga   2160
tgccaagaag ggtttggcta ctctatgtat cggtggtggt caaggtactg ccatcttatt   2220
ggaaaagtgt taggcccggg cataaagcaa tcttgatgag gataatgatt tttttttgaa   2280
tatacataaa tactaccgtt tttctgctag attttgtgaa gacgtaaata agtacatatt   2340
acttttaag ccaagacaag attaagcatt aactttaccc ttttctcttc taagtttcaa   2400
tactagttat cactgtttaa aagttatggc gagaacgtcg gcggtaaaa tatattaccc   2460
tgaacgtggt gaattgaagt tctaggatgg tttaaagatt tttcctttt gggaaataag   2520
taaacaatat attgctgcct ttgcaaaacg cacatacccca caatatgtga ctattggcaa   2580
agaacgcatt atcctttgaa gaggtggata ctgatactaa gagagtctct attccggctc   2640
cactttagt ccagagatta cttgtcttct tacgtatcag aacaagaaag catttccaaa   2700
gtaattgcat ttgcccttga gcagtatata tatactaaga agtttaaaca tttaaacgtg   2760
tgtgtgcatt atatatatta aaaattaaga attagactaa ataaagtgtt tctaaaaaaa   2820
tattaaagtt gaaatgtgcg tgttgtgaat tgtgctctat tagaataatt atgacttgtg   2880
tgcgtttcat attttaaaat aggaaataac caagaaagaa aaagtaccat ccagagaaac   2940
caattatatc aaatcaaata aaacaaccag cttcggtgtg tgtgtgtgtg tgaagctaag   3000
agttgatgcc atttaatcta aaaattttaa ggtgtgtgtg tggataaaat attagaatga   3060
caattcgaga tgaaatttta agcaaactct agtaggaaat aagcggctta ttcttgttgg   3120
ctcctaattc tttttagtgt atcagttccc attgataaaa aaattaaaat taaaattaga   3180
aaaattaaac cagaaaaatc aagttgatta aaatgtgaca aaaattatga ttaaatgcta   3240
cttcaacagg agcccgggcc tatttggagt agtcgtagaa acccttacca gactttctac   3300
ctaaccaacc agctctaacg tacttcttca ataaagtgtg aggtctgtac ttagagtcac   3360
cggtttcaga gtataagaca tccatgatgg ccaaacagat atccaaaccg atgaagtcac   3420
ctaattccaa tggacccatt gggtggttag cacccaattt catggccttg tcgatatctt   3480
caacagaagc aataccttca gccaaaatac cgacagcttc gttgatcatt ggaatcaaga   3540
ttctgttgac aacgaaacct ggagcttcag caacttcaac tggttccttca ccaatggcaa   3600
tggaagtttc cttgacagca tcgaaagttt cttgagaggt ggcaataccct ctgatgactt   3660
cgaccaactt catgactgga gctggttga agaagtgcat accgataacc ttgtctggtc   3720
tcttggtagc agaagcaact tcagtgatgg acaaagaaga agtgttggaa gccaaaatgg   3780
tttctggctt acagatgttg tccaaatcag caaagatttg cttcttgatg tccattcttt   3840
caacggcagc ttcaatgacc aaatcacagt cagcagccat gttcaagtca acagtaccgg   3900
agattctggt caagatttcg accttggtag cttcttcaat cttacccttc ttgaccaact   3960
tggacaagtt cttgttgatg aaatccaaac cacggtcaac gaattcgtcc ttgatatctc   4020
tcaaaacaac ttcgaaaccc ttggcagcga aagcttgagc aataccagaa cccatggtac   4080
cggcaccaat gacacaaacc ttcttcattt tgatttagtt tttgtgtgtt gataagcagt   4140
tgcttggttt tttatgaaaa atagctagaa ggaataaggg attacaagag agatgttaca   4200
agaaagaagt aaaataaatt tgattaatat tgccattatc aaaagctatt tatatgttga   4260
aatcgtggag atcatgtgtg ccagaaaagg ccacagtttc cggggagagg catacccttga   4320
ggtggctagg aatcacggag acctcttgac ttgcagggta ggctagctag aattaagtga   4380
ggtgacaagg tttccataca gttttgacct tgagacgttg ctacttacga tttgcagtat   4440
gcaagtctca tgctgcaaac aaaagaggac cgctcaggta atcgctcaat tagtggacgt   4500
```

-continued

```
tatcaggggc gggagaggcg aaagtggttt ttggtggtgt aagtaaaggt cgtccaaata  4560
tgcaggtgtt tgggtgctat cctagtggaa gctcggatca gtagataacc cgcctagaag  4620
cggtatttt cttttttttt cttccttctt tttcgtcatt atttcaaacg cttttgcgtc  4680
aagtaatgaa tatctggcgg ttccgcggta atgcgacaat ttgtgatatg cactcttaaa  4740
accccgccac gatgatcgca cgtgccggca tttatagacg actttctgg ttgtcccgct  4800
tcacggcaca tgcatgcatc aatgaccgaa ttcaggttgc tactaaccat tgtgttgtgt  4860
tattgctgtg catgaggtgc tcaagtgccc gcggcatctg actagtggta actctagacg  4920
gcttcgatgc agagagttcc tcaaaatttt tcttttcaat tgtttgcctg gtttccgcgg  4980
cgtatatcag tttttggcga tatggtaacg cgatactcta cggcaccttc acggtagatg  5040
tcttttttaa aagtgactgt taattccagg attgaaagga agtgtcgaat agtatagtat  5100
gcttctagg ccggccgttt aaatgggccc gcggcccgtt taaacggccg gcccttccct  5160
tttacagtgc ttcggaaaag cacagcgttg tccaagggaa caattttct tcaagttaat  5220
gcataagaaa tatctttttt tatgtttagc taagtaaaag cagcttggag taaaaaaaa  5280
aatgagtaaa tttctcgatg gattagtttc tcacaggtaa cataacaaaa accaagaaaa  5340
gcccgcttct gaaaactaca gttgacttgt atgctaaagg gccagactaa tgggaggaga  5400
aaaagaaacg aatgtatatg ctcatttaca ctctatatca ccatatggag gataagttgg  5460
gctgagcttc tgatccaatt tattctatcc attagttgct gatatgtccc accagccaac  5520
acttgatagt atctactcgc cattcacttc cagcagcgcc agtagggttg ttgagcttag  5580
taaaaatgtg cgcaccacaa gcctacatga ctccacgtca catgaaacca caccgtgggg  5640
ccttgttgcg ctaggaatag gatatgcgac gaagacgctt ctgcttagta accacaccac  5700
attttcaggg ggtcgatctg cttgcttcct ttactgtcac gagcggccca taatcgcgct  5760
tttttttaa aaggcgcgag acagcaaaca ggaagctcgg gtttcaacct tcggagtggt  5820
cgcagatctg gagactggat ctttacaata cagtaaggca agccaccatc tgcttcttag  5880
gtgcatgcga cggtatccac gtgcagaaca acatagtctg aagaaggggg ggaggagcat  5940
gttcattctc tgtagcagta agagcttggt gataatgacc aaaactggag tctcgaaatc  6000
atataaatag acaatatatt ttcacacaat gagatttgta gtacagttct attctctctc  6060
ttgcataaat aagaaattca tcaagaactt ggtttgatat ttcaccaaca cacacaaaaa  6120
acagtacttc actaaatttta cacacaaaac aaaatggaat tgaacaacgt tatcttggaa  6180
aaggaaggta aggttgccgt tgtcaccatc aacagaccaa aggctttgaa tgctttgaac  6240
tctgacactt tgaaggaaat ggactacgtc attggtgaaa ttgaaaacga ttctgaagtt  6300
ttggctgtca tcttgaccgg tgccggtgaa aagtctttcg ttgctggtgc tgatatctct  6360
gaaatgaagg aaatgaacac cattgaaggt agaaagttcg gtatcttagg taacaaggtt  6420
ttcagaagat tggaattgtt ggaaaagcca gtcattgctg ctgtcaacgg tttcgctttg  6480
ggtggtggtt gtgaaattgc catgtcctgt gacatcagaa ttgcttcttc taacgctcgt  6540
ttcggtcaac cagaagtcgg tctaggtatc actccaggtt tcggtggtac tcaaagatta  6600
tccagattgg ttggtatggg tatggccaag caattgatct tcaccgctca aaacatcaag  6660
gctgacgaag ctttgagaat tggtttagtc aacaaggttg ttgaaccatc tgaattgatg  6720
aacactgcca aggaaattgc taacaagatc gtctccaacg ctccagttgc tgtcaaattg  6780
tccaagcaag ccatcaacag aggtatgcaa tgtgatatcg acaccgcttt ggcctttgaa  6840
tctgaagctt tcggtgaatg tttctccact gaagaccaaa aggatgctat gaccgctttc  6900
atcgaaaaga gaaagattga aggtttcaag aacaggtgat gagcccgggc gcgaatttct  6960
tatgatttat gattttatt attaaataag ttataaaaaa aataagtgta tacaaatttt  7020
aaagtgactc ttaggtttta aaacgaaaat tcttattctt gagtaactct ttcctgtagg  7080
tcaggttgct ttctcaggta tagcatgagg tcgctcttat tgaccacacc tctaccggca  7140
tgccgagcaa atgcctgcaa atcgctcccc atttcaccca attgtagata tgctaactcc  7200
agcaatgagt tgatgaatct cggtgtgtat tttatgtcct cagaggacaa cacctgttgt  7260
aatcgttctt ccacacggat ccacagccta gccttcagtt gggctctatc ttcatcgtca  7320
ttcattgcat ctactagccc cttacctgag cttcaagacg ttatatcgct tttatgtatc  7380
atgatcttat cttgagatat gaatacataa atatatttac tcaagtgtat acgtgcatgc  7440
ttttttttacg gtttaaacat ttaaatgggc cgctctagag gatccccggg taccgagctc  7500
gggcccacgcg ctactagttc cggtaatttg aaaacaaacc cggtctcgaa gcggagatcc  7560
ggcgataatt accgcagaaa taaacccata cacgagacgt agaaccagcc gcacatggcc  7620
ggagaaactc ctgcgagaat ttcgtaaact cgcgcgcatt gcatctgtat ttcctaatgc  7680
ggcacttcca ggcctcgaga cctctgacat gctttgaca ggaatagaca ttttcagaat  7740
gttatccata tgcctttcgg gtttttttcc ttccttttcc atcatgaaaa atctctcgag  7800
accgtttatc cattgctttt ttgttgtctt tttccctcgt tcacagaaag tctgaagaag  7860
ctatagtaga actatgagct tttttttgttt ctgttttcct tttttttttt tttacctctg  7920
tggaaattgt tactctcaca ctctttagtt cgtttgtttg ttttgtttat tccaattatg  7980
accggtgacg aaacgtggtc gatggtgggt accgcttatg ctcccctcca ttagtttcga  8040
ttatataaaa aggccaaata ttgtattatt ttcaaatgtc ctatcattat cgtctaacat  8100
ctaatttctc ttaaattttt tctctttctt tcctataaca ccaatagtga aaatctttt  8160
ttcttctata tctacaaaaa cttttttttt ctatcaacct cgttgataaa ttttttcttt  8220
aacaatcgtt aataattaat taattggaaa ataaccattt tttctctctt ttatacacac  8280
attcaaaaga aagaaaaaaa atatacccca gctagttaaa gaaaatcatt gaaaagaata  8340
agaagataag aaagatttaa ttatcaaaca atatcaatat gcctcaatcc tgggaagaac  8400
tggccgctga taagcgcgcc cgcctcgcaa aaaccatccc tgatgaatgg aaagtccaga  8460
cgctgcctgc ggaagacagc gttattgatt cccaaagaa atcgggggatc ctttcagagg  8520
ccgaactgaa gatcacagag gcctccgctg cagatcttgt gtccaagctg gcggccggag  8580
agttgacctc ggtggaagtt acgctagcat tctgtaaacg ggcagcaatc gcccagcagt  8640
taacaaactg cgcccacgag ttcttccctg acgccgctct cgcgcaggca agggaactcg  8700
atgaatacta cgcaaagcac aagagacccg ttggtccact ccatgcctc cccatctctc  8760
tcaaagacca gcttcgagtc aagggctacg aaacatcaat gggctacatc tcatggctaa  8820
acaagtacga cgaagggggac tcggttctga caaccatgcc ccgcaaagcc ggtgccgtct  8880
tctacgtcaa gacctctgtc ccgcagacc tgatggtcgt ggcgcaagtc aacaacatca  8940
tcgggcgcac cgtcaaccca cgcaacaaga actggtcgtg cggcggcagt tctggtggtg  9000
agggtcgcat cgttgggatt cgtggtggcg tcatcggtgt aggaacggat atcggtggct  9060
cgattcgagt gccggccgcg ttcaacttcc tgtacggtct aaggccgagt catgggcggc  9120
tgccgtatgc aaagatggcg aacagcatgg agggtcagga cacggtgcac agcgttgtcg  9180
ggccgattac gcactctgtt gaggacctcc gcctcttcac caaatccgtc ctcggtcagg  9240
```

-continued

```
agccatggaa atacgactcc aaggtcatcc ccatgccctg gcgccagtcc gagtcggaca      9300
ttattgcctc caagatcaag aacgcgggc tcaatatcgg ctactacaac ttcgacggca      9360
atgtccttcc acaccctcct atcctgcgcg gcgtggaaac caccgtcgcc gcactcgcca      9420
aagccggtca caccgtgacc ccgtggacgc catacaagca cgatttcggc cacgatctca      9480
tctcccatat ctacgcggct gacggcagcg ccgacgtaat gccgcgatatc agtgcatccg      9540
gcgagccggc gattccaaat atcaaagacc tactgaaccc gaacatcaaa gctgttaaca      9600
tgaacgagct ctgggacacg catctccaga agtggaatta ccagatggag taccttgaga      9660
aatggcggga ggctgaagaa aaggccggga aggaactgga cgccatcatc gcgccgatta      9720
cgcctaccgc tgcggtacgg catgaccagt tccggtacta tgggtatgcc tctgtgatca      9780
acctgctgga tttcacgagc gtggttgttc cggttacctt tgcggataag aacatcgata      9840
agaagaatga gagtttcaag gcggttagtg agcttgatgc cctcgtgcag gaagagtatg      9900
atccggaggc gtaccatggg gcaccggttg cagtgcaggt tatcggacgg agactcagtg      9960
aagagaggac gttggcgatt gcagaggaag tggggaagt gctgggaaat gtggtgactc      10020
cataggtcga gaatttatac ttagataagt atgtacttac aggtatattt ctatgagata      10080
ctgatgtata catgcatgat aatatttaaa cggttattag tgccgattgt cttgtgcgat      10140
aatgacgttc ctatcaaagc aatacactta ccacctatta catgggccaa gaaaatattt      10200
tcgaacttgt ttagaatatt agcacagagt atatgatgat atccgttaga ttatgcatga      10260
ttcattccta caactttttc gtagcataag gattaattac ttggatgcca ataaaaaaaa      10320
aaaacatcga gaaaatttca gcatgctcag aaacaattgc agtgtatcaa agtaaaaaaa      10380
agattttcgc tacatgttcc ttttgaagaa agaaaatcat ggaacattag atttacaaaa      10440
atttaaccac cgctgattaa cgattagacc gttaagcgca caacaggtta ttagtacaga      10500
gaaagcattc tgtggtgttg ccccggactt tctttttgcga cataggtaaa tcgaatacca      10560
tcatactatc ttttccaatg actccctaaa gaaagactct tcttcgatgt tgtatacgtt      10620
ggagcatagg gcaagaattg tggcttgaga tgaattcact ggccgtcgtt ttacaacgtc      10680
gtgactggga aaaccctggc gttacccaac ttaatcgcct tgcagcacat cccccttttcg      10740
ccagctggcg taatagcgaa gaggcccgca ccgatcgccc ttcccaacag ttgcgcagcc      10800
tgaatggcga atggcgcctg atgcggtatt ttctccttac gcatctgtgc ggtatttcac      10860
accgcatatg gtgcactctc agtacaatct gctctgatgc cgcatagtta agccagcccc      10920
gacacccgcc aacacccgct gacgcgccct gacgggcttg tctgctcccg gcatccgctt      10980
acagacaagc tgtgaccgtc tccgggagct gcatgtgtca gaggttttca ccgtcatcac      11040
cgaaacgcgc gagacgaaag ggcctcgtga tacgcctatt tttataggtt aatgtcatga      11100
taataatggt ttcttagacg tcaggtggca ctttttcgggg aaatgtgcgc ggaacccta      11160
tttgtttatt tttctaaata cattcaaata tgtatccgct catgagacaa taaccctgat      11220
aaatgcttca ataatattga aaaaggaaga gtatgagtat tcaacatttc cgtgtcgccc      11280
ttattcctt ttttgcggca ttttgccttc ctgtttttgc tcacccagaa acgctggtga      11340
aagtaaaaga tgctgaagat cagttgggtg cacgagtggg ttacatcgaa ctggatctca      11400
acagcggtaa gatccttgag agttttcgcc ccgaagaacg ttttccaatg atgagcactt      11460
ttaaagttct gctatgtggc gcggtattat cccgtattga cgccgggcaa gagcaactcg      11520
gtcgccgcat acactattct cagaatgact tggttgagta ctcaccagtc acagaaaagc      11580
atcttacgga tggcatgaca gtaagagaat tatgcagtgc tgccataacc atgagtgata      11640
acactgcggc caacttactt ctgacaacga tcggaggacc gaaggagcta accgcttttt      11700
tgcacaacat gggggatcat gtaactcgcc ttgatcgttg ggaaccggag ctgaatgaag      11760
ccataccaaa cgacgagcgt gacaccacga tgcctgtagc aatggcaaca acgttgcgca      11820
aactattaac tggcgaacta cttactctag cttcccggca acaattaata gactggatgg      11880
aggcggataa agttgcagga ccacttctgc gctcggccct tccggctggc tggtttattg      11940
ctgataaatc tggagccggt gagcgtgggt ctcgcggtat cattgcagca ctggggccag      12000
atggtaagcc ctcccgtatc gtagttatct acacgacggg gagtcaggca actatggatg      12060
aacgaaatag acagatcgct gagataggtg cctcactgat taagcattgg taactgtcag      12120
accaagttta ctcatatata ctttagattg atttaaaact tcattttaa tttaaaagga      12180
tctaggtgaa gatccttttt gataatctca tgaccaaaat cccttaacgt gagttttcgt      12240
tccactgagc gtcagacccc gtagaaaaga tcaaaggatc ttcttgagat cctttttttc      12300
tgcgcgtaat ctgctgcttg caaacaaaaa aaccaccgct accagcggtg gtttgtttgc      12360
cggatcaaga gctaccaact ctttttccga aggtaactgg cttcagcaga gcgcagatac      12420
caaatactgt ccttctagtg tagccgtagt taggccacca cttcaagaac tctgtagcac      12480
cgcctacata cctcgctctg ctaatcctgt taccagtggc tgctgccagt ggcgataagt      12540
cgtgtcttac cgggttggac tcaagacgat agttaccgga taaggcgcag cggtcgggct      12600
gaacgggggg ttcgtgcaca cagcccagct tggagcgaac gacctacacc gaactgagat      12660
acctacagcg tgagctatga gaaagcgcca cgcttcccga agggagaaag gcggacaggt      12720
atccggtaag cggcagggtc ggaacaggag agcgcacgag ggagcttcca gggggaaacg      12780
cctggtatct ttatagtcct gtcgggtttc gccacctctg acttgagcgt cgatttttgt      12840
gatgctcgtc aggggggcgg agcctatgga aaaacgccag caacgcggcc ttttacggt      12900
tcctggcctt ttgctggcct tttgctcaca tgttctttcc tgcgttatcc cctgattctg      12960
tggataaccg tattaccgcc tttgagtgag ctgataccgc tcgccgcagc cgaacgaccg      13020
agcgcagcga gtcagtgagc gaggaagcgg aagagcgccc aatacgcaaa ccgcctctcc      13080
ccgcgcgttg gccgattcat taatgcagct ggcacgacag gtttcccgac tggaaagcgg      13140
gcagtgagcg caacgcaatt aatgtgagtt agctcactca ttaggcaccc caggctttac      13200
actttatgct tccggctcgt atgttgtgtg gaattgtgag cggataacaa tttcacacag      13260
gaaacagcta tgaccatgat tacgcc                                          13286

SEQ ID NO: 42          moltype = DNA   length = 16359
FEATURE                Location/Qualifiers
misc_feature           1..16359
                       note = pBOL36
source                 1..16359
                       mol_type = other DNA
                       organism = synthetic construct
SEQUENCE: 42
aagcttgcat gcctgcaggt cgacggcgcg ccggcgcccgt ttaaacaatg gcaaactgag      60
cacaacaata ccagtccgga tcaactggca ccatctctcc cgtagtctca tctaattttt      120
```

```
cttccggatg aggttccaga tataccgcaa cacctttatt atggtttccc tgagggaata    180
atagaatgtc ccattcgaaa tcaccaattc taaacctggg cgaattgtat ttcgggtttg    240
ttaactcgtt ccagtcagga atgttccacg tgaagctatc ttccagcaaa gtctccactt    300
cttcatcaaa ttgtgggaga atactcccaa tgctcttatc tatgggactt ccgggaaaca    360
cagtaccgat acttcccaat tcgtcttcag agctcattgt ttgtttgaag agactaatca    420
aagaatcgtt ttctcaaaaa aattaatatc ttaactgata gtttgatcaa aggggcaaaa    480
cgtaggggca aacaaacgga aaaatcgttt ctcaaatttt ctgatgccaa gaactctaac    540
cagtcttatc taaaaattgc cttatgatcc gtctctccgg ttacagcctg tgtaactgat    600
taatcctgcc tttctaatca ccattctaat gttttaatta agggattttg tcttcattaa    660
cggctttcgc tcataaaaat gttatgacgt tttgcccgca ggcgggaaac catccacttc    720
acgagactga tctcctctgc cggaacaccg ggcatctcca acttataagt tggagaaata    780
agagaatttc agattgagag aatgaaaaaa aaaaaaaaa aaaaggcaga ggagagcata    840
gaaatggggt tcactttttg gtaaagctat agcatgccta tcacatataa atagagtgcc    900
agtagcgact tttttcacac tcgaaatact cttactactg ctctcttgtt gtttttatca    960
cttcttgttt cttcttggta aatagaatat caagctacaa aaagcataca atcaactatc   1020
aactattaac tatatcgtaa tacacaggcc ggccaaaatg aaggccaaat caaggcggga   1080
agggacaacc aggacgtaaa gggtagcctc cccataacat aaactcaata aaatatatag   1140
tcttcaactt gaaaaaggaa caagctcatg caaagaggtg gtacccgcac gccgaaatgc   1200
atgcaagtaa cctattcaaa gtaatatctc atacatgttt catgagggta acaacatgcg   1260
actgggtgag catatgttcc gctgatgtga tgtgcaagat aaacaagcaa gacagaaact   1320
aacttcttct tcatgtaata aacacacccc gcgtttattt acctatcttt aaacttcaac   1380
accttatatc ataactaata tttcttgaga taagcacact gcacccatac cttccttaaa   1440
aacgtagctt ccagtttttg gtggttctgg cttccttccc gattccgccc gctaaacgca   1500
taattttgtt gcctggtggc atttgcaaaa tgcataacct atgcatttaa aagattatgt   1560
atgctcttct gacttttcgt gtgatgaggc tcgtggaaaa aatgaataat ttatgaattt   1620
gagaacaatt ttgtgttgtt acggtatttt actatgaaat aatcaatcaa ttgaggattt   1680
tatgcaaata tcgtttgaat attttttcga ccctttgagt actttttcttc ataattgcat   1740
aatattgtcc gctgcccgtt tttctgttag acggtgtctt gatctacttg ctatcgttca   1800
acaccacctt attttctaac tatttttttt ttagctcatt tgaatcagct tatggtgatg   1860
gcacatttt gcataaacct agctgtcctc gttgaacata ggaaaaaaaa atatataaac   1920
aaggctcttt cactctcctt ggaatcagat ttgggtttgt tccctttatt ttcatatttc   1980
ttgtcatatt cttttctcaa ttattatctt ctactcataa cctcacgcaa aataacacag   2040
tcaaatcaat caaaatggac ttcaacttga ccagagaaca agaattggtc agacaaatgg   2100
ttagagaatt tgctgaaaac gaagttaagc caattgctgc tgaaatcgat gaaactgaaa   2160
gattcccaat ggaaaacgtc aagaagatgg gtcaatacgg tatgatggat attccattct   2220
ctaaggaata cggtggtgct ggtggtgacg tcttgtctta catcattgct gtcgaagaat   2280
tgtccaaggt ttgtggtacc actggtgtca tcttatctgc tcacacttct ctatgtgcct   2340
ccttgatcaa cgaacacggt actgaagaac aaaagcaaaa gtacttggtt ccattggcca   2400
agggtgaaa gattggtgcc tacggtttga ctgaaccaaa cgctggtact gactctggtg   2460
ctcaacaaac tgttgccgtt ttggaaggtg accactacg catcaacggt tccaagatct   2520
tcatcaccaa cggtggtgtt gctgacacct ttgtcatctt cgctatgacc gatcgtacca   2580
agggtaccaa gggtatctct gctttcatta ttgaaaaggg tttcaagggt ttctccatcg   2640
gtaaggtcga acaaaagttg ggtatcagag cttcctctac cactgaattg gttttcgaag   2700
acatgattgt tccagttgaa aacatgatcg gtaaggaagg taagggtttc ccaattgcca   2760
tgaagacttt agatggtggt agaattggta ttgctgctca agctttgggt attgctgaag   2820
gtgccttcaa cgaagctaga gcttacatga aggaaagaa gcaattcggt agatctttgg   2880
acaaattcca aggtttggct tggatgatgg ctgacatgga cgttgccatc gaatctgctc   2940
gttacttggt ctacaaggct gcttacttga agcaagctgg tttgccatac accgtcgatg   3000
ctgccagagc taagttgcac gctgccaacg ttgccatgga tgtcaccacc aaggctgtcc   3060
aattattcgg tggttacggt tacaccaagg actacccagt tgaaagaatg atgagagatg   3120
ctaagatcac tgaaatctac gaaggtactt ctgaagttca aaagttggtt atctccggtca   3180
agatcttcag ataggcccgg gcataaagca atcttgatga ggataatgat ttttttttga   3240
atatacataa atactaccgt ttttctgcta gattttgtga agacgtaaat aagtacatat   3300
tacttttaa gccaagacaa gattaagcat taactttacc cttttctctt ctaagtttca   3360
atactagtta tcactgttta aaagttatgg cgagaacgtc ggcggttaaa atatattacc   3420
ctgaacgtgg tgaattgaag ttctaggatg gtttaaagat ttttccttttt tgggaaataa   3480
gtaaacaata tattgctgcc tttgcaaac gcacataccc acaatatgtg actattggca   3540
aagaacgcat tatcctttga agaggtggat actgatacta agagagtctc tattccggct   3600
ccactttag tccagagatt acttgtcttc ttacgtatca gaacaagaaa gcatttccaa   3660
agtaattgca tttgcccttg agcagtatat atatactaag aagtttaaac atttaaacgt   3720
ccggcctaga aagcatacta tactattcga cacttccttt caatcctgga attaacagtc   3780
acttttaaaa aagacatcta ccgtgaaggt gccgtagagt atcgcgttac catatcgcca   3840
aaaactgata tacgccgcgg aaaccaggca aacaattgaa aagaaaaatt ttgaggaact   3900
ctctgcatcg aagccgtcta gagttaccac tagtcagatg ccgcgggcac ttgagcacct   3960
catgcacagc aataacacaa cacaatggtt agtagcaacc tgaattcggt cattgatgca   4020
tgcatgtgcc gtgaagcggg acaaccagaa aagtcgtcta taaatgccgg cacgtgcgat   4080
catcgtggcg gggttttaag agtgcatatc acaaattgtc gcattaccgc ggaaccgcca   4140
gatattcatt acttgacgca aaagcgtttg aaataatgac gaaaaagaag gaagaaaaaa   4200
aaagaaaaat accgcttcta ggcgggttat ctactgatcc gagcttccac taggatagca   4260
cccaaacacc tgcatatttg gacgaccttt acttacacca ccaaaaacca ctttcgcctc   4320
tcccgccct gataacgtcc actaattgag cgattacctg agcggtcctc ttttgtttgc   4380
agcatgagac ttgcatactg caaatcgtaa gtagcaacgc tcaaggtca aaactgtatg   4440
gaaaccttgt cacctcactt aattctagct agcctaccct gcaagtcaag aggtctccgt   4500
gattcctgac cacctcaagg tatgcctctc cccggaacat gtggcctttt ctggcacaca   4560
tgatctccac gatttcaaca tataaatagc ttttgataat ggcaatatta atcaaattta   4620
ttttacttct ttcttgtaac atctctcttg taatcccttta ttcttctag ctatttttca   4680
taaaaaccaa agcaactgct tatcaacaca caaacactaa atcaaaatgg tcgatttcga   4740
atactctatc ccaaccagaa tcttcttcgg taaggacaag atcaacgttt tgggtagaga   4800
attgaagaaa tacggttcca aggttttgat tgtctacggt ggtggttcca tcaagagaaa   4860
```

```
cggtatctac gacaaggctg tctccatttt ggaaaagaac tctatcaaat tctacgaatt   4920
ggctggtgtt gaaccaaacc caagagttac caccgtcgaa aagggtgtca agatctgtcg   4980
tgaaaacggt gttgaagttg tttttggccat cggtggtggt tctgccattg actgtgccaa   5040
ggtcattgct gctgcctgtg aatacgatgg taacccatgg gacattgtct tggatggttc   5100
taagatcaag cgtgtcttac caattgcttc catcttgact atcgctgcta ctggttctga   5160
aatggcacac tgggctgtta tcaacaacat ggacactaac gaaaagttga ttgctgctca   5220
cccagatatg gccccaaagt tctctatttt ggacccaacc tacacttaca ctgttccaac   5280
caaccaaact gctgctggta ctgctgatat catgtctcac atctttgaag tttacttctc   5340
caacaccaag accgcttact tgcaagacag aatggctgaa gctctattaa gaacctgtat   5400
caagtacggt ggtattgctt tggaaaagcc agatgactac gaagccagag ctaacttgat   5460
gtgggcttcc tctttggcta tcaacggttt attgacttac ggtaaggaca ccaactggtc   5520
cgttcatttg atggaacacg aattgtctgc ttactacgat atcactcacg gtgtcggttt   5580
ggccatcttg actccaaact ggatggaata cattttgaac aacgacactg tctacaagtt   5640
cgtcgaatac ggtgttaacg tctggggtat tgacaaggaa aagaaccact acgacattgc   5700
tcaccaagcc atccaaaaga ccagagacta tttcgtcaac gtttttgggtt taccatccag   5760
attaagagat gttggtattg aagaagaaaa attggatatc atggctaagg aatctgtcaa   5820
attgactggt ggtaccattg gtaacttgag acctgttaac gcttctgaag ttttgcaaat   5880
cttcaagaaa tctgtttagg cccgggctcc tgttgaagta gcatttaatc ataattttg    5940
tcacatttta atcaacttga ttttttctggt ttaattttc taattttaat tttaattttt   6000
ttatcaatgg gaactgatac actaaaaaga attaggagcc aacaagaata agccgcttat   6060
ttcctactag agtttgctta aaatttcatc tcgaattgtc attctaatat tttatccaca   6120
cacacacctt aaaattttta gattaaatgg catcaactct tagcttcaca cacacacaca   6180
caccgaagct ggttgtttta tttgatttga tataattggt ttctctggat ggtactttt    6240
ctttcttggt tatttcctat tttaaaatat gaaacgcaca caagtcataa ttattctaat   6300
agagcacaat tcacaacacg cacatttcaa ctttaatatt ttttttagaaa cactttattt   6360
agtctaattc ttaattttta atatatataa tgcacacaca cgtttaaatg ggcccggggc   6420
ccgtttaaac ggccggccct tccctttac agtgcttcgg aaaagcacag cgttgtccaa   6480
gggaacaatt tttcttcaag ttaatgcata agaaatatct ttttttatgt ttagctaagt   6540
aaaagcagct tggagtaaaa aaaaaaatga gtaaatttct cgatggatta gtttctcaca   6600
ggtaacatag caaaaaccaa gaaaagcccg cttctgaaaa ctacagttga cttgtatgct   6660
aaagggccag actaatggga ggagaaaaag aaacgaatgt atatgctcat ttacactcta   6720
tatcaccata tggaggataa gttgggctga gcttctgatc caatttattc tatccattag   6780
ttgctgatat gtcccaccag ccaacacttg atagtatcta ctcgccattc acttccagca   6840
gcgccagtag ggttgttgag cttagtaaaa atgtgcgcac cacaagccta catgactcca   6900
cgtcacatga aaccacaccg tggggccttg ttgcgctagg aataggatat gcgacgaaga   6960
cgcttctgct tagtaaccac accacatttt caggggtcg atctgcttgc ttcctttact   7020
gtcacgagcg gcccataatc gcgcttttt tttaaaaggc gcgagacagc aaacaggaag   7080
ctcgggtttc aaccttcgga gtggtcgcag atctggagac tggatctta caatacagta   7140
aggcaagcca ccatctgctt cttaggtgca tgcgacggta tccacgtgca gaacaacata   7200
gtctgaagaa gggggggagg agcatgttca ttctctgtag cagtaagagc ttggtgataa   7260
tgaccaaaac tggagtctcg aaatcatata aatagacaat atattttcac acaatgagat   7320
ttgtagtaca gttctattct ctctcttgca taaataagaa attcatcaag aacttggttt   7380
gatatttcac caacacacac aaaaaaacagt acttcactaa atttacacac aaaacaaaat   7440
gaaggttacc aaccaaaagg aattgaagca aaagttgaac gaattgagag aagctcaaaa   7500
gaagttcgct acctacactc aagaacaagt tgacaagatc ttcaagcaat gtgccattgc   7560
tgctgccaag gaacgtatca acttggccaa gttggctgtc gaagaaaccg gtattggttt   7620
ggttgaagac aagatcatca agaaccactt cgctgctgaa tacatctaca acaagtacaa   7680
gaacgaaaag acctgtggta tcatcgacca cgatgactct ttgggtatca ccaaggttgc   7740
tgaaccaatc ggtattgtcg ccgccattgt cccaaccact aacccaactt ccactgccat   7800
cttcaaatct ttgatctcct tgaagaccag aaacgctatc ttcttctccc cacacccaag   7860
agccaagaag tccaccattg ctgctgccaa attaatcttg gatgctgctg ttaaggctgg   7920
tgccccaaag aacattattg gttggatcga tgaaccttcc attgaattgt ctcaagactt   7980
gatgtctgaa gctgatatca tcttggctac cggtggtcca tccatggtca aggccgctta   8040
ctcttctggt aagccagcta ttggtgttgg tgctggtaac actccagcta tcatcgatga   8100
atctgctgac attgacatgg ctgtctcctc cattatcttg tccaagactt atgacaacgg   8160
tgtcatctgt gcctctgaac aatccatctt ggttatgaac tctatctacg aaaaggtcaa   8220
ggaagaattt gttaagagag gttcctacat cttaaaccaa aatgaaattg ccaagatcaa   8280
ggaaaccatg ttcaagaacg gtgccatcaa cgctgacatt gtcggtaaat ctgcttacat   8340
cattgccaag atggctggta ttgaagttcc acaaaccact aagattttga tcggtgaagt   8400
tcaatctgtc gaaaagtctg aattattctc tcacgaaaag ttgtctccag tcttggctat   8460
gtacaaggtc aaggatttcg acgaagcttt gaagaaggct caaagattaa ttgaattagg   8520
tggttctggt cacacctctt ctctatacat tgactctcaa aacaacaagg acaaggtcaa   8580
ggaattcggt ctagctatga agacttccag aactttcatc aacatgccat cttctcaagg   8640
tgcttctggt gatttgtaca actttggccat tgctccatct ttcactttag gttgtggtac   8700
ctggggtggt aactctgttt ctcaaaacgt tgaaccaaag catttgctaa acatcaagtc   8760
cgttgctgaa agaagagaaa acatgttgtg gttcaaggtt ccacaaaaga tctacttcaa   8820
atacggttgt ttgagatttg cttttgaagga attgaaagat atgaacaaga agcgtgcttt   8880
catcgttact gacaaggatt tgttcaaatt gggttacgtt aacaagatca ctaaggtttt   8940
ggatgaaatt gatatcaagt actccatctt cactgatatc aaatctgacc caaccattga   9000
ctccgtcaag aagggtgcta aggaaatgtt gaacttcgaa ccagatacca ttatctccat   9060
tggtggtggt tctccaatgg atgctgccaa ggttatgcat ttgttgtacg aatacccaga   9120
agctgaaatc gaaacttggg ccatcaactt catggacatc agaaagagaa tctgtaactt   9180
cccaaagttg ggtaccaagg ccatttctgt tgccattcca accaccgctg gtaccggttc   9240
tgaagctact ccatttgctg tcatcaccaa cgacgaaagc ggtatgaagt acccattgac   9300
ctcttacgaa ttgactccaa acatggccat cattgacact gaattgatgt tgaacatgcc   9360
aagaaagttg actgctgcta ccggtattga cgctttagtc cacgctatcg aagcttacgt   9420
ctccgttatg gccactgact acactgacga attggctttg agagctatca agatgatctt   9480
caagtacttg ccaagagctt acaagaacgg tactaacgat atcgaagctc gtgaaaagat   9540
ggctcacgct tccaacattg ctggtatggc tttcgctaac gctttcttgg gtgtttgtca   9600
```

```
ctccatggcc cacaagttgg gtgctatgca ccacgttcct cacggtattg cttgtgctgt   9660
tttgattgaa gaagtcatca agtacaacgc tactgactgt ccaaccaagc aaactgcttt   9720
cccacaatac aagtctccaa acgccaagag aaagtacgct gaaattgctg aatacttgaa   9780
cttgaaaggt acttctgaca ctgaaaaggt cactgcttta atcgaagcta tctccaagtt   9840
gaagattgac ttatctattc ctcaaaacat ctctgctgct ggtattaaca agaaggactt   9900
ctacaacact ttagacaaga tgtccgaatt ggctttcgat gaccaatgta ccaccgctaa   9960
cccaagatac ccattgatct ctgaattgaa ggatatctac atcaagtcct tttaagcccg   10020
ggcgcggatc tcttatgtct ttacgattta tagttttcat tatcaagtat gcctatatta   10080
gtatatagca tctttagatg acagtgttcg aagtttcacg aataaaagat aatattctac   10140
tttttgctcc caccgcgttt gctagcacga gtgaacacca tccctcgcct gtgagttgta   10200
cccattcctc taaactgtag acatggtagc ttcagcagtg ttcgttatgt acggcatcct   10260
ccaacaaaca gtcggttata gtttgtcctg ctcctctgaa tcgtctccct cgatatttct   10320
cattttcctt cgcatgccag cattgaaatg atcgaagttc aatgatgaaa cggtaattct   10380
tctgtcattt actcatctca tctcatcaag ttatataatt ctatacggat gtaatttttc   10440
acttttcgtc ttgacgtcca ccctataatt tcaattattg aaccctcaca aatgatgcac   10500
tgcaatgtac acaccctcat atagtttaaa catttaaatg ggccgctcta gaggatcccc   10560
gggtaccgag ctcgggccca gcgctactag ttccggtaat ttgaaaacaa acccggtctc   10620
gaagcggaga tccggcgata attaccgcag aaataaaccc atacacgaga cgtagaacca   10680
gccgcacatg gccggagaaa ctcctgcgag aatttcgtaa actcgcgcgc attgcatctg   10740
tatttcctaa tgcggcactt ccaggcctcg agacctctga catgcttttg acaggaatag   10800
acattttcag aatgttatcc atatgccttt cgggtttttt tccttccttt tccatcatga   10860
aaaatctctc gagaccgttt atccattgct tttttgttcg ctttttccct cgttcacaga   10920
aagtctgaag aagctatagt agaactatga gctttttttg tttctgtttt cctttttttt   10980
tttttacct ctgtggaaat tgttactctc acactcttta gttcgtttgt ttgtttttgtt   11040
tattccaatt atgaccggtg acgaaacgtg gtcgatggtg ggtaccgctt atgctcccct   11100
ccattagttt cgattatata aaaaggccaa atattgtatt atttcaaat gtcctatcat   11160
tatcgtctaa catctaattt ctcttaaatt ttttctcttt ctttcctata acaccaaatag  11220
tgaaaatctt tttttcttct atatctacaa aaacttttt tttctatcaa cctcgttgat   11280
aaattttttc tttaacaatc gttaataatt aattaattgg aaaataacca ttttttctct   11340
cttttataca cacattcaaa agaaagaaaa aaaatatacc ccagctagtt aaagaaaatc   11400
attgaaaaga ataagaagat aagaaagatt taattatcaa acaatatcaa tatgcctcaa   11460
tcctgggaag aactggccgc tgataagcgc gcccgcctcg caaaaaccat ccctgatgaa   11520
tggaaagtcc agacgctgcc tgcggaagac agcgttattg atttcccaaa gaaatcgggg   11580
atcctttcag aggccgaact gaagatcaca gaggcctccg ctgcagatct tgtgtccaag   11640
ctggcggccg gagagttgac ctcggtggaa gttacgctag cattctgtaa acgggcagca   11700
atcgcccagc agttaacaaa ctgcgcccac gagttcttcc ctgacgccgc tctcgcgcag   11760
gcaagggaac tcgatgaata ctacgcaaag cacaagagac ccgttggtcc actccatggc   11820
ctccccatct ctctcaaaga ccagcttcga gtcaagggct acgaaacatc aatgggctac   11880
atctcatggc taaacaagta cgacgaaggg gactcggttc tgacaaccat gctccgcaaa   11940
gccggtgccg tcttctacgt caagacctct gtcccgcaga ccctgatggt ctgcgagaca   12000
gtcaacaaca tcatcgggcg caccgtcaac ccacgcaaca agaactggtc gtgcggcggc   12060
agttctggtg gtgagggtgc gatcgttggg attcgtggtg gcgtcatcgg tgtaggaacg   12120
gatatcgttg gctcgattcg agtgccggcc gcgttcaacat tcctgtacgg tctaaggccg  12180
agtcatgggc ggctgccgta tgcaaagatg gcgaacagca tggagggtca ggagacggtg   12240
cacagcgttg tcgggccgat tacgcactct gttgaggacc tccgcctctt caccaaatcc   12300
gtcctcggtc aggagccatg gaaatacgac tccaaggtca tccccatgcc ctggcgccag   12360
tccgagtcgg acattattgc ctccaagatc aagaacgggc ggtcaatat cggctactac   12420
aacttcgacg gcaatgtcct tccacaccct cctatcctgc gcggcgtgga aaccaccgtc   12480
gccgcactcg ccaaagccgg tcacaccgtg accccgtgga cgccatacaa gcacgatttc   12540
ggccacgatc tcatctccca tatctacgcg gctgacggca gcgccgacgt aatgcgcgat   12600
atcagtgcat ccggcgagcc ggcgattcca aatatcaaag acctactgaa cccgaacatc   12660
aaagctgtta acatgaacga gctctgggac acgcatctcc agaagtggaa ttaccagatg   12720
gagtaccttg agaaatggcg ggaggctgaa gaaaaggccg ggaaggaact ggacgccatc   12780
atcgcgccga ttacgcctac cgctgcggta cggcatgacc agttccggta ctatgggtat   12840
gcctctgtga tcaacctgct ggatttcacg agcgtggttg ttccggttac ctttgcggat   12900
aagaacatcg ataagaagaa tgagagtttc aaggcggta gtgagcttga tgccctcgtg   12960
caggaagagt atgatccgga ggcgtaccat ggggcaccgg ttgcagtgca ggttatcgga   13020
cggagactca gtgaagagag gacgttggcg attgcagagg aagtggggaa gttgctggga   13080
aatgtggtga ctccataggt cgagaattta tacttagata agtatgtact tacaggtata   13140
tttctatgag atactgatgt atacatgcat gataatattt aaacggttat tagtgccgat   13200
tgtcttgtgc gataatgacg ttcctatcaa agcaatacac ttaccaccta ttacatgggc   13260
caagaaaata ttttcgaact tgtttagaat attagcacag agtatatgat gatatccgtt   13320
agattatgca tgattcattc ctacaacttt ttcgtagcat aaggattaat tacttggatg   13380
ccaataaaaa aaaaaaacat cgagaaaatt tcagcatgct gcagtatgat tgcagtgcat   13440
caaagtaaaa aaaagatttt cgctacatgt tccttttgaa gaaagaaaat catggaacat   13500
tagatttaca aaaatttaac caccgctgat taacgattag accgttaagc gcacaacagg   13560
ttattagtac agagaaagca ttctgtggtg ttgccccgga ctttcttttg cgacataggt   13620
aaatcgaata ccatcatact atcttttcca atgactccct aaagaaagac tcttcttcga   13680
tgttgtatac gttggagcat agggcaagaa ttgtggcttg agatgaattc actggccgtc   13740
gttttacaac gtcgtgactg ggaaaaccct ggcgttaccc aacttaatcg ccttgcagca   13800
catcccctt tcgccagctg gcgtaatagc gaagaggccc gcaccgatcg cccttcccaa   13860
cagttgcgca gcctgaatgg cgaatggcgc ctgatgcggt attttctcct tacgcatctg   13920
tgcggtattt cacaccgcat atggtgcact ctcagtacaa tctgctctga tgccgcatag   13980
ttaagccagc cccgacaccc gccaacaccc gctgacgcgc cctgacgggc ttgtctgctc   14040
ccggcatccg cttacagaca agctgtgacc gtctccggga gctgcatgtg tcagaggttt   14100
tcaccgtcat caccgaaacg cgcgagacga aagggcctcg tgatacgcct atttttatag   14160
gttaatgtca tgataataat ggtttcttag acgtcaggtg gcacttttcg gggaaatgtg   14220
cgcggaaccc ctatttgttt attttttctaa atacattcaa atatgtatcc gctcatgaga   14280
caataaccct gataaatgct tcaataatat tgaaaaagga agagtatgag tattcaacat   14340
```

-continued

```
ttccgtgtcg cccttattcc cttttttgcg gcattttgcc ttcctgtttt tgctcaccca   14400
gaaacgctgg tgaaagtaaa agatgctgaa gatcagttgg gtgcacgagt gggttacatc   14460
gaactggatc tcaacagcgg taagatcctt gagagttttc gccccgaaga acgttttcca   14520
atgatgagca cttttaaagt tctgctatgt ggcgcggtat tatcccgtat tgacgccggg   14580
caagagcaac tcggtcgccg catacactat tctcagaatg acttggttga gtactcacca   14640
gtcacagaaa agcatcttac ggatggcatg acagtaagag aattatgcag tgctgccata   14700
accatgagtg ataacactgc ggccaactta cttctgacaa cgatcggagg accgaaggag   14760
ctaaccgctt ttttgcacaa catgggggat catgtaactc gccttgatcg ttgggaaccg   14820
gagctgaatg aagccatacc aaacgacgag cgtgacacca cgatgcctgt agcaatggca   14880
acaacgttgc gcaaactatt aactggcgaa ctacttactc tagcttcccg gcaacaatta   14940
atagactgga tggaggcgga taaagttgca ggaccacttc tgcgctcggc ccttccggct   15000
ggctggttta ttgctgataa atctggagcc ggtgagcgtg ggtctcgcgg tatcattgca   15060
gcactggggc cagatggtaa gccctcccgt atcgtagtta tctacacgac ggggagtcag   15120
gcaactatgg atgaacgaaa tagacagatc gctgagatag gtgcctcact gattaagcat   15180
tggtaactgt cagaccaagt ttactcatat atactttaga ttgatttaaa acttcatttt   15240
taatttaaaa ggatctaggt gaagatcctt tttgataatc tcatgaccaa aatcccttaa   15300
cgtgagtttt cgttccactg agcgtcagac cccgtagaaa agatcaaagg atcttcttga   15360
gatccttttt ttctgcgcgt aatctgctgc ttgcaaacaa aaaaaccacc gctaccagcg   15420
gtggtttgtt tgccggatca agagctacca actctttttc cgaaggtaac tggcttcagc   15480
agagcgcaga taccaaatac tgtccttcta gtgtagccgt agttaggcca ccacttcaag   15540
aactctgtag caccgcctac atacctcgct ctgctaatcc tgttaccagt ggctgctgcc   15600
agtggcgata agtcgtgtct taccgggttg gactcaagac gatagttacc ggataaggcg   15660
cagcggtcgg gctgaacggg gggttcgtgc acacagccca gcttggagcg aacgacctac   15720
accgaactga gatacctaca gcgtgagcta tgagaaagcg ccacgcttcc cgaagggaga   15780
aaggcggaca ggtatccggt aagcggcagg gtcggaacag gagagcgcac gagggagctt   15840
ccaggggga acgcctggta tctttatagt cctgtcgggt ttcgccacct ctgacttgag   15900
cgtcgatttt tgtgatgctc gtcaggggg cggagcctat ggaaaaacgc cagcaacgcg   15960
gcctttttac ggttcctggc cttttgctgg ccttttgctc acatgttctt tcctgcgtta   16020
tcccctgatt ctgtggataa ccgtattacc gcctttgagt gagctgatac cgctcgccgc   16080
agccgaacga ccgagcgcag cgagtcagtg agcgaggaag cggaagagcg cccaatacgc   16140
aaaccgcctc tccccgcgcg ttggccgatt cattaatgca gctggcacga caggtttccc   16200
gactggaaag cgggcagtga gcgcaacgca attaatgtga gttagctcac tcattaggca   16260
ccccaggctt tacactttat gcttccggct cgtatgttgt gtggaattgt gagcggataa   16320
caatttcaca caggaaacag ctatgaccat gattacgcc                          16359
```

```
SEQ ID NO: 43        moltype = DNA   length = 8684
FEATURE              Location/Qualifiers
misc_feature        1..8684
                    note = pBOL113
source              1..8684
                    mol_type = other DNA
                    organism = synthetic construct
SEQUENCE: 43
tcgcgcgttt cggtgatgac ggtgaaaacc tctgacacat gcagctcccg gagacggtca   60
cagcttgtct gtaagcggat gccgggagca gacaagcccg tcaggcgcg tcagcgggtg   120
ttggcgggtg tcgggctgg cttaactatg cggcatcaga gcagattgta ctgagagtgc   180
accataccac agcttttcaa ttcaattcat catttttttt ttattctttt ttttgatttc   240
ggtttctttg aaattttttt gattcggtaa tctccgaaca gaaggaagaa cgaaggaagg   300
agcacagact tagattggta tatatacgca tatgtagtgt tgaagaaaca tgaaattgcc   360
cagtattctt aacccaactg cacagaacaa aaacctgcag gaaacgaaga taaatcatgt   420
cgaaagctac atataaggaa cgtgctgcta ctcatcctag tcctgttgct gccaagctat   480
ttaatatcat gcacgaaaag caaacaaact tgtgtgcttc attggatgtt cgtaccacca   540
aggaattact ggagttagtt gaagcattag gtcccaaaat ttgtttacta aaaacacatg   600
tggatatctt gactgatttt tccatggagg gcacagttaa gccgctaaag gcattatccg   660
ccaagtacaa tttttttactc ttcgaagaca gaaaatttgc tgacattggt aatacagtca   720
aattgcagta ctctgcgggt gtatacgaaa tagcagaatg ggcagacatt acgaatgcac   780
acggtgtggt gggcccaggt attgttagcg gtttgaagca ggcggcagaa gaagtaacaa   840
aggaacctag aggccttttg atgttagcag aattgtcatg caagggctcc ctatctactg   900
gagaatatac taagggtact gttgacattg cgaagagcga caaagatttt gttatcggct   960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga ataccgcac    1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg cgctggcaa    1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcgg    1860
cctcttcgct attacgccag ctggcgaaag gggatgtgc tgcaaggcga ttaagttggg    1920
taacgccagg gttttcccag tcacgacgtt gtaaaacgac ggccagtgag cgcgcgtaat   1980
acgactcact atagggcgaa ttgggtaccg gccccccct cgaggtcgac ggtatcgata   2040
agcttgatat cgaattcctg cagcccgggg gatccactag ttctagagcg gcccatttaa   2100
acggccggcc ctagatcaga gggtggtaaa tgaagtgtaa tagtattcat ttttcttata   2160
```

-continued

```
aatcatccct tccgtgattt atacaaaaga agaggagaat atgctgaata cttggtatat  2220
tactctacat tatactctta tcttgacggg tattctgagc atcttactca gtttcaagat  2280
cttttaatgt ccaaaaacat ttgagccgat ctaaatactt ctgtgttttc attaatttat  2340
aaattgtact cttttaagac atggaaagta ccaacatcgg ttgaaacagt ttttcattta  2400
cttatggttt attggttttt ccagtgaatg attatttgtc gttacccttt cgtaaaagtt  2460
caaacacgtt tttaagtatt gtttagttgc tctttcgaca tatatgatta tccctgcgcg  2520
gctaaagtta aggatgcaaa aaacataaga caactgaagt taatttacgt caattaagtt  2580
ttccagggta atgatgtttt gggcttccac taattcaata agtatgtcat gaaatacgtt  2640
gtgaagagca tccagaaata atgaaaagaa acaacgaaac tgggtcggcc tgttgtttct  2700
tttctttacc acgtgatctg cggcatttac aggaagtcgc gcgtttgcg cagttgttgc  2760
aacgcagcta cggctaacaa agccagtgg aactcgactg atgtgttagg gcctaaaact  2820
ggtggtgaca gctgaagtga actattcaat ccaatcatgt catggctgtc acaaagacct  2880
tgcggaccgc acgtacgaac acatacgtat gctaatatgt gttttgatag tacccagtga  2940
tcgcagacct gcaattttt tgtaggtttg gaagaatata taaaggttgc actcattcaa  3000
gatagttttt ttcttgtgtg tctattcatt ttattattgt ttgtttaaat gttaaaaaaa  3060
ccaagaactt agtttcaaat taaattcatc acacaaacaa acaaaacaaa atgaacattg  3120
ttgtttgttt gaagcaagtt ccagacactg ctgaagtcag aattgaccca gtcaagggta  3180
ctttaatcag agaaggtgtt ccatctatca tcaacccaga cgacaagaac gctttggaag  3240
aagctttggt tttgaaggac aactacggtg ctcacgttac cgtcatttcc atgggtccac  3300
ctcaagccaa gaacgctttg gttgaagctt tggccatggg tgctgatgaa gctgtcttat  3360
tgactgacag agctttcggt ggtgctgata ctttagctac ctctcacacc attgctgctg  3420
gtatcaagaa attgaaatac gatatcgtct ttgccggtcg tcaagccatc gatggtgata  3480
ccgctcaagt cggtccagaa attgctgaac atttgggtat tccacaagtc acctacgttg  3540
aaaaggttga agttgacggt gacactttga agatcagaaa ggcttgggaa gacggttacg  3600
aagttgttga agtcaagact ccagttctat tgactgccat caaggaattg aacgttccaa  3660
gatacatgtc cgttgaaaag atcttcggtg ctttcgacaa ggaagtcaag atgtggactg  3720
ctgatgatat cgatgtcgac aaggccaact tgggtttgaa aggttctcca accaaggtca  3780
agaaatcttc taccaaggaa gtcaagggtc aaggtgaagt cattgacaaa ccagtcaagg  3840
aagctgccgc ttacgttgtt tccaagttga aggaagaaca ctacatctaa agcccgggcg  3900
gagattgata agactttct agttgcatat cttttatatt taaatcttat ctattagtta  3960
attttttgta atttatcctt atatatagtc tggttattct aaaaatatcat ttcagtatct  4020
aaaaattccc ctcttttttc agttatatct taacaggcga cagtccaaat gttgatttat  4080
cccagtccga ttcatcaggg ttgtgaagca tttttgtcaat ggtcgaaatc acatcagtaa  4140
tagtgcctct tacttgcctc atagaattc tttctcttaa cgtcaccgtt tggtctttta  4200
tagtttcgaa atctatggtg ataccaaatg gtgttcccaa ttcatcgtta cgggcgtatt  4260
ttttaccaat tgaagtattg gaatcgtcaa ttttaaagta tatctctctt ttacgtaaag  4320
cctgcgagat cctcttaagt atagcgggga agccatcgtt attcgatatt gtcgtaacaa  4380
atactttgat cggcgctatg tttaaatgtt taaacatgga cagatatgcg atgaaaacgc  4440
taagtgatac tccaaatggt gaaaggtacg atgcttggaa acaatacttg gaaatcaccg  4500
gaaacaccat atgcggcgaa aagccaatta gtgtgatact aagtgcttta tcgaaaatcc  4560
gtgatgccgg tccttcaggc atcaaatttc agtggcctaa ttattcacag agttctcatg  4620
tgacaagtat tgatgatagt agtgtcagtt atgcttcagg ttatgttact ataggataat  4680
gatcacggct aaaacggtcg aatgtaagca tatatctttc gattgtataa ttgttcccaa  4740
atactacagc atctcaagga aaaaaaaaca aaaacttcca aaaaaatcga atccctgagg  4800
aatctttaat acattttcaa tctatttaag ttttataaac gtgtatatga gatgtcatga  4860
gcatgaatta ttaataataa aaactaaatc attaaagtaa cttaaggagt taaagcccgg  4920
gctttaattg ttagcagcct tgacttgagc aatcaattct ggaacaacct tgttgacatc  4980
accgacaatg gccaaatcag caaccttcat gattggagct tcgacatctt tgttgatggc  5040
aatgatgtag tcagagtctt gcataccagc caagtgttgg atggcaccag agataccaca  5100
agcaatgtac aaagttggtc tgacggtctt accggtttga ccgacttgca agtccttgtc  5160
aacccattcc ttttcaatgg cagctctgga agcagcaatg gtaccaccca acaaagaagc  5220
taattcttcc aatttttcga agttttcctt ggaaccaaca ccacgaccac cagcaaccaa  5280
aaccttggct tcaccgatat cagcaatgtc cttggccaat ttgacaacct tggaaacctt  5340
ggttctgata tcagaagcag tcaatttgat ggcaaccttt tcgatcttgt catcagaaac  5400
gttagcatcg ttaactggca attttttcaaa gacacctggt ctgacggtgg ccatttgagg  5460
tctgtggtca gaacagacaa tggtagcaat caagttacca ccgaaagctg gtctggtagc  5520
caacaagtca cggttttcga catcgatatc caaagaggta cagtcagcag tcaaaccagt  5580
agacaatctg gcagcaattc ttggacccaa gtctctaccg atgaaagtag caccgatgaa  5640
taagatttct ggctttcttt cgttgaccaa gtcacagata accttggcgt aaccgtcagt  5700
ggagaaatga gctaataatt cgttgtcagc agccaaaacc ttgtcagcac cgtgggacaa  5760
caagtccttg gacatctttt cagtgttgtg acccaataag acagcagtca attcaacacc  5820
caattttttca gccatttcct taccctttacc tagcaattcc aaagaaacct tttgtaattc  5880
accatctctt tgttcagcga aaacccagac acccttgtag tcagccttgt tcatgtttag  5940
ttaattatag ttcgttgacc gtatattcta aaaacaagta ctccttaaaa aaaaaccttg  6000
aagggaataa acaagtagaa tagatagaga gaaaaataga aaatgcaaga gaatttatat  6060
attagaaaga gagaaagaaa aatggaaaaa aaaaaatagg aaaagccaga aatagcacta  6120
gaaggagcga caccagaaaa gaaggtgatg gaaccaattt agctatatat agttaactac  6180
cggctcgatc atctctgcct ccagcatagt cgaagaagaa tttttttttt cttgaggctt  6240
ctgtcagcaa ctcgtatttt ttctttcttt tttggtgagc ctaaaaagtt cccacgttct  6300
cttgtacgac gccgtcacaa acaaccttat gggtaatttg tcgcggtctg ggtgtataaa  6360
tgtgtgggtg caggccggcc gtttaaacgg gccgccaccg cggtggagct ccagcttttg  6420
ttcccttag tgagggttaa ttgcgcgctt ggcgtaatca tggtcatagc tgtttcctgt  6480
gtgaaattgt tatccgctca caattccaca acacatagga gccggaagca taaagtgtaa  6540
agcctggggt gcctaatgag tgaggtaact cacattaatt gcgttgcgct cactgcccgc  6600
tttccagtcg ggaaacctgt cgtgccagct gcattaatga atcggccaac gcgcggggag  6660
aggcggtttg cgtattgggc gctcttccgc ttcctcgctc actgactcgc tgcgctcggt  6720
cgttcggctg cggcgagcgg tatcagctca ctcaaaggcg gtaatacggt tatccacaga  6780
atcagggat aacgcaggaa agaacatgtg agcaaaaggc cagcaaaagg ccaggaaccg  6840
taaaaaggcc gcgttgctgg cgtttttcca taggctccgc ccccctgacg agcatcacaa  6900
```

-continued

```
aaatcgacgc tcaagtcaga ggtggcgaaa cccgacagga ctataaagat accaggcgtt   6960
tcccctgga  agctccctcg tgcgctctcc tgttccgacc ctgccgctta ccggatacct   7020
gtccgccttt ctcccttcgg gaagcgtggc gctttctcat agctcacgct gtaggtatct   7080
cagttcggtg taggtcgttc gctccaagct gggctgtgtg cacgaacccc ccgttcagcc   7140
cgaccgctgc gccttatccg gtaactatcg tcttgagtcc aacccggtaa gacacgactt   7200
atcgccactg gcagcagcca ctggtaacag gattagcaga gcgaggtatg taggcggtgc   7260
tacagagttc ttgaagtggt ggcctaacta cggctacact agaaggacag tatttggtat   7320
ctgcgctctg ctgaagccag ttaccttcgg aaaaagagtt ggtagctctt gatccggcaa   7380
acaaaccacc gctggtagcg gtggtttttt tgtttgcaag cagcagatta cgcgcagaaa   7440
aaaaggatct caagaagatc ctttgatctt ttctacgggg tctgacgctc agtggaacga   7500
aaactcacgt taagggattt tggtcatgag attatcaaaa aggatcttca cctagatcct   7560
tttaaattaa aaatgaagtt ttaaatcaat ctaaagtata tatgagtaaa cttggtctga   7620
cagttaccaa tgcttaatca gtgaggcacc tatctcagcg atctgtctat ttcgttcatc   7680
catagttgcc tgactccccg tcgtgtagat aactacgata cgggagggctt accatctgg   7740
ccccagtgct gcaatgatac cgcgagaccc acgctcaccg gctccagatt tatcagcaat   7800
aaaccagcca gccggaaggg ccgagcgcag aagtggtcct gcaactttat ccgcctccat   7860
ccagtctatt aattgttgcc gggaagctag agtaagtagt tcgccagtta atagtttgcg   7920
caacgttgtt gccattgcta caggcatcgt ggtgtcacgc tcgtcgtttg gtatggcttc   7980
attcagctcc ggttcccaac gatcaaggcg agttacatga tcccccatgt tgtgcaaaaa   8040
agcggttagc tccttcggtc ctccgatcgt tgtcagaagt aagttggccg cagtgttatc   8100
actcatggtt atggcagcac tgcataattc tcttactgtc atgccatccg taagatgctt   8160
ttctgtgact ggtgagtact caaccaagtc attctgagaa tagtgtatgc ggcgaccgag   8220
ttgctcttgc ccggcgtcaa tacgggataa taccgcgcca catagcagaa ctttaaaagt   8280
gctcatcatt ggaaaacgtt cttcggggcg aaaactctca aggatcttac cgctgttgag   8340
atccagttcg atgtaaccca ctcgtgcacc caactgatct tcagcatctt ttactttcac   8400
cagcgtttct gggtgagcaa aaacaggaag gcaaaatgcc gcaaaaaagg gaataagggc   8460
gacacggaaa tgttgaatac tcatactctt cctttttcaa tattattgaa gcatttatca   8520
gggttattgt ctcatgagcg gatacatatt tgaatgtatt tagaaaaata aacaaatagg   8580
ggttccgcgc acatttcccc gaaaagtgcc acctgacgtc taagaaacca ttattatcat   8640
gacattaacc tataaaaata ggcgtatcac gaggcccttt cgtc                    8684
```

```
SEQ ID NO: 44          moltype = DNA  length = 12314
FEATURE                Location/Qualifiers
misc_feature           1..12314
                       note = pBOL115
source                 1..12314
                       mol_type = other DNA
                       organism = synthetic construct
SEQUENCE: 44
tcgcgcgttt cggtgatgac ggtgaaaacc tctgacacat gcagctcccg gagacggtca   60
cagcttgtct gtaagcggat gccgggagca gacaagcccg tcaggcgcg  tcagcgggtg   120
ttggcgggtg tcgggctgg  cttaactatg cggcatcaga gcagattgta ctgagagtgc   180
accataccac agcttttcaa ttcaattcat catttttttt ttattctttt tttgatttc    240
ggtttctttg aaattttttt gattcggtaa tctccgaaca gaaggaagaa cgaaggaagg   300
agcacagact tagattggta tatatacgca tatgtagtgt tgaagaaaca tgaaattgcc   360
cagtattctt aacccaactg cacagaacaa aaacctgcag gaaacgaaga taaatcatgt   420
cgaaagctac atataaggaa cgtgctgcta ctcatcctag tcctgttgct gccaagctat   480
ttaatatcat gcacgaaaag caaacaaact tgtgtgcttc attggatgtt cgtaccacca   540
aggaattact ggagttagtt gaagcattag gtcccaaaat ttgtttacta aaaacacatg   600
tggatatctt gactgatttt tccatggagg gcacagttaa gccgctaaag gcattatccg   660
ccaagtacaa tttttttactc ttcgaagaca gaaaatttgc tgacattggt aatacagtca   720
aattgcagta ctctgcgggg gtatacagaa tagcagaatg ggcagacatt acgaatgcac   780
acggtgtggt gggcccaggt attgttagcg gtttgaagca ggcggcagaa gaagtaacaa   840
aggaacctag aggccttttg atgttagcag aattgtcatg caagggctcc ctatctactg   900
gagaatatac taaagggtact gttgacattg cgaagagcga caaagatttt gttatcggct   960
ttattgctca aagagacatg ggtggaagag atgaaggtta cgattggttg attatgacac  1020
ccggtgtggg tttagatgac aagggagacg cattgggtca acagtataga accgtggatg  1080
atgtggtctc tacaggatct gacattatta ttgttggaag aggactattt gcaaagggaa  1140
gggatgctaa ggtagagggt gaacgttaca gaaaagcagg ctgggaagca tatttggaaa  1200
gatgcggcca gcaaaactaa aaaactgtat tataagtaaa tgcatgtata ctaaactcac  1260
aaattagagc ttcaatttaa ttatatcagt tattacccta tgcggtgtga ataccgcac   1320
agatgcgtaa ggagaaaata ccgcatcagg aaattgtaaa cgttaatatt ttgttaaaat  1380
tcgcgttaaa ttttttgttaa atcagctcat tttttaacca ataggccgaa atcggcaaaa  1440
tcccttataa atcaaaagaa tagaccgaga tagggttgag tgttgttcca gtttggaaca  1500
agagtccact attaaagaac gtggactcca acgtcaaagg gcgaaaaacc gtctatcagg  1560
gcgatggccc actacgtgaa ccatcaccct aatcaagttt tttggggtcg aggtgccgta  1620
aagcactaaa tcggaaccct aaagggagcc cccgatttag agcttgacgg ggaaagccgg  1680
cgaacgtggc gagaaaggaa gggaagaaag cgaaaggagc gggcgctagg cgctggcaa   1740
gtgtagcggt cacgctgcgc gtaaccacca cacccgccgc gcttaatgcg ccgctacagg  1800
gcgcgtcgcg ccattcgcca ttcaggctgc gcaactgttg ggaagggcga tcggtgcggg  1860
cctcttcgct attacgccag ctggcgaaag gggatgtgc  tgcaaggcga ttaagttggg  1920
taacgccagg gttttcccag tcacgacgtt gtaaaacgac ggccagtgag cgcgcgtaat  1980
acgactcact atagggcgaa ttgggtaccg gccccccct  cgaggtcgac ggtatcgata  2040
agcttgatat cgaattcctg cagcccgggg gatccactag ttctagagcg gcccatttta  2100
acggccggca ctagatcaga gggtggtaaa tgaagtgtaa tagtattcat ttttcttata  2160
aatcatccct tccgtgattt atacaaaaga agaggagaat atgctgaata cttggtatat  2220
tactctacat tatactctta tcttgacggg tattctgagc atcttactca gtttcaagat  2280
cttttaatgt ccaaaaacat ttgagccgat ctaaatactt ctgtgttttc attaatttat  2340
aaattgtact cttttaagac atggaaagta ccaacatcgg ttgaaacagt ttttcattta  2400
```

```
cttatggttt attggttttt ccagtgaatg attatttgtc gttacccttt cgtaaaagtt   2460
caaacacgtt tttaagtatt gtttagttgc tctttcgaca tatatgatta tccctgcgcg   2520
gctaaagtta aggatgcaaa aaacataaga caactgaagt taatttacgt caattaagtt   2580
ttccagggta atgatgtttt gggcttccac taattcaata agtatgtcat gaaatacgtt   2640
gtgaagagca tccagaaata atgaaaagaa acaacgaaac tgggtcggcc tgttgtttct   2700
tttctttacc acgtgatctg cggcatttac aggaagtcgc gcgtttttgcg cagttgttgc   2760
aacgcagcta cggctaacaa agccagtgg aactcgactg atgtgttagg gcctaaaact   2820
ggtggtgaca gctgaagtga actattcaat ccaatcatgt catggctgtc acaaagacct   2880
tgcggaccgc acgtacgaac acatacgtat gctaatatgt gttttgatag tacccagtga   2940
tcgcagacct gcaatttttt tgtaggtttg gaagaatata taaaggttgc actcattcaa   3000
gatagttttt ttcttgtgtg tctattcatt ttattattgt ttgtttaaat gttaaaaaaa   3060
ccaagaactt agtttcaaat taaattcatc acacaaacaa acaaaacaaa atgaacattg   3120
ttgtttgttt gaagcaagtt ccagacactg ctgaagtcag aattgaccca gtcaagggta   3180
ctttaatcag agaaggtgtt ccatctatca tcaacccaga cgacaagaac gctttggaag   3240
aagctttggt tttgaaggac aactacggtg ctcacgttac cgtcatttcc atgggtccac   3300
ctcaagccaa gaacgctttg gttgaagctt tggccatggg tgctgatgaa gctgtcttat   3360
tgactgacag agctttcggt ggtgctgata cttttagctac ctctcacacc attgctgctg   3420
gtatcaagaa attgaaatac gatatcgtct ttgccggtcg tcaagccatc gatggtgata   3480
ccgctcaagt cggtccagaa attgctgaac atttgggtat tccacaagtc acctacgttg   3540
aaaaggttga agttgacggt gacactttga agatcagaaa ggcttgggaa gacggttacg   3600
aagttgttga agtcaagact ccagttctat tgactgccat caaggaattg aacgttccaa   3660
gatacatgtc cgttgaaaag atcttcggtg ctttcgacaa ggaagtcaag atgtggactg   3720
ctgatgatat cgatgtcgac aaggccaact tgggtttgaa aggttctcca accaaggtca   3780
agaaatcttc taccaaggaa gtcaagggtc aaggtgaagt cattgacaaa ccagtcaagg   3840
aagctgccgc ttacgttgtt tccaagttga aggaagaaca ctacatctaa agcccgggcg   3900
gagattgata agacttttct agttgcatat cttttatatt taaatcttat ctattagtta   3960
attttttgta atttatcctt atatatagtc tggttattct aaaatatcat ttcagtatct   4020
aaaaaattccc ctcttttttc agttatatct taacaggcga cagtccaaat gttgatttat   4080
cccagtccga ttcatcaggg ttgtgaagca ttttgtcaat ggtcgaaatc acatcagtaa   4140
tagtgcctct tacttgcctc atagaatttc tttctcttaa cgtcaccgtt tggtctttta   4200
tagtttcgaa atctatggtg ataccaaatg gtgttcccaa ttcatcgtta cgggcgtatt   4260
ttttaccaat tgaagtattg gaatcgtcaa ttttaaagta tatctctctt ttacgtaaag   4320
cctgcgagat cctcttaagt atagcgggga agccatcgtt attcgatatt gtcgtaacaa   4380
atactttgat cggcgctatg tttaaatgtt taaacatgga cagatatgcg atgaaaacgc   4440
taagtgatac tccaaatggt gaaaggtacg atgcttggaa acaatacttg gaaatcaccg   4500
gaaacaccat atgcggcgaa aagccaatta gtgtgatact aagtgcttta tcgaaaatcc   4560
gtgatgccgg tccttcaggc atcaaatttc agtggcctaa ttattcacag agttctcatg   4620
tgacaagtat tgatgatagt agtgtcagtt atgcttcagg ttatgttact ataggataat   4680
gatcacggct aaaacggtcg aatgtaagca tatatctttc gattgataaa ttgttcccaa   4740
atactacagc atctcaagga aaaaaaaaca aaaacttcca aaaaaatcga atccctgagg   4800
aatctttaat acattttcaa tctatttaag ttttataaac gtgtatatga gatgtcatga   4860
gcatgaatta ttaataataa aaactaaatc attaaagtaa cttaaggagt taaagcccgg   4920
gctttaattg ttagcagcct tgacttgagc aatcaattct ggaacaacct tgttgacatc   4980
accgacaatg gccaaatcag caaccttcat gattggagct tcgacatctt tgttgatggc   5040
aatgatgtag tcagagtctt gcataccagc caagtgttgg atggcaccag agataccaca   5100
agcaatgtac aaagttggtc tgacggtctt accggtttga ccgacttgca agtccttgtc   5160
aacccattcc ttttcaatgg cagctctgga agcagcaatg gtaccaccca acaaagaagc   5220
taattcttcc aattttttcga agttttcctt ggaaccaaca ccacgaccac cagcaaccaa   5280
aaccttggct tcaccgatat cagcaatgtc cttggccaat ttgacaacct tggaaaacctt   5340
ggttctgata tcagaagcag tcaatttgat ggcaaccttt tcgatcttgt catcagaaac   5400
gttagcatcg ttaactggca attttttcaaa gacacctggt ctgacggtgg ccatttgagg   5460
tctgtggtca gaacagacaa tggtagcaat caagttacca ccgaaagctg gtctggtagc   5520
caacaagtca cggttttcga catcgatatc caaagaggta cagtcagcag tcaaaccagt   5580
agacaatctg gcagcaattc ttggacccaa gtctctaccg atgaaagtag caccgatgaa   5640
taagatttct ggcttttctt cgttgaccaa gtcacagata accttggcgt aaccgtcagt   5700
ggagaaatga gctaataatt cgttgtcagc agccaaaacc ttgtcagcac cgtgggacaa   5760
caagtccttg gacatctttt cagtgttgtg acccaataag acagcagtca attcaacacc   5820
caattttttca gccatttcct taccctttacc tagcaattcc aaagaaacct tttgtaattc   5880
accatctctt tgttcagcga aaacccagac acccttgtag tcagccttgt tcatgtttag   5940
ttaattatag ttcgttgacc gtatattcta aaaacaagta ctccttaaaa aaaaacccttg   6000
aagggaataa acaagtagaa tagatagaga gaaaaataga aaatgcaaga gaatttatat   6060
attagaaaga gagaaagaaa aatggaaaaa aaaaaatagg aaaagccaga aatagcacta   6120
gaaggagcga caccagaaaa gaaggtgatg gaaccaattg agctatatat agttaactac   6180
cggctcgatc atctctgcct ccagcatagt cgaagaagaa tttttttttt cttgaggctt   6240
ctgtcagcaa ctcgtatttt ttctttcttt tttggtgagc ctaaaaagtt cccacgttct   6300
cttgtacgac gccgtcacaa acaaccttat gggtaatttg tcgcggtctg ggtgtataaa   6360
tgtgtgggtc caggccggcc gtttaaacgg ccgccaccg cggtggagcc tgtgtggaag   6420
aacgattaca acaggtgttg tcctctgagg acataaaata cacaccgaga ttcatcaact   6480
cattgctgtga gttagcatat ctacaattgg gtgaaatggg gagcgatttg caggcatttg   6540
ctcggcatgc cggtagaggt gtggtcaata agagcgacct catgctatac ctgagaaagc   6600
aacctgacct acaggaaaga gttactcaag aataagaatt ttcgttttaa aacctaagag   6660
tcactttaaa atttgtatac acttattttt tttataactt atttaataat aaaaatcata   6720
aatcataaga aattcgctcg agtcgactgc agttactgc ttgtagtcgt aagaagtttg   6780
gatgatatcg ttgatttcag aaatcaaagc ttcctttggg ttggcagtgg tacattggtc   6840
ttcgaaagcc aattcagcca ttctgtcaat ggattcgttc aattcttctt cagagacacc   6900
ttgagatttc aagttcattt caataccaac agattgacct aattcgtaga cagccttggc   6960
caaagattca accaaagctt cagtggtgtt acctttcaaa cctaagaact ggcgatatc   7020
agcgtaatcg gtgtcagctc tgaagaattc gtactttggg aacaaagcgt gcttttgagg   7080
gtccttggcg ttgtatctga tgatgtgagg caacaagatg gcgttagctc taccatgtgg   7140
```

```
aataccgtat tcaccaccaa ttttgtgagc aatggagtga gcaataccca agaaagcgtt   7200
agcaaaggcc ataccggcca aagtagaagc gttgtgcatc ttttctctgg aaaccttgtc   7260
acctttttca acggaagatt tcaagtattc aaaggtcaat ttgatagctt gtagggacaa   7320
acctctggtg taatcggagg ccatgacaga aacgtaagat tccatagcgt gagtcaaaac   7380
gtccataccg gtatcagcag tgacagattt tgggacggac atgacaaatt gagggtcaat   7440
gatggcgaca tctggagtca aagcgaaatc agccaatggg tatttgacgt tggtttcaga   7500
gtcagtgata acagcaaatg gagtgacttc agaaccagta ccagaagtgg ttggaataca   7560
gatgaaagtg gcgttttctg gcataccaat cttgtaggtt ctcttaccaa tgtccaagaa   7620
tttttgcttg gcaccgaaga aagaagtttc tggatgttcg aagaacatcc acatagcctt   7680
ggcagcatcc atggcagaac caccacccaa agcaatgatg gtgtctggtt ggaaatcgac   7740
catcatttcc aaacccttgt agacagtgtt ggtggatgga tttggttcaa cttcagagaa   7800
gatcttgatt tgaggttgtt cagttctttg acgtaagacg ttttcgacgg ttttggtgta   7860
accaaattca accatacctg ggtcacaaac gatcatgacc ttttcaatct tgtccatggt   7920
ggtcaaggac atgatagcgt tttcttcgaa atagatttga gctggaacct tgaagatttg   7980
agtgttgttt cttctcttgg caatggtctt gatgttcaac aaatcggtag cagagacgtt   8040
gtgggagatg gagtttctac cgtaagaacc acaacccaaa gtcaaggatg gaatcaattc   8100
gttgtacatg tcaccgatac caccaacagc agatggagtg ttgaccaaaa cacgacaagc   8160
cttcattctt agaccgaaat cctttgcaa agtttcgtct tcagtgtgga taacagcagt   8220
gtgacctaaa ccaccgaagt gcaaagtgtc ttcacagatt tggaaagctt gcttggtaga   8280
ttgagccttg actaaagcca aaactggaga caacttttct ctggacaatg ggtagtcaga   8340
accgacaccg gagatttcag caatgatcaa tttggtgttt tctggaactg ggataccggc   8400
caattcagca atttcaacag cagacttacc aacgatatct ggcttgatac cagtcttttg   8460
ttcgttcatg atggcgtttt ctaatctttg taattcgtcc ttcttgacga agtaagcttg   8520
gtgagccttg aattcattgg tgacatcctt gtagatttcc ttgtcaatga caacaacttg   8580
ttcagaagca cagatcatac cattatcgaa agtcttggaa ccgatgatat cgttgacagc   8640
acgcttgata tgagcagtct tttcgatgta agatggaacg ttacctggac caacacccaa   8700
agctggttta ccagtggagt aagcagactt aaccatacca gaaccaccgg tagccaagac   8760
taaagcaata cccttgtggt tcatcaattg cttggtagct tcaatggatg gaacttcaat   8820
ccattggatg atatcctttg gagcaccagc cttcatggca gcttccaaaa caacttcagc   8880
agctctcttg gaagattctt gagcagatgg gtggaaagcg aaaataattg ggttaccagt   8940
cttgatggca atcatagcct tgaagatggt ggtagaagtt gggttggtgg ttggagtgac   9000
accacagatg acaccaattg gttcagcaac gtaggtcaaa ccctttttctt tgtcttcacc   9060
aatgatacca acagtcttgt tgtccttgat ggagttccag atgtattcag aggcgtataa   9120
gttcttgata gccttgtctt cgtagatacc tctaccggtt tcttcatgag ccaacttggc   9180
caaaaccatg tgttggtcaa cagcagccaa ggacatttgg tggacaatgt ggtcaatttc   9240
ttcttgagac ttcttggaca aagcttccaa agccttctta cctttgtcag ctaaagcatc   9300
aatcatgatg gcaacttctt gttccttgga acctctgttt tccttttctg gaatggtcaa   9360
cattttttac tagttctaga atccgtcgaa actaagttct ggtgttttaa aactaaaaaa   9420
aagactaact ataaaagtag aatttaagaa gtttaagaaa tagatttaca gaattacaat   9480
caatacctac cgtctttata tacttattag tcaagtaggg gaataaatttc agggaactgg   9540
tttcaacctt ttttttcagc ttttttccaaa tcagagagag cagaaggtaa tagaaggtgt   9600
aagaaaatga gatagataca tgcgtgggtc aattgccttg tgtcatcatt tactccaggc   9660
aggttgcatc actccattga ggttgtgccc gttttttgcc tgtttgtgcc cctgttctct   9720
gtagttgcgc taagagaatg gacctatgaa ctgatggttg gtgaagaaaa caatattttg   9780
gtgctgggat tcttttttt tctggatgcc agcttaaaaa gcgggctcca ttatatttag   9840
tggatgccag gaataaactg ttcacccaga cacctacgat gttatatatt ctgtgtaacc   9900
cgcccctat tttgggcatg tacgggttac agcagaatta aaaggctaat tttttgacta   9960
aataaagtta ggaaaatcac tactattaat tatttacgta ttctttgaaa tggcgagtat  10020
tgataatgat aaactgagct ccagcttttg ttcccttttag tgagggttaa ttgcgcgctt  10080
ggcgtaatca tggtcatagc tgtttcctgt gtgaaattgt tatccgctca caattccaca  10140
caacatagga gccggaagca taaagtgtaa agcctggggt gcctaatgag tgaggtaact  10200
cacattaatt gcgttgcgct cactgcccgc tttccagtcg ggaaacctgt cgtgccagct  10260
gcattaatga atcggccaac gcgcggggag aggcggtttg cgtattgggc gctcttccgc  10320
ttcctcgctc actgactcgc tgcgctcggt cgttcggctg cggcgagcgg tatcagctca  10380
ctcaaaggcg gtaatacggt tatccacaga atcaggggat aacgcaggaa agaacatgtg  10440
agcaaaaggc cagcaaaagg ccaggaaccg taaaaaggcc gcgttgctgg cgttttttcca  10500
taggctccgc ccccctgacg agcatcacaa aaatcgacgc tcaagtcaga ggtggcgaaa  10560
cccgacagga ctataaagat accaggcgtt tccccctgga agctccctcg tgcgctctcc  10620
tgttccgacc ctgccgctta ccggatacct gtccgccttt ctcccttcgg gaagcgtggc  10680
gctttctcat agctcacgct gtaggtatct cagttcggtg taggtcgttc gctccaagct  10740
gggctgtgtg cacgaacccc ccgttcagcc cgaccgctgc gccttatccg gtaactatcg  10800
tcttgagtcc aacccggtaa gacacgactt atcgccactg gcagcagcca ctggtaacag  10860
gattagcaga gcgaggtatg taggcggtgc tacagagttc ttgaagtggt ggcctaacta  10920
cggctacact agaaggacag tatttggtat ctgcgctctg ctgaagccag ttaccttcgg  10980
aaaaagagtt ggtagctctt gatccggcaa acaaaccacc gctggtagcg gtggtttttt  11040
tgtttgcaag cagcagatta cgcgcagaaa aaaaggatct caagaagatc ctttgatctt  11100
ttctacgggg tctgacgctc agtggaacga aaactcacgt taagggattt tggtcatgag  11160
attatcaaaa aggatcttca cctagatcct tttaaattaa aaatgaagtt ttaaatcaat  11220
ctaaagtata tatgagtaaa cttggtctga cagttaccaa tgcttaatca gtgaggcacc  11280
tatctcagcg atctgtctat ttcgttcatc catagttgcc tgactccccg tcgtgtagat  11340
aactacgata cgggagggct taccatctgg ccccagtgct gcaatgatac cgcgagaccc  11400
acgctcaccg gctccagatt tatcagcaat aaaccagcca gccggaaggg ccgagcgcag  11460
aagtggtcct gcaactttat ccgcctccat ccagtcatt aattgttgcc gggaagctag  11520
agtaagtagt tcgccagtta atagtttgcg caacgttgtt gccattgcta caggcatcgt  11580
ggtgtcacgc tcgtcgtttg gtatggcttc attcagctcc ggttcccaac gatcaaggcg  11640
agttacatga tcccccatgt tgtgcaaaaa agcggttagc tccttcggtc ctccgatcgt  11700
tgtcagaagt aagttggccg cagtgttatc actcatggtt atggcagcac tgcataattc  11760
tcttactgtc atgccatccg taagatgctt ttctgtgact ggtgagtact caaccaagtc  11820
attctgagaa tagtgtatgc ggcgaccgag ttgctcttgc ccggcgtcaa tacgggataa  11880
```

-continued

```
taccgcgcca catagcagaa ctttaaaagt gctcatcatt ggaaaacgtt cttcggggcg   11940
aaaactctca aggatcttac cgctgttgag atccagttcg atgtaaccca ctcgtgcacc   12000
caactgatct tcagcatctt ttactttcac cagcgtttct gggtgagcaa aaacaggaag   12060
gcaaaatgcc gcaaaaaagg gaataagggc gacacggaaa tgttgaatac tcatactctt   12120
cctttttcaa tattattgaa gcatttatca gggttattgt ctcatgagcg gatacatatt   12180
tgaatgtatt tagaaaaata aacaaatagg ggttccgcgc acatttcccc gaaaagtgcc   12240
acctgacgtc taagaaacca ttattatcat gacattaacc tataaaaata ggcgtatcac   12300
gaggcccttt cgtc                                                     12314

SEQ ID NO: 45              moltype = DNA   length = 11180
FEATURE                   Location/Qualifiers
misc_feature              1..11180
                          note = pBOL116
source                    1..11180
                          mol_type = other DNA
                          organism = synthetic construct
SEQUENCE: 45
tcgcgcgttt cggtgatgac ggtgaaaacc tctgacacat gcagctcccg gagacggtca   60
cagcttgtct gtaagcggat gccgggagca gacaagcccg tcaggcgcg tcagcgggtg   120
ttggcgggtg tcgggctgg cttaactatg cggcatcaga gcagattgta ctgagagtgc   180
accataccac agcttttcaa ttcaattcat cattttttt ttattctttt ttttgatttc   240
ggtttctttg aaatttttt gattcggtaa tctccgaaca gaaggaagaa cgaaggaagg   300
agcacagact tagattggta tatatacgca tatgtagtgt tgaagaaaca tgaaattgcc   360
cagtattctt aacccaactg cacagaacaa aaacctgcag gaaacgaaga taaatcatgt   420
cgaaagctac atataaggaa cgtgctgcta ctcatcctag tcctgttgct gccaagctat   480
ttaatatcat gcacgaaaag caaacaaact tgtgtgcttc attggatgtt cgtaccacca   540
aggaattact ggagttagtt gaagcattag gtcccaaaat ttgtttacta aaaacacatg   600
tggatatctt gactgatttt tccatggagg gcacagttaa gccgctaaag gcattatccg   660
ccaagtacaa tttttactc ttcgaagaca gaaaatttgc tgacattggt aatacagtca   720
aattgcagta ctctgcgggt gtatacagaa tagcagaatg ggcagacatt acgaatgcac   780
acggtgtggt gggcccaggt attgttagcg gtttgaagca ggcggcagaa gaagtaacaa   840
aggaacctag aggcctttg atgttagcag aattgtcatg caagggctcc ctatctactg   900
gagaatatac taagggtact gttgacattg cgaagagcga caaagatttt gttatcggct   960
ttattgctca aagagacatg ggtggaagag atgaaggtta cgattggttg attatgacac   1020
ccggtgtggg tttagatgac aagggagacg cattgggtca acagtataga accgtgatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa ttttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg cgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact ataggcgaa ttgggtaccg ggccccccct cgaggtcgac ggtatcgata   2040
agcttgatat cgaattcctg cagcccgggg gatccactag ttctagagcg gcccatttaa   2100
acggccggcc ctagatcaga gggtggtaaa tgaagtgtaa tagtattcat ttttcttata   2160
aatcatccct tccgtgattt atacaaaaga agaggagaat atgctgaata cttggtatat   2220
tactctacat tatactctta tcttgacggg tattctgagc atcttactca gtttcaagat   2280
cttttaatgt ccaaaaacat ttgagccgat ctaaatactt ctgtgttttc attaatttat   2340
aaattgtact ctttttaagac atggaaagta ccaacatcgg ttgaaacagt ttttcattta   2400
cttatggttt attggttttt ccagtgaatg attatttgtc gttacccttt cgtaaaagtt   2460
caaacacgtt tttaagtatt gtttagttgc tctttcgaca tatatgatta tccctgccgcg   2520
gctaaagtta aggatgcaaa aaacataaga caactgaagt taatttacgt caattaagtt   2580
ttccagggta atgatgtttt gggcttccac taattcaata agtatgtcat gaaatacgtt   2640
gtgaagagca tccagaaata atgaaaagaa acaacgaaac tgggtcggcc tgttgtttct   2700
tttctttacc acgtgatctg cggcatttac aggaagtcgc gcgttttgcg cagttgttgc   2760
aacgcagcta cggctaacaa agcctagtgg aactcgacta atgtgttagg gcctaaaact   2820
ggtggtgaca gctgaagtga actattcaat ccaatcatgt catggctgtc acaaagacct   2880
tgcggaccgc acgtacgaac acatacgtat gctaatatgt gtttttgatag tacccagtga   2940
tcgcagacct gcaatttttt tgtaggtttg aagaatatat aaaggttgc actcattcaa   3000
gatagttttt ttcttgtgtg tctattcatt ttattattgt ttgtttaaat gttaaaaaaa   3060
ccaagaactt agtttcaaat taaattcatc acacaaacaa acaaaacaaa atgaacattg   3120
ttgtttgttt gaagcaagtt ccagacactg ctgaagtcag aattgaccca gtcaagggta   3180
ctttaatcag agaaggtgtt ccatctatca tcaacccaga cgacaagaac gctttggaag   3240
aagctttggt tttgaaggac aactacggtc tcacgttac cgtcatttcc atgggtccac   3300
ctcaagccaa gaacgctttg gttgaagctt tggccatggg tgctgatgaa gctgtcttat   3360
tgactgacag agcttcggt ggtgctgata ctttagctac ctctcacacc attgctgctg   3420
gtatcaagaa attgaaatac gatatcgtct ttgccggtcg tcaagccatc gatggtgata   3480
ccgctcaagt cggtccagaa attgctgaac atttgggtat tccacaagtc acctacgttg   3540
aaaaggttga agttgacggt gacactttga agatcagaaa ggcttgggaa gacggttacg   3600
aagttgttga agtcaagact ccagttctat tgactgccat caaggaattg aacgttccaa   3660
gatacatgtc cgttgaaaag atcttcggtg cttttcgacaa ggaagtcaag atgtggactg   3720
```

-continued

```
ctgatgatat cgatgtcgac aaggccaact tgggtttgaa aggttctcca accaaggtca   3780
agaaatcttc taccaaggaa gtcaagggtc aaggtgaagt cattgacaaa ccagtcaagg   3840
aagctgccgc ttacgttgtt tccaagttga aggaagaaca ctacatctaa agcccgggcg   3900
gagattgata agacttttct agttgcatat cttttatatt taaatcttat ctattagtta   3960
attttttgta atttatcctt aaatatagtc tggttattct aaaatatcat ttcagtatct   4020
aaaaattccc ctcttttttc agttatatct taacaggcga cagtccaaat gttgatttat   4080
cccagtccga ttcatcaggg ttgtgaagca ttttgtcaat ggtcgaaatc acatcagtaa   4140
tagtgcctct tacttgcctc atagaatttc tttctcttaa cgtcaccgtt tggtctttta   4200
tagtttcgaa atctatggtg ataccaaatg gtgttcccaa ttcatcgtta cgggcgtatt   4260
ttttaccaat tgaagtattg gaatcgtcaa ttttaaagta tatctctctt ttacgtaaag   4320
cctgcgagat cctcttaagt atagcgggga agccatcgtt attcgatatt gtcgtaacaa   4380
atactttgat cggcgctatg tttaaatgtt taaacatgga cagatatgcg atgaaaacgc   4440
taagtgatac tccaaatggt gaaaggtacg atgcttggaa acaatacttg gaaatcaccg   4500
gaaacaccat atgcggcgaa aagccaatta gtgtgatact aagtgcttta tcgaaaatcc   4560
gtgatgccgg tccttcaggc atcaaatttc agtggcctaa ttattcacag agttctcatg   4620
tgacaagtat tgatgatagt agtgtcagtt atgcttcagg ttatgttact ataggataat   4680
gatcacggct aaaacggtcg aatgtaagca tatatctttc gattgtataa ttgttcccaa   4740
atactacagc atctcaagga aaaaaaaaca aaaacttcca aaaaaatcga atccctgagg   4800
aatctttaat acattttcaa tctatttaag ttttataaac gtgtatatga gatgtcatga   4860
gcatgaatta ttaataataa aaactaaatc attaaagtaa cttaaggagt taaagcccgg   4920
gctttaattg ttagcagcct tgacttgagc aatcaattct ggaacaacct tgttgacatc   4980
accgacaatg gccaaatcag caaccttcat gattggagct tcgacatctt tgttgatggc   5040
aatgatgtag tcagagtctt gcataccagc caagtgttgg atggcaccag agataccaca   5100
agcaatgtac aaagttggtc tgacggtctt accggtttga ccgacttgca agtccttgtc   5160
aacccattcc ttttcaatgg cagctctgga agcagcaatg gtaccaccca acaaagaagc   5220
taattcttcc aatttttcga agtttttcctt ggaaccaaca ccacgaccac cagcaaccaa   5280
aaccttggct tcaccgatat cagcaatgtc cttggccaat ttgacaacct tggaaacctt   5340
ggttctgata tcagaagcag tcaatttgat ggcaaccttt tcgatcttgt catcagaaac   5400
gttagcatcg ttaactggca attttttcaaa gacacctggt ctgacggtgg ccatttgagg   5460
tctgtggtca gaacagacaa tggtagcaat caagttacca ccgaaagctg gtctggtagc   5520
caacaagtca cggttttcga catcgatatc caaagaggta cagtcagcag tcaaaccagt   5580
agacaatctg gcagcaattc ttggacccaa gtctctaccg atgaaagtag caccgatgaa   5640
taagatttct ggctttcttt cgttgaccaa gtcacagata accttggcgt aaccgtcagt   5700
ggagaaatga gctaataatt cgttgtcagc agccaaaacc ttgtcagcac cgtgggacaa   5760
caagtccttg gacatctttt cagtgttgtg acccaataag acagcagtca attcaacacc   5820
caattttttca gccatttcct taccccttacc tagcaattcc aaagaaacct tttgtaattc   5880
accatctctt tgttcagcga aaacccagac acccttgtag tcagccttgt tcatgtttag   5940
ttaattatag ttcgttgacc gtatattcta aaaacaagta ctccttaaaa aaaaacttg   6000
aagggaataa acaagtagaa tagatagaga gaaaaataga aaatgcaaga gaatttatat   6060
attagaaaga gagaaagaaa aatggaaaaa aaaaaatagg aaaagccaga aatagcacta   6120
gaaggagcga caccagaaaa gaaggtgatg gaaccaattt agctatatat agttaactac   6180
cggctcgatc atctctgcct ccagcatagt cgaagaagaa tttttttttt cttgaggctt   6240
ctgtcagcaa ctcgtatttt ttctttcttt tttggtgagc ctaaaaagtt ccacgttct   6300
cttgtacgac gccgtcacaa acaaccttat gggtaatttg tcgcggtctg ggtgtataaa   6360
tgtgtgggtg caggccggcc gtttaaacgg gccgccaccg cggtggagcc tgtgtggaag   6420
aacgattaca acaggtgttg tcctctgagg acataaaata cacaccgaga ttcatcaact   6480
cattgctgga gttagcatat ctacaattgg gtgaaatggg gagcgatttg caggcatttg   6540
ctcggcatgc cggtagaggt gtggtcaata agagcgacct catgctatac ctgagaaagc   6600
aacctgacct acaggaaaga gttactcaag aataagaatt ttcgttttaa aacctaagag   6660
tcactttaaa atttgtatac acttattttt tttataactt atttaataat aaaaatcata   6720
aatcataaga aattcgctcg agtcgactgc agtttacaag ttcaatttgg ccatgatggc   6780
cttaacaatg gcttgaacat cttcgttgtc ttctggttca gctggagcag aagaagaagc   6840
agcaccgaca ccgaaagctt ctctgatttc ttcgacggtg gtggtaccgt aagcaacctt   6900
tctgatgttg aacaagtttt ctggaccaac gttgtcagag gtggcagaac caccaacagc   6960
accacaacct aaagtcaaag atgggactaa gttggtagca ccaccgatac cacccaaaga   7020
acctggagag ttaaccaaaa ttctggaaac aggcttcttc aaagcaaatt ctctaatgat   7080
ttcttcgttt tgagagtgga tgatcaaagt gtgaccagaa ccttggttgt gcaataaagc   7140
caaagacttt tcacaagctt catgccagtc ttcgacggtg tagaaagcca agactggagc   7200
caatttttcc ttagcgtatg gattttttagg agaaacatcg gtttgttcgg atagtaaagat   7260
aacagcatca gatggaatgg aaataccagc caatttggcc aaagcttgga catccttacc   7320
aacgatggct gggtttggag taccgttggc acgtaataga atcttaccaa cctttttcaga   7380
ttcttcagca ttcaagaagt aacccttttg tctcttgaat tcttcgatga tttcagcctt   7440
cttgacggtt tcagcaatga tggattgttc agaagcacag atgacaccgt tgtcgaaagt   7500
gtcagaaccg ataaccttte taacagcagt tggaatgtca gcagttcttt cgatgaaaca   7560
tggaccgtta cctggaccga caccgatggc tggagtacca gaggagtaag cagctctaac   7620
catacccttca ccaccggtag ccaagatcaa agcggtgtcc ttgttcttca tcaattcagc   7680
agtaccttca acggtcaaaa tggacataca ttggatcaaa ccatctggag caccagcttc   7740
aacagcagcc ttttgcatga tcttaacggt ttcagtgatg aacggacag cagttgggtg   7800
tggagagaag acaatggcgt taccagcctt caaagcaatc aagaccttga aaatggcagt   7860
ggaagttggg ttggtagatg gaatcaaacc agcaatgaca cctaatggga cagcaatgtc   7920
aatcaatttc ttttccttgt cttccttcaa gataccaacg gtcttcaaat ccttgatgta   7980
gttgtagaca acaatggagg agaatttgtt cttgatgacc ttgtcttccc atttaccgta   8040
accggtgtct tcgtaagcca atttggccaa tttgacagct tcaacttcag tagccttggc   8100
gatcttttcg atgaccttgt taacagcttc tgggaaaag ttcttgaatt cagcttgagc   8160
cttcttggcc ttggcaatca aagttctaac ttcttggatg gattgcaaat ccttgtccat   8220
gatttccatt ttttactagt tctagaatcc gtcgaaacta agttctggtg ttttaaaact   8280
aaaaaaaaga ctaactataa aagtagaatt taagaagttt aagaaataga tttacagaat   8340
tacaatcaat acctaccgtc tttatatact tattagtcaa gtaggggaat aatttcaggg   8400
aactggtttc aaccttttttt ttcagctttt tccaaatcag agagagcaga aggtaataga   8460
```

-continued

```
aggtgtaaga aaatgagata gatacatgcg tgggtcaatt gccttgtgtc atcatttact   8520
ccaggcaggt tgcatcactc cattgaggtt gtgcccgttt tttgcctgtt tgtgccctg    8580
ttctctgtag ttgcgctaag agaatggacc tatgaactga tggttggtga agaaaacaat   8640
attttggtgc tgggattctt ttttttttctg gatgccagct taaaaagcgg gctccattat   8700
atttagtgga tgccaggaat aaactgttca cccagacacc tacgatgtta tatattctgt   8760
gtaacccgcc ccctattttg ggcatgtacg ggttacagca gaattaaaag gctaattttt   8820
tgactaaata aagttaggaa aatcactact attaattatt tacgtattct ttgaaatggc   8880
gagtattgat aatgataaac tgagctccag cttttgttcc ctttagtgag ggttaattgc   8940
gcgcttggcg taatcatggt catagctgtt tcctgtgtga aattgttatc cgctcacaat   9000
tccacacaac ataggagccg gaagcataaa gtgtaaagcc tggggtgcct aatgagtgag   9060
gtaactcaca ttaattgcgt tgcgctcact gcccgctttc cagtcgggaa acctgtcgtg   9120
ccagctgcat taatgaatcg gccaacgcgc ggggagaggc ggtttgcgta ttgggcgctc   9180
ttccgcttcc tcgctcactg actcgctgcg ctcggtcgtt cggctgcggc gagcggtatc   9240
agctcactca aaggcggtaa tacggttatc cacagaatca ggggataacg caggaaagaa   9300
catgtgagca aaaggccagc aaaaggccag gaaccgtaaa aaggccgcgt tgctggcgtt   9360
tttccatagg ctccgccccc ctgacgagca tcacaaaaat cgacgctcaa gtcagaggtg   9420
gcgaaacccg acaggactat aaagatacca ggcgtttccc cctggaagct ccctcgtgcg   9480
ctctcctgtt ccgaccctgc cgcttaccgg atacctgtcc gcctttctcc cttcgggaag   9540
cgtggcgctt tctcatagct cacgctgtag gtatctcagt tcggtgtagg tcgttcgctc   9600
caagctgggc tgtgtgcacg aaccccccgt tcagcccgac cgctgcgcct tatccggtaa   9660
ctatcgtctt gagtccaacc cggtaagaca cgacttatcg ccactggcag cagccactgg   9720
taacaggatt agcagagcga ggtatgtagg cggtgctaca gagttcttga agtggtggcc   9780
taactacggc tacactagaa ggacagtatt tggtatctgc gctctgctga agccagttac   9840
cttcggaaaa agagttggta gctcttgatc cggcaaacaa accaccgctg gtagcggtgg   9900
tttttttgtt tgcaagcagc agattacgcg cagaaaaaaa ggatctcaag aagatccttt   9960
gatcttttct acggggtctg acgctcagtg gaacgaaaac tcacgttaag ggattttggt   10020
catgagatta tcaaaaagga tcttcaccta gatcctttta aattaaaaat gaagttttaa   10080
atcaatctaa agtatatatg agtaaacttg gtctgacagt taccaatgct taatcagtga   10140
ggcacctatc tcagcgatct gtctatttcg ttcatccata gttgcctgac tccccgtcgt   10200
gtagataact acgatacggg agggcttacc atctggcccc agtgctgcaa tgataccgcg   10260
agacccacgc tcaccggctc cagatttatc agcaataaac cagccagccg gaagggccga   10320
gcgcagaagt ggtcctgcaa ctttatccgc ctccatccag tctattaatt gttgccggga   10380
agctagagta agtagttcgc cagttaatag tttgcgcaac gttgttgcca ttgctacagg   10440
catcgtggtg tcacgctcgt cgtttggtat ggcttcattc agctccggtt cccaacgatc   10500
aaggcgagtt acatgatccc ccatgttgtg caaaaaagcg gttagctcct tcggtcctcc   10560
gatcgttgtc agaagtaagt tggccgcagt gttatcactc atggttatgg cagcactgca   10620
taattctctt actgtcatgc catccgtaag atgcttttct gtgactggtg agtactcaac   10680
caagtcattc tgagaatagt gtatgcggcg accgagttgc tcttgcccgg cgtcaatacg   10740
ggataatacc gcgccacata gcagaacttt aaaagtgctc atcattggaa aacgttcttc   10800
ggggcgaaaa ctctcaagga tcttaccgct gttgagatcc agttcgatgt aacccactcg   10860
tgcacccaac tgatcttcag catctttac tttcaccagc gtttctgggt gagcaaaaac    10920
aggaaggcaa aatgccgcaa aaaagggaat aagggcgaca cggaaatgtt gaatactcat   10980
actcttcctt tttcaatatt attgaagcat ttatcagggt tattgtctca tgagcggata   11040
catatttgaa tgtatttaga aaaataaaca aataggggtt ccgcgcacat ttccccgaaa   11100
agtgccacct gacgtctaag aaaccattat tatcatgaca ttaacctata aaaataggcg   11160
tatcacgagg ccctttcgtc                                              11180
```

```
SEQ ID NO: 46          moltype = DNA   length = 11108
FEATURE                Location/Qualifiers
misc_feature           1..11108
                       note = pBOL118
source                 1..11108
                       mol_type = other DNA
                       organism = synthetic construct
SEQUENCE: 46
tcgcgcgttt cggtgatgac ggtgaaaacc tctgacacat gcagctcccg gagacggtca   60
cagcttgtct gtaagcggat gccgggagca gacaagcccg tcaggcgcg tcagcggggtg   120
ttggcgggtg tcggggctgg cttaactatg cggcatcaga gcagattgta ctgagagtgc   180
accataccac agcttttcaa ttcaattcat cattttttt ttattctttt ttttgatttc     240
ggtttctttg aaattttttt gattcggtaa tctccgaaca gaaggaagaa cgaaggaagg   300
agcacagact tagattggta tatatacgca tatgtagtgt tgaagaaaca tgaaattgcc   360
cagtattctt aacccaactg cacagaacaa aaacctgcag gaaacgaaga taaatcatgt   420
cgaaagctac atataaggaa cgtgctgcta ctcatcctag tcctgttgct gccaagctat   480
ttaatatcat gcacgaaaag caaacaaact tgtgtgcttc attggatgtt cgtaccacca   540
aggaattact ggagttagtt gaagcattag gtcccaaaat ttgtttacta aaaacacatg   600
tggatatctt gactgatttt tccatggagg gcacagttaa gccgctaaag gcattatccg   660
ccaagtacaa ttttttactc ttcgaagaca gaaaatttgc tgacattggt aatacagtca   720
aattgcagta ctctgcgggt gtatacagaa tagcagaatg ggcagacatt acgaatgcac   780
acggtgtggt gggcccaggt attgttagcg gtttgaagca ggcggcagaa gaagtaacaa   840
aggaacctag aggcctttg atgttagcag aattgtcatg caagggctcc ctatctactg   900
gagaatatac taagggtact gttgacattg cgaagagcga caaagatttt gttatcggct   960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag acattatt gcaaagggaa    1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattaccta tgcggtgtga aataccgcac    1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
```

-continued

```
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gtttttcccag tcacgacgtt gtaaaacgac ggccagtgag cgcgcgtaat   1980
acgactcact ataggcgaa ttgggtaccg ggccccccct cgaggtcgac ggtatcgata   2040
agcttgatat cgaattcctg cagcccgggg gatccactag ttctagagcg gcccatttaa   2100
acggccggcc ctagatcaga gggtggtaaa tgaagtgtaa tagtattcat ttttcttata   2160
aatcatccct tccgtgattt atacaaaaga agaggagaat atgctgaata cttggtatat   2220
tactctacat tatactctta tcttgacggg tattctgagc atcttactca gtttcaagat   2280
cttttaatgt ccaaaaacat ttgagccgat ctaaatactt ctgtgttttc attaatttat   2340
aaattgtact cttttaagac atggaaagta ccaacatcgg ttgaaacagt ttttcattta   2400
cttatggttt attggttttt ccagtgaatg attatttgtc gttaccctt cgtaaaagtt   2460
caaacacgtt tttaagtatt gtttagttgc tctttcgaca tatatgatta tccctgcgcg   2520
gctaaagtta aggatgcaaa aaacataaga caactgaagt taatttacgt caattaagtt   2580
ttccaggta atgatgtttt gggcttccac taattcaata agtatgtcat gaaatacgtt   2640
gtgaagagca tccagaaata atgaaaagaa acaacgaaac tgggtcggcc tgttgtttct   2700
tttctttacc acgtgatctg cggcatttac aggaagtcgc ggtttttgcg cagttgttgc   2760
aacgcagcta cggctaacaa agccagtgg aactcgactg atgtgttagg gcctaaaact   2820
ggtggtgaca gctgaagtga actattcaat ccaatcatgt catggctgtc acaaagacct   2880
tgcggaccgc acgtacgaac acatacgtat gctaatatgt gttttgatag tacccagtga   2940
tcgcagacct gcaattttt tgtaggtttg gaagaatata taaaggttgc actcattcaa   3000
gatagttttt ttcttgtgtg tctattcatt ttattattgt ttgtttaaat gttaaaaaaa   3060
ccaagaactt agtttcaaat taaattcatc acacaaacaa acaaaacaaa atgaacattg   3120
ttgtttgttt gaagcaagtt ccagacactg ctgaagtcag aattgaccca gtcaagggta   3180
ctttaatcag agaaggtgtt ccatctatca tcaacccaga cgacaagaac gctttggaag   3240
aagctttggt tttgaaggac aactacggtg ctcacgttac cgtcatttcc atgggtccac   3300
ctcaagccaa gaacgctttg gttgaagctt tggccatggg tgctgatgaa gctgtcttat   3360
tgactgacag agctttcggt ggtgctgata cttttagctac ctctcacacc attgctgctg   3420
gtatcaagaa attgaaatac gatatcgtct ttgccggtcg tcaagccatc gatggtgata   3480
ccgctcaagt cggtccagaa attgctgaac atttgggtat tccacaagtc acctacgttg   3540
aaaaggttga agttgacggt gacactttga agatcagaaa ggctcgggaa gacggttacg   3600
aagttgttga agtcaagact ccagttctat tgactgccat caaggaattg aacgttccaa   3660
gatacatgtc cgttgaaaag atcttcggtg cttttcgaca ggaagtcaag atgtggactg   3720
ctgatgtat cgatgtcgac aaggccaact tgggtttgaa aggttctcca accaaggtca   3780
agaaatcttc taccaaggaa gtcaagggtc aaggtgaagt cattgacaaa ccagtcaagg   3840
aagctgccgc ttacgttgtt tccaagttga aggaagaaca ctacatctaa agcccggggcg   3900
gagattgata agacttttct agttgcatat cttttatatt taaatcttat ctattagtta   3960
attttttgta atttatcctt aaatatagtc tggttattct aaaatatcat ttcagtatct   4020
aaaaattccc ctctttttc agttatatct taacaggcga cagtccaaat gttgatttat   4080
cccagtccga ttcatcaggg ttgtgaagca ttttgtcaat ggtcgaaatc acatcagtaa   4140
tagtgcctct tacttgcctc atagaatttc tttctcttaa cgtcaccgtt tggtcttta   4200
tagtttcgaa atctatggtg ataccaaatg gtgttcccaa ttcatcgtta cgggcgtatt   4260
ttttaccaat tgaagtattg gaatcgtcaa ttttaaagta tatctctctt ttacgtaaag   4320
cctgcgagat cctcttaagt atagcgggga agccatcgtt attcgatatt gtcgtaacaa   4380
atactttgat cggcgctatg tttaaatgtt taaacatgga cagatatgcg atgaaaacgc   4440
taagtgatac tccaaatggt gaaaggtacg atgcttggaa acaatacttg gaaatcaccg   4500
gaaacaccat atgcggcgaa aagccaatta gtgtgatact aagtgcttta tcgaaaatcc   4560
gtgatgccgg tccttcaggc atcaaatttc agtggcctaa ttattcacag agttctcatg   4620
tgacaagtat tgatgatagt agtgtcagtt atgcttcagg ttatgttact ataggataat   4680
gatcacggct aaaacggtcg aatgtaagca tatatctttc gattgtataa ttgttcccaa   4740
atactacagc atctcaagga aaaaaaaaca aaaacttcca aaaaaatcga atccctgagg   4800
aatctttaat acattttcaa tctatttaag ttttataaac gtgtatatga gatgtcatga   4860
gcatgaatta ttaataataa aaactaaatc attaaagtaa cttaaggagt taaagcccgg   4920
gctttaattg ttagcagcct tgacttgagc aatcaattct ggaacaacct tgttgacatc   4980
accgacaatg gccaaatcag caaccttcat gattggagct tcgacatctt tgttgatggc   5040
aatgatgtag tcagagtctt gcataccagc caagtgttgg atggcaccag agataccaca   5100
agcaatgtac aaagttggtc tgacggtctt accggtttga ccgacttgca gtccttgtc   5160
aacccattcc ttttcaatgg cagctctgga agcagcaatg gtaccaccca acaaagaagc   5220
taattcttcc aatttttcga agttttcctt ggaaccaaca ccacgaccac cagcaaccaa   5280
aaccttggct tcaccgatat cagcaatgtc cttggccaat ttgacaacct tggaaacctt   5340
ggttctgata tcagaagcag tcaatttgat ggcaacctt tcgatcttgt catcagaaac   5400
gttagcatcg ttaactggca atttttcaaa gacacctggt ctgacggtgg ccatttgagg   5460
tctgtggtca gaacagacaa tggtagcaat caagttacca ccgaaagctg gtctggtagc   5520
caacaagtca cggttttcga catcgatatc caaagaggta cagtcgacag tcaaaccagt   5580
agacaatctg gcagcaattc ttggacccaa gtctctaccg atgaaagtag caccgatgaa   5640
taagatttct ggctttcttt cgttgaccaa gtcacagata accttggcgt aaccgtcagt   5700
ggagaaatga gctaataatt cgttgtcagc agccaaaacc ttgtcagcac cgtgggacaa   5760
caagtccttg gacatctttt cagtgttgtg acccaataag acagcagtca attcaacacc   5820
caattttca gccatttcct taccctacc tagcaattcc aaagaaacct tttgtaattc   5880
accatctctt tgttcagcga aaacccagac acccttgtag tcagccttgt tcatgtttag   5940
ttaattatag ttcgttgacc gtatattcta aaaacaagta ctccttaaaa aaaaaccttg   6000
aagggaataa acaagtagaa tagatagaga gaaaaataga aaatgcaaga gaatttatat   6060
attagaaaga gagaaagaaa aatggaaaaa aaaaatagg aaaagccaga aatagcacta   6120
gaaggagcga caccagaaaa gaaggtgatg gaaccaattt agctatatat agttaactac   6180
```

-continued

```
cggctcgatc atctctgcct ccagcatagt cgaagaagaa ttttttttt cttgaggctt   6240
ctgtcagcaa ctcgtatttt ttctttcttt tttggtgagc ctaaaaagtt cccacgttct   6300
cttgtacgac gccgtcacaa acaaccttat gggtaatttg tcgcggtctg ggtgtataaa   6360
tgtgtgggtg caggccggcc gtttaaacgg gccgccaccg cggtggagcc tgtgtggaag   6420
aacgattaca acaggtgttg tcctctgagg acataaaata cacaccgaga ttcatcaact   6480
cattgctgga gttagcatat ctacaattgg gtgaaatggg gagcgatttg caggcatttg   6540
ctcggcatgc cggtagaggt gtggtcaata agagcgacct catgctatac ctgagaaagc   6600
aacctgacct acaggaaaga gttactcaag aataagaatt ttcgttttaa aacctaagag   6660
tcactttaaa atttgtatac acttattttt tttataactt atttaataat aaaaatcata   6720
aatcataaga aattcgctcg agtcgactgc agtttaaaca attctgaaag catcgaccaa   6780
aacacaacga cgtaatctga cgaaagttct ggcagaagtg acaccttcac cagttggggt   6840
ggtgatggtc atggtggtcc aaccttcacc acccaaaccc aaaccagcga tacatggacc   6900
gttcttgaca aagatggaag tgtcaatggc gttagccatt tggttcatgt tttcgatgtt   6960
tctggagtgc atggcagcag tgtggtgaca accaccttcc aatttgacag ccaaagcaat   7020
agcgtcagca acgttagcaa cacggacaac tggtaagact ggcatcatca attcagtgac   7080
agcaaatggg tgttcagcgg tggtttcgac gaataataat ctggtttctt gtggaacctt   7140
caaaccgatg gcagcagcaa tcttaccagc atctctacca acccagtctc tggagacggt   7200
acccttacct ctttcatcga tgttcttcaa caaaactggt tgcaattgtt gagcttgttc   7260
agcagtcaac ttgacggcat gttgaccttc catcaatctc atcaattcgt cagcaacgga   7320
gtcaacaaca atcaaaacct tttcgtcagc acagatgatg ttgttgtcga aagaagcacc   7380
cttgacaatg gattgagcag ctctggccaa atcagcggtt tcatcgacaa caacaggagg   7440
gttaccagca ccagcagcaa tcaatctctt gttggtgtgc tttctggcag cttcaacaac   7500
agcttcacca ccagtgacga ctaatagacc gatacctggg aacttgaata atctttgagc   7560
agtttcgata tctgggttgg caacagtgac caacaagttt tctggaccac cagcagcaac   7620
aatggcttgg ttcaatagag tgatggctct ttgagaaacc ttcttggcag ctgggtgtgg   7680
agcgaaagata acggagttac cagcagcaat caaagagagt gcgttgttga tgacagtagc   7740
agctgggttg gtagatgggg tgacggaagc aacaacaccc catggagcat tttcaatcaa   7800
agtcaaacca ttatcaccgg tcaagacttg tggagacaaa cattcgacac ctggagtacc   7860
tctagcttga gcaacgttct tagcgaattt gtcttcaact ctacccatac cggtttcgga   7920
gacagccaat tcagccaagt ctctggcatg cttttcacca gcttctctga tggcagcaat   7980
ggccaattgt ctcatggcaa cagatttcaa accttgttga gcaaccttgg cagcagcaac   8040
agcgtcgtcc aaagaagcga aaacacccat ttcgtggaca gcagcagatg gagtgtcaga   8100
agattgcatt ttcaacaaga cagccttgac aacttgttcg atatcttgtt ggttcatttt   8160
ttactagttc tagaatccgt cgaaactaag ttctggtgtt ttaaaactaa aaaaaagact   8220
aactataaaa gtagaattta agaagtttaa gaaatagatt tacagaatta caatcaatac   8280
ctaccgtctt tatatactta ttagtcaagt aggggaataa tttcagggaa ctggtttcaa   8340
cctttttttt cagctttttc caaatcagag agagcagaag gtaatagaag gtgtaagaaa   8400
atgagataga tacatgcgtg ggtcaattgc cttgtgtcat catttactcc aggcaggttg   8460
catcactcca ttgaggttgt gcccgttttt tgcctgtttg tgcccctgtt ctctgtagtt   8520
gcgctaagag aatggaccta tgaactgatg gttggtgaag aaaacaatat tttggtgctg   8580
ggattctttt ttttttctgga tgccagctta aaaagcgggc tccattatat ttagtggatg   8640
ccaggaataa actgttcacc cagacaccta cgatgttata tattctgtgt aacccgcccc   8700
ctatttttggg catgtacggg ttacagcaga attaaaaggc taattttttg actaaataaa   8760
gttaggaaaa tcactactat taattattta cgtattcttt gaaatggcga gtattgataa   8820
tgataaactg agctccagct tttgttccct ttagtgaggg ttaattgcgc gcttggcgta   8880
atcatggtca tagctgtttc ctgtgtgaaa ttgttatccg ctcacaattc cacacaacat   8940
aggagccgga agcataaagt gtaaagcctg gggtgcctaa tgagtgaggt aactcacatt   9000
aattgcgttg cgctcactgc cgctttccca gtcgggaaac ctgtcgtgcc agctgcatta   9060
atgaatcggc caacgcgcgg ggagaggcgg tttgcgtatt gggcgctctt ccgcttcctc   9120
gctcactgac tcgctgcgct cggtcgttcg gctgcggcga cggtatcag ctcactcaaa   9180
ggcggtaata cggttatcca cagaatcagg ggataacgca ggaaagaaca tgtgagcaaa   9240
aggccagcaa aaggccagga accgtaaaaa ggccgcgttg ctggcgtttt tccataggct   9300
ccgcccccct gacgagcatc acaaaaatcg acgctcaagt cagaggtggc gaaacccgac   9360
aggactataa agataccagg cgtttccccc tggaagctcc ctcgtgcgct ctcctgttcc   9420
gaccctgccg cttaccggat acctgtccgc ctttctccct tcgggaagcg tggcgctttc   9480
tcatagctca cgctgtaggt atctcagttc ggtgtaggtc gttcgctcca agctgggctg   9540
tgtgcacgaa ccccccgttc agcccgaccg ctgcgcctta tccggtaact atcgtcttga   9600
gtccaacccg gtaagacacg acttatcgcc actggcagca gccactggta acaggattag   9660
cagagcgagg tatgtaggcg gtgctacaga gttcttgaag tggtggccta actacggcta   9720
cactagaagg acagtatttg gtatctgcgc tctgctgaag ccagttacct tcggaaaaag   9780
agttggtagc tcttgatccg gcaaacaaac caccgctggt agcggtggtt tttttgtttg   9840
caagcagcag attacgcgca gaaaaaaagg atctcaagaa gatcctttga tcttttctac   9900
ggggtctgac gctcagtgga acgaaaactc acgttaaggg attttggtca tgagattatc   9960
aaaaaggatc ttcacctaga tccttttaaa ttaaaaatga agttttaaat caatctaaag   10020
tatatatgag taaacttggt ctgacagtta ccaatgctta atcagtgagg cacctatctc   10080
agcgatctgt ctatttcgtt catccatagt tgcctgactc cccgtcgtgt agataactac   10140
gatacgggag ggcttaccat ctggccccag tgctgcaatg ataccgcgag acccacgctc   10200
accggctcca gatttatcag caataaacca gccagccgga agggccgagc gcagaagtgg   10260
tcctgcaact ttatccgcct ccatccagtc tattaattgt tgccgggaag ctagagtaag   10320
tagttcgcca gttaatagtt tgcgcaacgt tgttgccatt gctacaggca tcgtggtgtc   10380
acgctcgtcg tttggtatgg cttcattcag ctccggttcc caacgatcaa ggcgagttac   10440
atgatccccc atgttgtgca aaaaagcggt tagctccttc ggtcctccga tcgttgtcag   10500
aagtaagttg gccgcagtgt tatcactcat ggttatggca gcactgcata attctcttac   10560
tgtcatgcca tccgtaagat gcttttctgt gactggtgag tactcaacca agtcattctg   10620
agaatagtgt atgcggcgac cgagttgctc ttgcccggcg tcaatacggg ataataccgc   10680
gccacatagc agaactttaa aagtgctcat cattggaaaa cgttcttcgg ggcgaaaact   10740
ctcaaggatc ttaccgctgt tgagatccag ttcgatgtaa cccactcgtg cacccaactg   10800
atcttcagca tcttttactt tcaccagcgt ttctgggtga gcaaaaacag gaaggcaaaa   10860
tgccgcaaaa aagggaataa gggcgacacg gaaatgttga atactcatac tcttcctttt   10920
```

```
tcaatattat tgaagcattt atcagggtta ttgtctcatg agcggataca tatttgaatg   10980
tatttagaaa aataaacaaa taggggttcc gcgcacattt ccccgaaaag tgccacctga   11040
cgtctaagaa accattatta tcatgacatt aacctataaa aataggcgta tcacgaggcc   11100
ctttcgtc                                                             11108
```

```
SEQ ID NO: 47              moltype = DNA   length = 11114
FEATURE                    Location/Qualifiers
misc_feature               1..11114
                           note = pBOL120
source                     1..11114
                           mol_type = other DNA
                           organism = synthetic construct
SEQUENCE: 47
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accataccac agcttttcaa ttcaattcat catttttttt ttattctttt ttttgatttc   240
ggtttctttg aaattttttt gattcggtaa tctccgaaca gaaggaagaa cgaaggaagg   300
agcacagact tagattggta tatatacgca tatgtagtgt tgaagaaaca tgaaattgcc   360
cagtattctt aacccaactg cacagaacaa aaacctgcag gaaacgaaga taaatcatgt   420
cgaaagctac atataaggaa cgtgctgcta ctcatcctag tcctgttgct gccaagctat   480
ttaatatcat gcacgaaaag caaacaaact tgtgtgcttc attggatgtt cgtaccacca   540
aggaattact ggagttagtt gaagcattag gtcccaaaat ttgtttacta aaaacacatg   600
tggatatctt gactgatttt tccatggagg gcacagttaa gccgctaaag gcattatccg   660
ccaagtacaa ttttttactc ttcgaagaca gaaaatttgc tgacattggt aatacagtca   720
aattgcagta ctctgcgggt gtatacagaa tagcagaagg ggcagacatt acgaatgcac   780
acggtgtggt gggcccaggt attgttagcg gtttgaagca ggcggcagaa gaagtaacaa   840
aggaacctag aggccttttg atgttagcag aattgtcatg caagggctcc ctatctactg   900
gagaaatata taagggtact gttgacattg cgaagagcga caaagatttt gttatcggct   960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcat   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg cgctggcaa    1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact ataggggcgaa ttgggtaccg ggccccccct cgaggtcgat ggtatcgata   2040
agcttgatat cgaattcctg cagcccgggg gatccactag ttctagagcg gcccatttaa   2100
acggccggcc ctagatcaga gggtggtaaa tgaagtgtaa tagtattcat ttttcttata   2160
aatcatccct tccgtgattt atacaaaaga agaggagaat atgctgaata cttggtatat   2220
tactctacat tatactctta tcttgacggg tattctgagc atcttactca gttttcaagat   2280
cttttaatgt ccaaaaacat ttgagccgat ctaaatactt ctgtgttttc attaatttat   2340
aaattgtact cttttaagac atggaaagta ccaacatcgg ttgaaacagt ttttcattta   2400
cttatggttt attggttttt ccagtgaatg attatttgtc gttacccttt cgtaaaagtt   2460
caaacacgtt tttaagtatt gtttagttgc tctttcgaca tatatgatta tccctgcgcg   2520
gctaaagtta aggatgcaaa aaacataaga caactgaagt taatttacgt caattaagtt   2580
ttccagggta atgatgtttt gggcttccac taattcaata agtatgtcat gaaatacgtt   2640
gtgaagagca tccagaaata atgaaaagaa acaacgaaac tgggtcggcc tgttgtttct   2700
tttctttacc acgtgatctg cggcatttac aggaagtcgc gcgtttttag cagttgttgc   2760
aacgcagcta cggctaacaa agcctagtgg aactcgactg atgtgttagg gcctaaaact   2820
ggtggtgaca gctgaagtga actattcaat ccaatcatgt catggctgtc acaaagacct   2880
tgcggaccgc acgtacgaac acatacgtat gctaatatgt gtttttgatag tacccagtga   2940
tcgcagacct gcaatttttt tgtaggtttg gaagaatata taaaggttgc actcattcaa   3000
gatagttttt ttcttgtgtg tctattcatt ttattattgt ttgttttaaat gttaaaaaaa   3060
ccaagaactt agtttcaaat taaattcatc acacaaacaa acaaaacaaa atgaacattg   3120
ttgtttgttt gaagcaagtt ccagacactg ctgaagtcag aattgaccca gtcaagggta   3180
ctttaatcag agaaggtgtt ccatctatca tcaacccaga cgacaagaac gctttggaag   3240
aagctttggt tttgaaggac aactacggtg ctccacgttc cgtcatttcc atgggtccac   3300
ctcaagccaa gaacgctttg gttgaagctt tggccatggg tgctgaa gctgtcttat       3360
tgactgacag agcttttcggt ggtgctgata cttttagctac ctctcacacc attgctgctg  3420
gtatcaagaa attgaaatac gatatcgtct ttgccggtcg tcaagccatc gatggtgata   3480
ccgctcaagt cggtccagaa attgctgaac atttgggtat tccacaagtc acctacgttg   3540
aaaaggttga agttgacggt gacactttga agatcagaaa ggcttgggaa gacggttacg   3600
aagttgttga agtcaagact ccagttctat tgactgccat caaggaattg aacgttccaa   3660
gatacatgtc cgttgaaaag atcttcggtg ctttcgacaa ggaagtcaag atgtggactg   3720
ctgatgatat cgatgtcgac aaggccaact gggtttgaa aggttctcca accaaggtca    3780
agaaatcttc taccaaggaa gtcaagggtc aaggtgaagt cattgacaaa ccagtcaagg   3840
aagctgccgt tacgttgtt tccaagttga aggaagaaca ctacatctaa agcccgggcg    3900
gagattgata agacttttct agttgcatat cttttatatt taaatcttat ctattagtta   3960
```

```
atttttgta atttatcctt atatatagtc tggttattct aaaatatcat ttcagtatct 4020
aaaaattccc ctcttttttc agttatatct taacaggcga cagtccaaat gttgatttat 4080
cccagtccga ttcatcaggg ttgtgaagca ttttgtcaat ggtcgaaatc acatcagtaa 4140
tagtgcctct tacttgcctc atagaatttc tttctcttaa cgtcaccgtt tggtctttta 4200
tagtttcgaa atctatggtg ataccaaatg gtgttcccaa ttcatcgtta cgggcgtatt 4260
ttttaccaat tgaagtattg gaatcgtcaa ttttaaagta tatctctctt ttacgtaaag 4320
cctgcgagat cctcttaagt atagcgggga agccatcgtt attcgatatt gtcgtaacaa 4380
atactttgat cggcgctatg tttaaatgtt taaacatgga cagatatgcg atgaaaacgc 4440
taagtgatac tccaaatggt gaaaggtacg atgcttggaa acaatacttg gaaatcaccg 4500
gaaacaccat atgcggcgaa aagccaatta gtgtgatact aagtgcttta tcgaaaatcc 4560
gtgatgccgg tccttcaggc atcaaatttc agtggcctaa ttattcacag agttctcatg 4620
tgacaagtat tgatgatagt agtgtcagtt atgcttcagg ttatgttact ataggataat 4680
gatcacggct aaaacggtcg aatgtaagca tatatctttc gattgtataa ttgttcccaa 4740
atactacagc atctcaagga aaaaaaaaca aaaacttcca aaaaaatcga atccctgagg 4800
aatctttaat acatttttcaa tctatttaag ttttataaac gtgtatatga gatgtcatga 4860
gcatgaatta ttaataataa aaactaaatc attaaagtaa cttaaggagt taaagcccgg 4920
gctttaattg ttagcagcct tgacttgagc aatcaattct ggaacaacct tgttgacatc 4980
accgacaatg gccaaatcag caaccttcat gattggagct tcgacatctt tgttgatggc 5040
aatgatgtag tcagagtctt gcataccagc caagtgttgg atggcaccag agataccaca 5100
agcaatgtac aaagttggtc tgacggtctt accggtttga ccgacttgca agtccttgtc 5160
aacccattcc ttttcaatgg cagctctgga agcagcaatg gtaccaccca acaaagaagc 5220
taattcttcc aattttttcga agtttttcctt ggaaccaaca ccacgaccac cagcaaccaa 5280
aaccttggct tcaccgatat cagcaatgtc cttggccaat ttgacaacct tggaaacctt 5340
ggttctgata tcagaagcag tcaatttgat ggcaaccttt tcgatcttgt catcagaaac 5400
gttagcatcg ttaactggca attttttcaaa gacacctggt ctgacggtgg ccatttgagg 5460
tctgtggtca gaacagacaa tggtagcaat caagttacca ccgaaagctg gtctggtagc 5520
caacaagtca cggttttcga catcgatatc caaagaggta cagtcagcag tcaaaccagt 5580
agacaatctg gcagcaattc ttggacccaa gtctctaccg atgaaagtag caccgatgaa 5640
taagatttct ggctttcttt cgttgaccaa gtcacagata accttggcgt aaccgtcagt 5700
ggagaaatga gctaataatt cgttgtcagc agccaaaacc ttgtcagcac cgtgggacaa 5760
caagtccttg gacatctttt cagtgttgtg acccaataag acagcagtca attcaacacc 5820
caattttttca gccatttcct taccctttacc tagcaattcc aaagaaacct tttgtaattc 5880
accatctctt tgttcagcga aaacccagac acccttgtag tcagccttgt tcatgtttag 5940
ttaattatag ttcgttgacc gtatattcta aaaacaagta ctccttaaaa aaaaaccttg 6000
aagggaataa acaagtagaa tagatagaga gaaaaataga aaatgcaaga gaatttatat 6060
attagaaaga gagaaagaaa aatggaaaaa aaaaaatagg aaaagccaga aatagcacta 6120
gaaggagcga caccagaaaa gaaggtgatg gaaccaattt agctatatat agttaactac 6180
cggctcgatc atctctgcct ccagcatagt cgaagaagaa ttttttttttt cttgaggctt 6240
ctgtcagcaa ctcgtatttt ttctttcttt tttggtgagc ctaaaaagtt cccacgttct 6300
cttgtacgac gccgtcacaa acaaccttat gggtaatttg tcgcggtctg ggtgtataaa 6360
tgtgtgggtg caggccggcc gtttaaacgg gccgccaccg cggtggagcc tgtgtggaag 6420
aacgattaca acaggtgttg tcctctgagg acataaaata cacaccgaga ttcatcaact 6480
cattgctgga gttagcatat ctacaattgg gtgaaatggg gacgcatttg caggcatttg 6540
ctcggcatgc cggtagaggt gtggtcaata agagcgacct catgctatac ctgagaaagc 6600
aacctgacct acaggaaaga gttactcaag aataagaatt ttcgtttttaa aacctaagag 6660
tcactttaaa atttgtatac acttattttt tttataactt atttaataat aaaaatcata 6720
aatcataaga aattcgctcg agtcgactgc agtttatcta ggagaaaac catcagtcaa 6780
gacacatctt cttcttctag cgaagtgacg ggcagtggta gtaccttcac cagttggagt 6840
agcaatggta aaagtggtgg aaccttcacc tctgaaacct aaaccagcga aagatggacc 6900
gttcttgaca aagatggagg tttgcatgtc acggcagcc ttgttcaatc tggagatgtt 6960
ttgagagtgc atggtagcag tgtgatgtag accttgttcc aattcaatgg caacttccaa 7020
agcttcatcg aagtctggaa ctctgacaac tggaacaatt ggcatcaaca attcaacagt 7080
agcgaatggg tgggactttt cagtttcgac aatgatcaat cttggggtga aatcacaagc 7140
aataccagct tctttcaaga tttcagtggc agacttacca accaatttct tgttggtgac 7200
acccttgtca gtgacggcaa ccttttccaa ttttggata tcagatgggt tagtgacgtg 7260
caaagcaccg ttcttttcca tttggaacaa caagaagtca gcaatggagt caacggcaac 7320
aacagacttt tcagcgatac acaagatatt atggtcaaag gaagcaccgt cgacaatgtc 7380
agcagcagcc ttttcaatgt tagcggtttc gtcaacgatg gatggagggt taccagcacc 7440
agcaccgata accttcttac cagattgcat agcttgcaag acaacacctg gaccaccagt 7500
gatgaccaac aatggaacct ttgggtggtt catcatttct tgagcagctt ggatagatgg 7560
cttggcaacg gtgacaatca agttgtcaat accacaagaa tctctgacga tagtgttcaa 7620
cttttcaatc aaccataaag agatgttctt ggcacctggg tgaggagagt agaaaacggc 7680
gttaccagca gccaacatac cgatggagtt acagatcaaa gtttcagttg ggttggtaga 7740
tggagcaaca gcaccgatga caccgtatgg agataattcg tataaagtca taccgttgtc 7800
accggtagca acttcagtgt acaagtcttc aacacctgga gtcttttcga tagctaaagt 7860
gttcttcaag attttatcgg tgacattacc cataccggtt tcagcaacag ctctggtagc 7920
aatggtttcg atttctgggt ataaagcttc tctgatggcc ttgacaacgt ttcttctttc 7980
ttccaaagat ttttccttgt aacagttttg agcaatgacg gcagcttgga cagcttcatc 8040
gacggtatcg aaaacaccgg acttggcacc ttgggtggtg gtcttggttg gaacttcctt 8100
ttgttcagcc aatttttcca acaaaacctt cttgactaat tgttccaatt ccaaagattc 8160
catttttttac tagttctaga atccgtcgaa actaagttct ggtgtttaa aactaaaaaa 8220
aagactaact ataaaagtag aatttaagaa gtttaagaaa tagatttaca gaattacaat 8280
caatacctac cgtctcttata tacttattag tcaagtaggg gaataaattc agggaactgg 8340
tttcaacctt ttttttcagc tttttccaaa tcagagagg cagaaggtaa tagaaggtgt 8400
aagaaaatga gatagataca tgcgtgggtc aattgccttg tgtcatcatt tactccagcc 8460
aggttgcatc actccattga ggttgtgccg gtttttttgcc tgtttgtgcc cctgttctct 8520
gtagttgcgc taagagaatg gacctatgaa ctgatggttg gtgaagaaaa caatattttg 8580
gtgctgggat tcttttttttt tctggatgcc agcttaaaaa gcgggctcca ttatatttag 8640
tggatgccag gaataaactg ttcacccaga cacctacgat gttatatatt ctgtgtaacc 8700
```

-continued

```
cgcccctat tttgggcatg tacgggttac agcagaatta aaaggctaat tttttgacta  8760
aataaagtta ggaaaatcac tactattaat tatttacgta ttctttgaaa tggcgagtat  8820
tgataatgat aaactgagct ccagcttttg ttccctttag tgagggttaa ttgcgcgctt  8880
ggcgtaatca tggtcatagc tgtttcctgt gtgaaattgt tatccgctca caattccaca  8940
caacatagga gccggaagca taaagtgtaa agcctgggtg gcctaatgag tgaggtaact  9000
cacattaatt gcgttgcgct cactgcccgc tttccagtcg ggaaacctgt cgtgccagct  9060
gcattaatga atcggccaac gcgcggggag aggcggtttg cgtattgggc gctcttccgc  9120
ttcctcgctc actgactcgc tgcgctcggt cgttcggctg cggcgagcgg tatcagctca  9180
ctcaaaggcg gtaatacggt tatccacaga atcaggggat aacgcaggaa agaacatgtg  9240
agcaaaaggc cagcaaaagg ccaggaaccg taaaaaggcc gcgttgctgg cgtttttcca  9300
taggctccgc ccccctgacg agcatcacaa aaatcgacgc tcaagtcaga ggtggcgaaa  9360
cccgacagga ctataaagat accaggcgtt cccccctgga agctccctcg tgcgctctcc  9420
tgttccgacc ctgccgctta ccggatacct gtccgccttt ctcccttcgg gaagcgtggc  9480
gctttctcat agctcacgct gtaggtatct cagttcggtg taggtcgttc gctccaagct  9540
gggctgtgtg cacgaacccc ccgttcagcc cgaccgctgc gccttatccg gtaactatcg  9600
tcttgagtcc aacccggtaa gacacgactt atcgccactg gcagcagcca ctggtaacag  9660
gattagcaga gcgaggtatg taggcggtgc tacagagttc ttgaagtggt ggcctaacta  9720
cggctacact agaaggacag tatttggtat ctgcgctctg ctgaagccag ttaccttcgg  9780
aaaaagagtt ggtagctctt gatccggcaa acaaaccacc gctggtagcg gtggtttttt  9840
tgtttgcaag cagcagatta cgcgcagaaa aaaaggatct caagaagatc ctttgatctt  9900
ttctacgggg tctgacgctc agtggaacga aaactcacgt taagggattt tggtcatgag  9960
attatcaaaa aggatcttca cctagatcct tttaaattaa aaatgaagtt ttaaatcaat 10020
ctaaagtata tatgagtaaa cttggtctga cagttaccaa tgcttaatca gtgaggcacc 10080
tatctcagcg atctgtctat ttcgttcatc catagttgcc tgactccccg tcgtgtagat 10140
aactacgata cgggagggct taccatctgg ccccagtgct gcaatgatac cgcgagaccc 10200
acgctcaccg gctccagatt tatcagcaat aaaccagcca gccggaaggg ccgagcgcag 10260
aagtggtcct gcaactttat ccgcctccat ccagtctatt aattgttgcc gggaagctag 10320
agtaagtagt tcgccagtta atagtttgcg caacgttgtt gccattgcta caggcatcgt 10380
ggtgtcacgc tcgtcgtttg gtatggcttc attcagctcc ggttcccaac gatcaaggcg 10440
agttacatga tcccccatgt tgtgcaaaaa agcggttagc tccttcggtc ctccgatcgt 10500
tgtcagaagt aagttggccg cagtgttatc actcatggtt atggcagcac tgcataattc 10560
tcttactgtc atgccatccg taagatgctt ttctgtgact ggtgagtact caaccaagtc 10620
attctgagaa tagtgtatgc ggcgaccgag ttgctcttgc ccggcgtcaa tacgggataa 10680
taccgcgcca catagcagaa ctttaaaagt gctcatcatt ggaaaacgtt cttcggggcg 10740
aaaactctca aggatcttac cgctgttgag atccagttcg atgtaaccca ctcgtgcacc 10800
caactgatct tcagcatctt ttactttcac cagcgtttct gggtgagcaa aaacaggaag 10860
gcaaaatgcc gcaaaaaagg gaataagggc gacacggaaa tgttgaatac tcatactctt 10920
cctttttcaa tattattgaa gcatttatca gggttattgt ctcatgagcg gatacatatt 10980
tgaatgtatt tagaaaaata aacaaatagg ggttccgcgc acatttcccc gaaaagtgcc 11040
acctgacgtc taagaaacca ttattatcat gacattaacc tataaaaata ggcgtatcac 11100
gaggcccttt cgtc                                                    11114
```

```
SEQ ID NO: 48          moltype = DNA   length = 2613
FEATURE                Location/Qualifiers
source                 1..2613
                       mol_type = other DNA
                       organism = Entamoeba histolytica
SEQUENCE: 48
atgtcaacac aacaaactat gactgtagat gaacatatta atcaacttgt tgctaaagca   60
caagttgcac ttaaagaata tcttaaacca gaatatacac aagaaaaaat agattatatt  120
gtaaagaaag catcagttgc agcacttgat caacattgtg cacttgcagc agctgcagtt  180
gaagaaacag gaagaggtat ttttgaagat aaagctacta aaaatatatt tgcatgtgaa  240
catgttacac atgaaatgag acatgctaaa acagttggta ttattaatgt agatccactt  300
tatggaatta cagaaattgc agaaccagtt ggagttgttt gtggagttac accagttact  360
aatccaacat caacagctat tttcaagtca cttatttcaa ttaaaacaag aaatccaatt  420
gtattttcat tccatccatc agcacttaaa tgttctatta tggcagctaa aattgttaga  480
gatgcagcta ttgcagcagg agcaccagaa aattgtattc aatggattga atttggagga  540
attgaagcat caaataaatt aatgaatcat ccaggagttg ctactattct tgctacagga  600
ggaaatgcta tggttaaagc agcatattca tcaggaaaac cagcacttgg agtaggagca  660
ggaaatgtac caacatatat tgaaaaaaca tgtaatatta aacaagcagc aaatgatgta  720
gttatgtcaa aatcatttga taatggtatg atttgtgcat cagaacaagc agcaattatt  780
gataaagaaa tttatgatca agtagttgaa gaaatgaaaa cacttggagc atatttcatt  840
aatgaagaag aaaaagctaa attagaaaag tttatgtttg gagttaatgc atattcagca  900
gatgttaata atgcaagact taatccaaaa tgtccaagat gtcaccacca atggtttgct  960
gaacaagttg gaattaaagt tccagaagat tgtaatatta tttgtgcagt tgtaaagaa  1020
gttggaccaa atgaaccatt aacaagagaa aaattatcac cagttcttgc tattcttaaa  1080
gcagaaaata cacaagatgg tattgataaa gctgaagcta tggttgaatt taatggtaga  1140
ggacattcag cagctattca ttcgaatgat aaagcagtag ttgaaaagta tgcacttaca  1200
atgaaagcat gcagaatttt acataataca ccatcatcac aaggaggaat tggatcaatt  1260
tataactata tttggccatc atttacactt ggatgtggat catatggagg aaattcggta  1320
tcagctaatg ttacatatca taatttatta aatattaaaa gacttgcaga tagaagaaac  1380
aaccttcaat ggttcagagt tccaccaaag attttctttg aaccacattc tattagatat  1440
cttgctgaac ttaaggaact tagtaaaata ttcattgttt cagatagaat gatgtataaa  1500
ttaggatatg tagatagagt tatggatgta ttgaaaagaa gaagtaatga agtagaaatt  1560
gaaattttca ttgatgtaga accagatcca tctattcaaa ccgttcaaaa aggacttgct  1620
gttatgaata catttggacc agataatatt attgctattg gaggaggatc agctatggat  1680
gcagctaaga ttatgtggtt actttatgaa catccagaag ccgatttctt tgcaatgaaa  1740
caaaaattca ttgatcttag aaagagagca tttaaattcc caacaatggg taagaaagct  1800
agattaattt gtattccaac aacatcagga actggatcag aagttacacc atttgcagtt  1860
```

```
atttcagatc atgaaacagg taagaaatat ccacttgctg attattcact tacaccatca  1920
gttgctattg ttgatccaat gtttactatg tcacttccaa agagagctat tgctgatact  1980
ggacttgatg tattggttca tgcaacagaa gcatatgttt cagttatggc taatgaatat  2040
actgatggac ttgctagaga agcagttaaa ttagtctttg aaaatcttct taaatcatat  2100
aatggagatt tagaagcaag agaaaagatg cacaatgctg caacaattgc aggtatggca  2160
tttgcatcag cattccttgg tatggaccat tccatggcac ataaagttgg agcagcattc  2220
catcttccac atggtagatg tgtagcagta ttattaccac atgtcattag atataatgga  2280
caaaaaccaa gaaagcttgc aatgtggcca aaatataatt tctataaggc agaccaaaga  2340
tatatggaac ttgcacaaat ggttggactt aaatgtaata caccagctga aggagttgaa  2400
gcatttgcta aagcatgtga agaattaatg aaagccacag agactattac tggattcaag  2460
caagcaaata ttgatgaagc agcatggatg agtaaagtac cagaaatggc acttcttgca  2520
tttgaagatc aatgttcacc agctaatcca agagtcccaa tggttaagga tatggaaaag  2580
attctcaaag ctgcatatta tccaattgct tga                                2613
```

```
SEQ ID NO: 49          moltype = DNA  length = 2610
FEATURE                Location/Qualifiers
misc_feature           1..2610
                       note = adh2 E. histolytica codon pair optimised
source                 1..2610
                       mol_type = other DNA
                       organism = synthetic construct
SEQUENCE: 49
atgtccactc aacaaaccat gaccgttgat gaacacatta accaattggt cagaaaggct  60
caagttgctt tgaaggaata cttgaaacca gaatacactc aagaaaagat cgattacatt  120
gtcaagaagg cttctgttgc tgctctagac caacactgtg cttggctgc tgctgctgtc  180
gaagaaactg gtcgtggtat ctttgaagac aaagctacca agaacatttt cgcttgtaca  240
cacgtcactc acgaaatgag acacgccaag accgttggta tcatcaacgt tgatccatta  300
tacggtatca ctgaaattgc tgaaccagtc ggtgttgtct gtggtgtcac cccagttacc  360
aacccaactt ctactgccat tttcaaatct ttgatttcca tcaagaccag aaacccaatt  420
gttttctcct tccacccatc tgctttgaaa tgttccatca tggctgcaa gatcgtcaga  480
gatgctgcca ttgctgctgg tgctccagaa aactgtatcc aatggatcga atttggtggt  540
attgaagctt ccaacaaatt gatgaaccat cctggtgttg ctaccatctt agctactggt  600
ggtaacgcta tggtcaaggc tgcttactct tctggtaagc cagcttttgg gtgtcggtgct  660
ggtaacgtcc caacttacat cgaaaagacc tgtaatatca agcaagctgc taacgatgtt  720
gtcatgtcca gtctttcga caacggtatg atctgtgcct ccgaacaagc tgccatcatc  780
gacaaagaaa tctacgacca agttgttgaa gaaatgaaga ctttgggtgc ttacttcatc  840
aacgaagaag aaaaggccaa attggaaaaa ttcatgttcg gtgttaatgc ttactctgct  900
gatgtcaaca acgccagatt gaacccaaag tgtccaggta tgtctccaca atggttcgct  960
gaacaagtcg gtatcaaggt tccagaaggac tgtaacatca tctgtgccgt ttgtaaggaa  1020
gttggtccaa acgaaccatt gaccagagaa aagttgtctc cagttttggc catttttgaag  1080
gctgaaaaca ctcaagatgg tattgacaag gctgaagcta tggtcgaatt caacggtcgt  1140
ggtcactctg ctgccattca ctccaatgac aaggctgttg ttgaaaaata cgctttgacc  1200
atgaaggctt gtcgtatctt gcacaacact ccatcttctc aaggtggtat cggttccatt  1260
tacaactaca tctggccatc tttcacttta ggttgtggtt cttacggtgg taactccgtt  1320
tctgccaatg ttacctacca caacttgttg aacatcaaga gattggctga cagaagaaac  1380
aacttacaat ggttcagagt cccaccaaag atcttcttcg aacctcactc cattagatac  1440
ttggctgaat tgaaggaatt gtccaagatt ttcattgtct ctgacagaat gatgtacaaa  1500
ttgggttacg ttgacagagt tatggatgtc ttgaagagaa gatccaacga agttgaaatt  1560
gaaatcttca tcgatgttga accagaccca tccattcaaa ccgtccaaaa ggggtttggct  1620
gtcatgaaca ctttcggtcc agacaacatc attgccattg gtggtggttc tgccatggat  1680
gctgccaaga tcatgtggtt attatacgaa catccagaag ctgatttctt cgctatgaag  1740
caaaaattca tcgatttaag aaagagagct ttcaagttcc caaccatggg taagaaggcc  1800
agattaatct gtatcccaac cacttctggt accggttctg aagtcacccc attcgctgtc  1860
atctctgacc acgaaactgg taagaagtat ccattggctg actactcttt gaccccatcc  1920
gttgccattg ttgacccaat gtttaccatg tccttgccta agagagccat tgctgacact  1980
ggtttggatg tcttagtcca cgctactgaa gcttacgttt ctgttatggc taacgaatac  2040
actgacggtt tggccagaga agctgtcaaa ttggtttttcg aaaacttgtt gaaatcttac  2100
aacggtgact tggaagctcg tgaaaagatg cacaacgctg ctaccattgc tggtatggcc  2160
tttgcttctg ctttccttggg tatggaccat tccatggctc acaaggtcgg tgctgctttc  2220
catttgccac acggtagatg tgttgccgtt ttgttgcctc acgttatcag atacaacggt  2280
caaaagccaa gaaagttggc catgtggcca aagtacaact tctacaaggc tgatcaaaga  2340
tacatggaat ggctcaaat ggtcggtttg aagtgtaaca ccccagctga aggtgtcgaa  2400
gcctttgcca aggcttgtga agaattgatg aaggctactg aaaccatcac tggtttcaag  2460
aaggccaaca ttgatgaagc tgcttggatg tccaaggttc cagaaatggc tctattggct  2520
ttcgaagacc aatgttctcc agctaaccca agagtcccaa tggttaagga catggaaaag  2580
attttgaagg ctgcttacta cccaatcgct                                    2610
```

```
SEQ ID NO: 50          moltype = AA  length = 870
FEATURE                Location/Qualifiers
source                 1..870
                       mol_type = protein
                       organism = Entamoeba histolytica
SEQUENCE: 50
MSTQQTMTVD EHINQLVRKA QVALKEYLKP EYTQEKIDYI VKKASVAALD QHCALAAAAV  60
EETGRGIFED KATKNIFACE HVTHEMRHAK TVGIINVDPL YGITEIAEPV GVVCGVTPVT  120
NPTSTAIFKS LISIKTRNPI VFSFHPSALK CSIMAAKIVR DAAIAAGAPE NCIQWIEFGG  180
IEASNKLMNH PGVATILATG GNAMVKAAYS SGKPALGVGA GNVPTYIEKT CNIKQAANDV  240
VMSKSFDNGM ICASEQAAII DKEIYDQVVE EMKTLGAYFI NEEEKAKLEK FMFGVNAYSA  300
DVNNARLNPK CPGMSPQWFA EQVGIKVPED CNIICAVCKE VGPNEPLTRE KLSPVLAILK  360
```

```
AENTQDGIDK AEAMVEFNGR GHSAAIHSND KAVVEKYALT MKACRILHNT PSSQGGIGSI  420
YNYIWPSFTL GCGSYGGNSV SANVTYHNLL NIKRLADRRN NLQWFRVPPK IFFEPHSIRY  480
LAELKELSKI FIVSDRMMYK LGYVDRVMDV LKRRSNEVEI EIFIDVEPDP SIQTVQKGLA  540
VMNTFGPDNI IAIGGGSAMD AAKIMWLLYE HPEADFFAMK QKFIDLRKRA FKFPTMGKKA  600
RLICIPTTSG TGSEVTPFAV ISDHETGKKY PLADYSLTPS VAIVDPMFTM SLPKRAIADT  660
GLDVLVHATE AYVSVMANEY TDGLAREAVK LVFENLLKSY NGDLEAREKM HNAATIAGMA  720
FASAFLGMDH SMAHKVGAAF HLPHGRCVAV LLPHVIRYNG QKPRKLAMWP KYNFYKADQR  780
YMELAQMVGL KCNTPAEGVE AFAKACEELM KATETITGFK KANIDEAAWM SKVPEMALLA  840
FEDQCSPANP RVPMVKDMEK ILKAAYYPIA                                    870

SEQ ID NO: 51           moltype = DNA   length = 2658
FEATURE                 Location/Qualifiers
source                  1..2658
                        mol_type = other DNA
                        note = E2
                        organism = Piromyces sp.
SEQUENCE: 51
atgtccggat tacaaatgtt ccaaaacctt tctctttacg gtagtctcgc cgaaatcgat  60
actagcgaaa agcttaacga agctatggac aaattaactg ctgcccaaga acaattcaga  120
gaatacaacc aagaacaagt tgacaaaatc ttcaaggctg ttgctttagc tgcttctcaa  180
aaccgtgttg ctttcgctaa gtacgcacac gaagaaaccc aaaagggtgt tttcgaagat  240
aaggttatca agaacgaatt cgctgctgat tacatttacc acaagtactg caatgacaag  300
accgccggta tcattgaata tgatgaagcc aatggtctta tggaaattgc tgaaccagtt  360
ggtccagttg ttggtattgc tccagttact aacccaactt ctactatcat ctacaagtct  420
ttaattgcct taaagacccg taactgtatt atcttctcac cacatccagg agctcacaag  480
gcctctgttt tcgttgttaa ggtcttacac caagctgctg ttaaggctgg tgccccagaa  540
aactgtattc aaatcatctt cccaaagatg gatttaacta ctgaattatt acaccaccaa  600
aagactcgtt tcatttgggc tactggtggt ccaggtttag ttcacgcctc ttacacttct  660
ggtaagccag ctcttggtgg tggtccaggt aatgctccag ctcttattga tgaaacttgt  720
gatatgaacg aagctgttgg ttctatcgtt gtttctaaga ctttcgattg tggtatgatc  780
tgtgccactg aaaacgctgt tgtcgttgtc gaatctgtct acgaaaactt cgttgctacc  840
atgaagaagc gtggtgccta cttcatgact ccagaagaaa ccaagaaggc ttctaacctt  900
cttttcggag aaggtatgag attaaatgct aaggctgttg gtcaaactgc caagacttta  960
gctgaaatgg ccggtttcga agtcccagaa aacaccgttg ttctctgtgg tgaagcttct  1020
gaagttaaat tcgaagaacc aatggctcac gaaaagttaa ctactatcct cggtatctac  1080
aaggctaagg actttgacga tggtgtcaga ttatgtaagg aattagttac tttcggtggt  1140
aagggtcaca ctgctgttct ctacaccaac caaaacaaca aggaccgtat tgaaaagtac  1200
caaaacgaag ttccagcctt cccacatctta gttgacatgc catcttccct cggttgtatt  1260
ggtgatatgt acaacttccg tcttgctcca gctcttacca ttacttgtgg tactatgggt  1320
ggtggttcct cctctgataa cattggtcca aagcacttac ttaacatcaa gcgtgttggt  1380
atgagacgcg aaaacatgct ttggttcaag attccaaagt ctgtctactt caagcgtgct  1440
atcctttctg aagctttatc tgacttacgt gacacccaca gcgtgctat cattattacc  1500
gataaacta tgactatgtt aggtcaaact gacaagatca ttaaggcttg tgaaggtcat  1560
ggtatggtct gcactgtcta cgataaggtt gtcccagatc caactatcaa gtgtattatg  1620
gaaggtgtta atgaaatgaa cgtcttcaag ccagatttag ctattgctct tggtggtggt  1680
tctgctatgg atgccgctaa gatgatgcgt ttattctacg aatacccaga ccaagactta  1740
caagatattg ctactcgttt cgtcgatatc cgtaagcgtg ttgttggttg tccaaagctt  1800
ggtagactta ttaagactct tgtctgtatc ccaactacct ctggtactgg tgccgaagtt  1860
actccattcg ctgtcgttac ctctgaagaa ggtcgtaagt acccattagt cgactacgaa  1920
cttactccag atatggctat tgttgatcca gaattcgctg ttggtatgcc aaagcgttta  1980
acttcttgga ctggtattga tgctcttacc cacgccattg aatcttacgt ttctattatg  2040
gctactgact tcactagacc atactctctc cgtgctgttg tcttatctt cgaatccctt  2100
tcccttgctt acaacaacgg taaggatatt gaagctcgtg aaaagatgca caatgcttct  2160
gctattgctg gtatggcctt tgccaacgct ttccttggtt gttgtcactc tgttgctcac  2220
caacttggtt ccgtctacca cattccacac ggtcttgcca acgctttaat gctttctcac  2280
atcattaagt acaacgctac tgactctcca gttaagatgg gtaccttccc acaatacaag  2340
tacccacaag ctatgcgtca ctacgctgaa attgctgaac tcttattacc accaactcaa  2400
gttgttaaga tgactgatgt tgataaggtt caatacttaa ttgaccgtgt tgaacaatta  2460
aaggctgacg ttggtattcc aaagtctatt aaggaaactg gaatggttac tgaagaagac  2520
ttcttcaaca aggttgacca agttgctatc atggccttcg atgaccaatg tactggtgct  2580
aacccacgtt acccattagt ttctgaatta aaacaattaa tgattgatgc ctggaacggt  2640
gttgtcccaa agctctaa                                               2658

SEQ ID NO: 52           moltype = AA   length = 885
FEATURE                 Location/Qualifiers
source                  1..885
                        mol_type = protein
                        note = E2
                        organism = Piromyces sp.
SEQUENCE: 52
MSGLQMFQNL SLYGSLAEID TSEKLNEAMD KLTAAQEQFR EYNQEQVDKI FKAVALAASQ  60
NRVAFAKYAH EETQKGVFED KVIKNEFAAD YIYHKYCNDK TAGIIEYDEA NGLMEIAEPV  120
GPVVGIAPVT NPTSTIIYKS LIALKTRNCI IFSPHPGAHK ASVFVVKVLH QAAVKAGAPE  180
NCIQIIFPKM DLTTELLHHQ KTRFIWATGG PGLVHASYTS GKPALGGGPG NAPALIDETC  240
DMNEAVGSIV VSKTFDCGMI CATENAVVVV ESVYENFVAT MKKRGAYFMT PEETKKASNL  300
LFGEGMRLNA KAVGQTAKTL AEMAGFEVPE NTVVLCGEAS EVKFEEPMAH EKLTTILGIY  360
KAKDFDDGVR LCKELVTFGG KGHTAVLYTN QNNKDRIEKY QNEVPAFHIL VDMPSSLGCI  420
GDMYNFRLAP ALTITCGTMG GGSSSDNIGP KHLLNIKRVG MRRENMLWFK IPKSVYFKRA  480
ILSEALSDLR DTHKRAIIIT DRTMTMLGQT DKIIKACEGH GMVCTVYDKV VPDPTIKCIM  540
```

-continued

```
EGVNEMNVFK PDLAIALGGG SAMDAAKMMR LFYEYPDQDL QDIATRFVDI RKRVVGCPKL  600
GRLIKTLVCI PTTSGTGAEV TPFAVVTSEE GRKYPLVDYE LTPDMAIVDP EFAVGMPKRL  660
TSWTGIDALT HAIESYVSIM ATDFTRPYSL RAVGLIFESL SLAYNNGKDI EAREKMHNAS  720
AIAGMAFANA FLGCCHSVAH QLGSVYHIPH GLANALMLSH IIKYNATDSP VKMGTFPQYK  780
YPQAMRHYAE IAELLLPPTQ VVKMTDVDKV QYLIDRVEQL KADVGIPKSI KETGMVTEED  840
FFNKVDQVAI MAFDDQCTGA NPRYPLVSEL KQLMIDAWNG VVPKL                  885
```